US007652024B2

(12) United States Patent
Bakshi et al.

(10) Patent No.: US 7,652,024 B2
(45) Date of Patent: Jan. 26, 2010

(54) ACYLATED SPIROPIPERIDINE DERIVATIVES AS MELANOCORTIN-4 RECEPTOR MODULATORS

(75) Inventors: Raman K. Bakshi, Edison, NJ (US); James P. Dellureficio, Millington, NJ (US); Peter H. Dobbelaar, Morris Plains, NJ (US); Liangqin Guo, Edison, NJ (US); Shuwen He, Edison, NJ (US); Qingmei Hong, Scotch Plains, NJ (US); Ravi P. Nargund, East Brunswick, NJ (US); Zhixiong Ye, West Windsor, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 100 days.

(21) Appl. No.: 12/083,567

(22) PCT Filed: Oct. 13, 2006

(86) PCT No.: PCT/US2006/040198

§ 371 (c)(1),
(2), (4) Date: Apr. 15, 2008

(87) PCT Pub. No.: WO2007/047496

PCT Pub. Date: Apr. 26, 2007

(65) Prior Publication Data

US 2009/0325990 A1 Dec. 31, 2009

Related U.S. Application Data

(60) Provisional application No. 60/727,647, filed on Oct. 18, 2005.

(51) Int. Cl.
*A61K 31/438* (2006.01)
*C07D 491/107* (2006.01)

(52) U.S. Cl. .................. 514/278; 546/17; 544/125; 514/232.8

(58) Field of Classification Search ................ 514/278, 514/232.8; 546/17; 544/125
See application file for complete search history.

(56) References Cited

U.S. PATENT DOCUMENTS

| 5,576,290 | A | 11/1996 | Hadley |
| 6,051,555 | A | 4/2000 | Hadley |
| 2003/0092732 | A1 | 5/2003 | Yu et al. |
| 2003/0096827 | A1 | 5/2003 | Yu et al. |
| 2003/0232807 | A1 | 12/2003 | Poindexter et al. |
| 2004/0224901 | A1 | 11/2004 | Poindexter et al. |

FOREIGN PATENT DOCUMENTS

| WO | WO 99/64002 | 12/1999 |
| WO | WO 00/74679 | 12/2000 |
| WO | WO 01/70337 | 9/2001 |
| WO | WO 01/70708 | 9/2001 |
| WO | WO 01/91752 | 12/2001 |
| WO | WO 02/15909 | 2/2002 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/068387 | 9/2002 |
| WO | WO 02/068388 | 9/2002 |
| WO | WO 02/079146 | 10/2002 |
| WO | WO 03/000677 | 1/2003 |
| WO | WO 03/007949 | 1/2003 |
| WO | WO 03/009847 | 2/2003 |
| WO | WO 03/009850 | 2/2003 |
| WO | WO 03/061660 | 7/2003 |
| WO | WO 03/068738 | 8/2003 |
| WO | WO 03/092690 | 11/2003 |
| WO | WO 03/093234 | 11/2003 |
| WO | WO 03/094918 | 11/2003 |
| WO | WO 2004/024720 | 3/2004 |
| WO | WO 2004/048345 | 6/2004 |
| WO | WO 2004/058735 | 7/2004 |
| WO | WO 2004/078716 | 9/2004 |
| WO | WO 2004/078717 | 9/2004 |
| WO | WO 2004/087159 | 10/2004 |
| WO | WO 2004/089307 | 10/2004 |
| WO | WO 2004/112793 | 12/2004 |
| WO | WO 2005/009950 | 2/2005 |
| WO | WO 2005/040109 | 5/2005 |
| WO | WO 2005/042516 | 5/2005 |

OTHER PUBLICATIONS

H. Wessells et al., "Synthetic Melanotropic Peptide Initiates Erections in Men with Psychogenic Erectile Dysfuntion: Double Blind, Placebo Controlled Crossover Study", Journal of Urology, vol. 160, pp. 389-393 (1998).
R. Dorr et al., "Evaluation of Melanotan-II, a Superpotent Cyclic Melanotropic Peptide in a Pilot Phase-I Clinical Study", Life Sciences, vol. 58, No. 20, pp. 1777-1784 (1996).

*Primary Examiner*—Charanjit S Aulakh
(74) *Attorney, Agent, or Firm*—Baerbel R. Brown; Richard C. Billups; Catherine D. Fitch

(57) ABSTRACT

Certain novel N-acylated spiropiperidine derivatives are ligands of the human melanocortin receptor(s) and, in particular, are selective ligands of the human melanocortin-4 receptor (MC-4R). They are therefore useful for the treatment, control, or prevention of diseases and disorders responsive to the modulation of MC-4R, such as obesity, diabetes, nicotine addiction, alcoholism, sexual dysfunction, including erectile dysfunction and female sexual dysfunction.

19 Claims, No Drawings

ACYLATED SPIROPIPERIDINE DERIVATIVES AS MELANOCORTIN-4 RECEPTOR MODULATORS

CROSS-REFERENCE TO RELATED APPLICATIONS

This application is a U.S. National Phase application under 35 U.S.C. §371 of PCT Application No. PCT/US2006/040198, filed Oct. 13, 2006, which published as WO 2007/047496 on Apr. 26, 2007, and claims priority under 35 U.S.C. §119 from U.S. Provisional Application No. 60/727,647, filed Oct. 18, 2005.

FIELD OF THE INVENTION

The present invention relates to acylated spiropiperidine derivatives, their synthesis, and their use as melanocortin receptor (MC-R) ligands useful to modulate bodyweight. More particularly, the compounds of the present invention are ligands of the melanocortin-4 receptor (MC-4R) and are thereby useful for the treatment of disorders responsive to the modulation of the melanocortin-4 receptor, such as obesity, diabetes, male sexual dysfunction, female, sexual dysfunction, cachexia, anorexia, wasting, and weight loss.

BACKGROUND OF THE INVENTION

Obesity is a major health concern in Western societies. It is estimated that about 97 million adults in the United States are overweight or obese. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; dyslipidemias; hyperlipidemia; endometrial, breast, prostate and colon cancer; osteoarthritis; respiratory complications, such as obstructive sleep apnea; cholelithiasis; gallstones; arteriosclerosis; heart disease; abnormal heart rhythms; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death.

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," *Brain Research*, 80: 302-306 (1998)). Evidence for the involvement of MC-R's in obesity includes: i) the agouti (A$^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (D. Huszar et al., *Cell*, 88: 131-141 (1997)) recapitulate the phenotype of the agouti mouse and these mice are obese; iii) the cyclic heptapeptide MT-II (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-LR, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," Society for Neuroscience Abstracts, 23: 673 (1997)).

Studies have shown that the melanocortin system contributes to the regulation of feeding behavior and bodyweight. Administration of melanocortin antagonists increases food intake and bodyweight, while administration of melanocortin agonists decreases food intake and bodyweight. Support for the role of the MC-4R subtype in energy balance is demonstrated by evidence showing that the melanocortin-4 receptor deficiency in humans appears to be the most common monogenetic form of obesity with about 5-6% of obese patients showing this mutation. Furthermore, the severity of the phenotype appears to be greater in individuals that have mutations that result in complete loss of functioning. Based on these findings, the melanocortin system has been targeted for the development of small molecule agonists to treat obesity and small molecule antagonists to treat cachexia.

Weight loss drugs that are currently used in monotherapy for the treatment of obesity have limited efficacy and significant side effects. Studies of the weight loss medications orlistat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. &: 189-98) and phentermine (Douglas, A. et al. (1983) Int. J. Obes. 7:591-5) have demonstrated a limited weight loss of about 5%-10% of body weight for drug compared to placebo. In particular, both sibutramine and orlistat reduce body weight less than 10% over a 6 month or a 1 year period. The side effects of these drugs and anti-obesity agents further limit their use. Dexfenfluramine was withdrawn from the market because of suspected heart valvulopathy; orlistat is limited by gastrointestinal side effects; the use of topiramate is limited by central nervous system effects; and the use of sibutramine is limited by its cardiovascular side effects which have led to reports of deaths and its withdrawal from the market in Italy.

There is a need for a weight loss treatment with enhanced efficacy and fewer undesirable side effects. The instant invention addresses this problem by providing melanocortin receptor (MC-R) agonists, and in particular selective agonists of the melanocortin-4 receptor (MC-4R), useful in the treatment and prevention of obesity and obesity-related disorders, including diabetes.

Melanocortin receptor involvement in male and female sexual dysfunction has also been reported. Approximately 140 million men worldwide suffer from impotency or erectile dysfunction. Current treatment options for erectile dysfunction include phosphodiesterase V inhibitors, such as sildenafil citrate (Viagra®), vardenafil hydrochloride (Levitra®), and tadalafil (Cialis®). Sildenafil is effective in about 70% of patients, however it is contraindicated for patients with unstable heart conditions or cardiovascular disease, in particular patients taking nitrates, such as nitroglycerin, to treat angina. Vardenafil and Tadalafil are also contraindicated for patients taking nitrates and alpha blockers due to the risk of a sudden blood pressure drop resulting in fainting, heart attack or stroke. Other adverse effects associated with the clinical use of these PDE-5 inhibitors include headache, flushing, dyspepsia, dizziness, indigestion, and "abnormal vision, which is characterized by a bluish tinge to vision, but also an increased sensitivity to light or blurred vision. Sildenafil is also being evaluated for the treatment of female sexual dysfunction.

There is a need for a sexual dysfunction treatment with fewer undesirable side effects. The instant invention addresses this problem by providing melanocortin receptor (MC-R) agonists, and in particular selective agonists of the melanocortin-4 receptor (MC-4R), useful in the treatment and prevention of obesity and obesity-related disorders, including diabetes.

Synthetic melanocortin receptor agonists (melanotropic peptides) have been found to initiate erections in men with psychogenic erectile dysfunction. The centrally acting α-melanocyte-stimulating hormone analog, melanotan-II (MT-II), exhibited a 75% response rate when injected intramuscularly or subcutaneously into males with psychogenic erectile dysfunction [See H. Wessells et al., "Synthetic Melanotropic Peptide Initiates Erections in Men With Psychogenic Erectile Dysfunction: Double-Blind, Placebo Controlled Crossover Study," *J. Urol.*, 160: 389-393 (1998); *Fifteenth American Peptide Symposium*, Jun. 14-19, 1997 (Nashville Tenn.)]. MT-II (the cyclic heptapeptide Ac-Nle-c [Asp-His-DPhe-Arg-Trp-Lys]-NH$_2$) is a non-selective MC-1R, -3R, -4R, and -5R agonist (Dorr et al., *Life Sciences*, Vol. 58, 1777-1784, 1996). Adverse reactions observed with MT-II include nausea, flushing, loss of appetite, stretching, and yawning and may be the result of activation of MC-1R, MC-2R, MC-3R, and/or MC-5R. Additionally, MT-II must be administered parenterally, such as by subcutaneous, intravenous, or intramuscular route, since it is not absorbed into the systemic circulation when given by the oral route.

Compositions of melanotropic peptides and methods for the treatment of psychogenic erectile dysfunction are disclosed in U.S. Pat. No. 5,576,290. Methods of stimulating sexual response in females using melanotropic peptides have been disclosed in U.S. Pat. No. 6,051,555. Spiropiperidine, piperidine and piperazine derivatives have been disclosed in WO 99/64002; WO 00/74679; WO 01/70708; WO 01/70337; WO 01/91752; WO 02/015909; WO 02/059095; WO 02/059107; WO 02/059108; WO 02/059117; WO 02/068387; WO 02/068388; WO 02/079146; WO 03/061660, WO 03/000677; WO 03/007949; WO 03/009847; WO 03/009850; WO 03/068738; WO 03/092690; WO 03/093234; WO 03/094918; WO 04/024720; WO 04/048345; WO 04/058735; WO 04/078717; WO 04/112793; WO 04/224957; WO 04/089307; WO 04/078716; WO 04/078717; WO 04/087159; WO 05/042516; WO 05/040109; WO 05/009950; US2003096827; US2003092732; US2003232807, and US2004224901 as agonists of the melanocortin receptor(s) and particularly as selective agonists of the MC-4R receptor and thereby useful for the treatment of diseases and disorders, such as obesity, diabetes, and sexual dysfunction, including erectile dysfunction and female sexual dysfunction.

Because of the unresolved deficiencies of the various pharmacological agents discussed above, there is a continuing need in the medical arts for improved methods and compositions to treat individuals suffering from psychogenic and/or organic sexual dysfunction. Such methods should have wider applicability, enhanced convenience and ease of compliance, short onset of action, reasonably long duration of action, and minimal side effects with few contraindications, as compared to agents now available.

It is therefore an object of the present invention to provide acylated spiropiperidine derivatives which are melanocortin receptor agonists and thereby useful to treat obesity, diabetes, male sexual dysfunction, female sexual dysfunction, nicotine addiction and alcoholism.

It is another object of the present invention to provide acylated spiropiperidine derivatives which are selective ligands of the melanocortin-4 (MC-4R) receptor.

It is another object of the present invention to provide pharmaceutical compositions comprising the melanocortin receptor agonists or ligands of the present invention with a pharmaceutically acceptable carrier.

It is another object of the present invention to provide methods for the treatment or prevention of disorders, diseases, or conditions responsive to the modulation of the melanocortin-4 receptor in a subject in need thereof by administering the compounds and pharmaceutical compositions of the present invention.

It is another object of the present invention to provide methods for the treatment or prevention of obesity, diabetes mellitus, male sexual dysfunction, female sexual dysfunction, nicotine addiction and alcoholism by administering the compounds and pharmaceutical compositions of the present invention to a subject in need thereof.

It is another object of the present invention to provide methods for the treatment of erectile dysfunction by administering the compounds and pharmaceutical compositions of the present invention to a subject in need thereof.

These and other objects will become readily apparent from the detailed description that follows.

SUMMARY OF THE INVENTION

The present invention relates to novel N-acylated spiropiperidines of structural formula I:

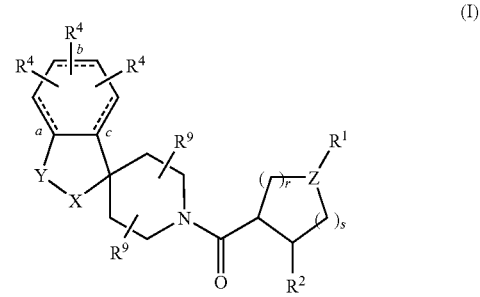

The compounds of structural formula I are effective as melanocortin receptor ligands and are particularly effective as selective ligands of the melanocortin-4 receptor. They are therefore useful for the treatment and/or prevention of disorders responsive to the modulation of the melanocortin-4 receptor, such as obesity, diabetes, obesity-related disorders, nicotine addiction, alcoholism, female sexual dysfunction, and male sexual dysfunction, in particular male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the modulation of the melanocortin-4 receptor in a mammal in need thereof by administering the compounds and pharmaceutical compositions of the present invention.

The present invention further relates to the use of the compounds of the present invention in the preparation of a medicament useful for the treatment or prevention of disorders, diseases, or conditions responsive to the modulation of the melanocortin-4 receptor in a mammal in need thereof by administering the compounds and pharmaceutical compositions of the present invention.

DETAILED DESCRIPTION OF THE INVENTION

The present invention relates to N-acylated spiropiperidine derivatives useful as melanocortin receptor modulators, in particular, as selective melanocortin-4 receptor ligands. Compounds of the present invention are described by structural formula I:

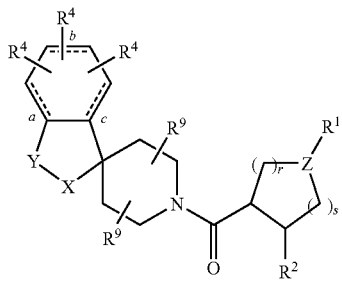

(I)

or a pharmaceutically acceptable salt thereof; wherein a, b and c are all single bonds or all double bonds;

Y is selected from the group consisting of:
  (1) —C($R^7$)($R^6$),
  (2) —N($R^6$),
  (3) C(O),
  (4) oxygen,
  (5) sulfur,
  (6) S(O), and
  (7) S(O)$_2$;

X is selected from the group consisting of:
  (1) CH$_2$,
  (2) —C($R^7$)($R^6$),
  (3) C(O),
  (4) oxygen,
  (5) N($R^6$),
  (6) sulfur,
  (7) S(O), and
  (8) S(O)$_2$;

Z is selected from the group consisting of:
  (1) CH, and
  (2) N;

$R^1$ is selected from the group consisting of:
  (1) —(CH$_2$)$_n$C$_{2-7}$heterocycloalkyl, and
  (2) —N($R^7$)C$_{2-7}$heterocycloalkyl, wherein heterocycloalkyl, and (CH$_2$)$_n$ are unsubstituted or substituted with one to three groups independently selected from $R^3$ and oxo;

$R^2$ is selected from the group consisting of:
  (1) phenyl,
  (2) naphthyl, and
  (3) heteroaryl, wherein phenyl, naphthyl, and heteroaryl are unsubstituted or substituted with one to three groups independently selected from $R^8$;

$R^3$ and $R^4$ are independently selected from the group consisting of:
  (1) hydrogen,
  (2) C$_{1-8}$ alkyl,
  (3) —(CH$_2$)$_n$-phenyl,
  (4) —(CH$_2$)$_n$-naphthyl,
  (5) —(CH$_2$)$_n$-heteroaryl,
  (6) —(CH$_2$)$_n$C$_{2-7}$ heterocycloalkyl,
  (7) —(CH$_2$)$_n$C$_{3-7}$ cycloalkyl,
  (8) halogen,
  (9) —OR$^5$,
  (10) —(CH$_2$)$_n$N(R$^5$)$_2$,
  (11) —(CH$_2$)$_n$C≡N,
  (12) —(CH$_2$)$_n$C(O)OR$^5$,
  (13) —(CH$_2$)$_n$OC(O)R$^5$,
  (14) —NO$_2$,
  (15) —(CH$_2$)$_n$NR$^5$S(O)$_p$R$^5$,
  (16) —(CH$_2$)$_n$N(S(O)$_p$R$^5$)$_2$,
  (17) —(CH$_2$)$_n$S(O)$_p$N(R$^5$)$_2$,
  (18) —(CH$_2$)$_n$S(O)$_p$R$^5$,
  (19) —(CH$_2$)$_n$NR$^5$C(O)N(R$^5$)$_2$,
  (20) —(CH$_2$)$_n$C(O)N(R$^5$)$_2$,
  (21) —(CH$_2$)$_n$NR$^5$C(O)R$^5$,
  (22) —(CH$_2$)$_n$NR$^5$CO$_2$R$^5$,
  (23) —(CH$_2$)$_n$NR$^5$C(O)-heteroaryl,
  (24) —(CH$_2$)$_n$C(O)NR$^5$N(R$^5$)$_2$,
  (25) —(CH$_2$)$_n$C(O)NR$^5$NR$^5$C(O)R$^5$,
  (26) —O(CH$_2$)$_n$C(O)N(R$^5$)$_2$,
  (27) —CF$_3$,
  (28) —CH$_2$CF$_3$,
  (29) —OCF$_3$, and
  (30) —OCH$_2$CF$_3$;

wherein phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;

each $R^5$ is independently selected from the group consisting of:
  (1) hydrogen,
  (2) C$_{1-8}$ alkyl,
  (3) —(CH$_2$)$_n$C$_{3-7}$ cycloalkyl,
  (4) —(CH$_2$)$_n$C$_{2-7}$ heterocycloalkyl,
  (5) —(CH$_2$)$_n$-phenyl,
  (6) —(CH$_2$)$_n$-naphthyl,
  (7) —(CH$_2$)$_n$-heteroaryl, and
  (8) —(CH$_2$)$_n$C$_{3-7}$ bicycloalkyl;

wherein alkyl, phenyl, heteroaryl, heterocycloalkyl, naphthyl, cycloalkyl, bicycloalkyl and (CH$_2$) are unsubstituted or substituted with one to three groups independently selected from halogen, C$_{1-4}$ alkyl, hydroxy, and C$_{1-4}$ alkoxy, or wherein two $R^5$ groups together with the atom to which they are attached form a 4- to 8-membered mono- or bicyclic ring system optionally containing an additional heteroatom selected from O, S, and —NC$_{1-4}$ alkyl;

each $R^6$ is independently selected from the group consisting of:
  (1) —(CH$_2$)$_n$C$_{2-7}$ heterocycloalkyl,
  (2) C$_{1-6}$ alkyl,
  (3) —(CH$_2$)$_n$C$_{3-7}$ cycloalkyl, (4) —$(CH_2)_n C_{2-7}$ heterocycloalkyl,
(5) —$(CH_2)_n$-phenyl,
(6) —$(CH_2)_n$-heteroaryl,
(7) —$(CH_2)_n C(O)R^5$,
(8) —$(CH_2)_n C(O)OR^5$,
(9) —$(CH_2)_n C(OH)R^5$,
(10) —$(CH_2)_n C(O)(CH_2)_n N(R^5)_2$,
(11) —$(CH_2)_n C(O)(CH_2)_n NR^7 R^8$,
(12) —$(CH_2)_n$—$OR^5$,
(13) —$(CH_2)_n$—$OC(O)R^5$,
(14) —$(CH_2)_n$—$O$—$(CH_2)_n$—$N(R^5)_2$,
(15) —$(CH_2)_n CN$,
(16) —$(CH_2)_n N(R^5)_2$,
(17) —$(CH_2)_n N(R^5)C(O)R^5$,
(18) —$(CH_2)_n N(R^5)C(O)OR^5$,
(19) —$(CH_2)_n N(R^5)C(O)(CH_2)_n N(R^5)_2$,
(20) —$(CH_2)_n N(R^5)$—$S(O)$—$C_{1-8}$ alkyl,
(21) —$(CH_2)_n N(R^5)$—$S(O)_2$—$C_{1-8}$ alkyl,
(22) —$(CH_2)_n$—$S$—$R^5$,
(23) —$(CH_2)_n$—$S(O)$—$R^5$, and
(24) —$(CH_2)_n$—$S(O)_2$—$R^5$, wherein phenyl and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene ($CH_2$) in $R^6$ is unsubstituted or substituted with one to two groups independently selected from halogen, hydroxy, and $C_{1-4}$ alkyl; or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^7$ is independently selected from the group consisting of:
(1) hydrogen, and
(2) $C_{1-8}$ alkyl, wherein alkyl is unsubstituted or substituted with one to three groups independently selected from halogen, $C_{1-4}$ alkyl, hydroxy, and $C_{1-4}$ alkoxy;

each $R^8$ is independently selected from the group consisting of:
(1) $C_{1-6}$ alkyl,
(2) —$(CH_2)_n$phenyl,
(3) —$(CH_2)_n$naphthyl,
(4) —$(CH_2)_n$heteroaryl,
(5) —$(CH_2)_n C_{2-7}$heterocycloalkyl,
(6) —$(CH_2)_n C_{3-7}$cycloalkyl,
(7) halogen,
(8) —$OR^5$,
(9) —$(CH_2)_n N(R^5)_2$,
(10) —$(CH_2)_n C\equiv N$,
(11) —$(CH_2)_n CO_2 R^5$,
(12) —$NO_2$,
(13) —$(CH_2)_n NR^5 S(O)_p R^5$,
(14) —$(CH_2)_n S(O)_p N(R^5)_2$,
(15) —$(CH_2)_n S(O)_p R^5$,
(16) —$(CH_2)_n NR^5 C(O)N(R^5)_2$,
(17) —$(CH_2)_n C(O)N(R^5)_2$,
(18) —$(CH_2)_n NR^5 C(O)R^5$,
(19) —$(CH_2)_n NR^5 CO_2 R^5$,
(20) —$(CH_2)_n NR^5 C(O)$-heteroaryl,
(21) —$(CH_2)_n C(O)NR^5 N(R^5)_2$,
(22) —$(CH_2)_n C(O)NR^5 NR^5 C(O)R^5$,
(23) —$O(CH_2)_n C(O)N(R^5)_2$,
(24) —$CF_3$,
(25) —$CH_2 CF_3$,
(26) —$OCF_3$, and
(27) —$OCH_2 CF_3$;

wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy;

each $R^9$ is independently selected from the group consisting of:
(1) hydrogen,
(2) —OH,
(3) $C_{1-8}$alkyl,
(4) —$OC_{1-8}$alkyl,
(5) halogen;
(6) —$NR^5$,
(7) —$SR^5$, and
(8) —$CF_3$, wherein two $C_{1-8}$alkyl substituents along with the atoms to which they are attached can form a 4- to 8-membered ring;

r is 1 or 2;

s is 1 or 2;

n is 0, 1, 2, or 3; and p is 0, 1, or 2.

In another embodiment of the compounds of the present invention, there are provided compounds of structural formula IIa or IIb of the indicated relative stereochemical configurations having the trans orientation of the $R^2$ and piperidinecarbonyl substituents:

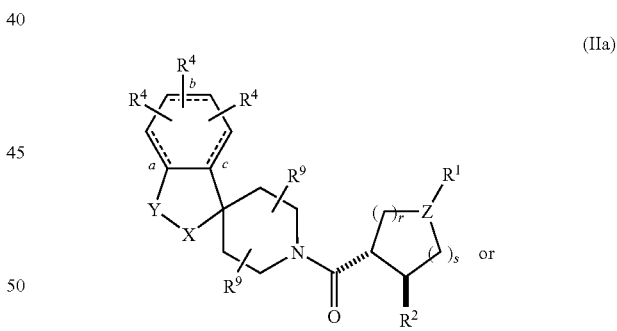

(IIa)

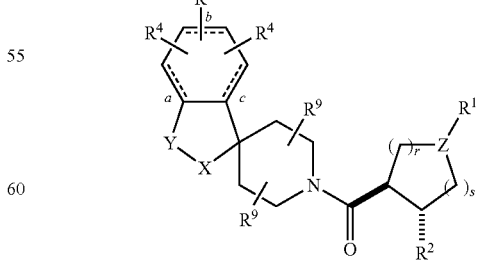

(IIb)

or a pharmaceutically acceptable salt thereof; wherein a, b and c are all single bonds or all double bonds;

Y is selected from the group consisting of:
- (1) —C(R$^7$)(R$^6$),
- (2) —N(R$^6$),
- (3) C(O),
- (4) oxygen,
- (5) sulfur,
- (6) S(O), and
- (7) S(O)$_2$;

X is selected from the group consisting of:
- (1) CH$_2$,
- (2) —C(R$^7$)(R$^6$),
- (3) C(O),
- (4) oxygen,
- (5) N(R$^6$),
- (6) sulfur,
- (7) S(O), and
- (8) S(O)$_2$;

Z is independently selected from the group consisting of:
- (1) CH, and
- (2) N;

R$^1$ is selected from the group consisting of:
- (1) —(CH$_2$)$_n$C$_{2-7}$heterocycloalkyl, and
- (2) —N(R$^7$)C$_{2-7}$heterocycloalkyl, wherein heterocycloalkyl, and (CH$_2$)$_n$ are unsubstituted or substituted with one to three groups independently selected from R$^3$ and oxo;

R$^2$ is selected from the group consisting of:
- (1) phenyl,
- (2) naphthyl, and
- (3) heteroaryl, wherein phenyl, naphthyl, and heteroaryl are unsubstituted or substituted with one to three groups independently selected from R$^8$;

R$^3$ and R$^4$ are independently selected from the group consisting of:
- (1) hydrogen,
- (2) C$_{1-8}$alkyl,
- (3) —(CH$_2$)$_n$phenyl,
- (4) —(CH$_2$)$_n$naphthyl,
- (5) —(CH$_2$)$_n$heteroaryl,
- (6) —(CH$_2$)$_n$C$_{2-7}$heterocycloalkyl,
- (7) —(CH$_2$)$_n$C$_{3-7}$cycloalkyl,
- (8) halogen,
- (9) —OR$^5$,
- (10) —(CH$_2$)$_n$N(R$^5$)$_2$,
- (11) —(CH$_2$)$_n$C≡N,
- (12) —(CH$_2$)$_n$C(O)OR$^5$,
- (13) —(CH$_2$)$_n$OC(O)R$^5$,
- (14) —NO$_2$,
- (15) —(CH$_2$)$_n$NR$^5$S(O)$_p$R$^5$,
- (16) —(CH$_2$)$_n$N(S(O)$_p$R$^5$)$_2$,
- (17) —(CH$_2$)$_n$S(O)$_p$N(R$^5$)$_2$,
- (18) —(CH$_2$)$_n$S(O)$_p$R$^5$,
- (19) —(CH$_2$)$_n$NR$^5$C(O)N(R$^5$)$_2$,
- (20) —(CH$_2$)$_n$C(O)N(R$^5$)$_2$,
- (21) —(CH$_2$)$_n$NR$^5$C(O)R$^5$,
- (22) —(CH$_2$)$_n$NR$^5$CO$_2$R$^5$,
- (23) —(CH$_2$)$_n$NR$^5$C(O)-heteroaryl,
- (24) —(CH$_2$)$_n$C(O)NR$^5$N(R$^5$)$_2$,
- (25) —(CH$_2$)$_n$C(O)NR$^5$NR$^5$C(O)R$^5$,
- (26) —O(CH$_2$)$_n$C(O)N(R$^5$)$_2$,
- (27) —CF$_3$,
- (28) —CH$_2$CF$_3$,
- (29) —OCF$_3$, and
- (30) —OCH$_2$CF$_3$;

wherein phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;

each R$^5$ is independently selected from the group consisting of:
- (1) hydrogen,
- (2) C$_{1-8}$alkyl,
- (3) —(CH$_2$)$_n$C$_{3-7}$cycloalkyl,
- (4) —(CH$_2$)$_n$C$_{2-7}$heterocycloalkyl,
- (5) —(CH$_2$)$_n$phenyl,
- (6) —(CH$_2$)$_n$naphthyl,
- (7) —(CH$_2$)$_n$heteroaryl, and
- (8) —(CH$_2$)$_n$C$_{3-7}$ bicycloalkyl;

wherein alkyl, phenyl, heteroaryl, heterocycloalkyl, naphthyl, cycloalkyl, bicycloalkyl and (CH$_2$) are unsubstituted or substituted with one to three groups independently selected from halogen, C$_{1-4}$ alkyl, hydroxy, and C$_{1-4}$ alkoxy, or wherein two R$^5$ groups together with the atom to which they are attached form a 4- to 8-membered mono- or bicyclic ring system optionally containing an additional heteroatom selected from O, S, and —NC$_{1-4}$ alkyl;

each R$^6$ is independently selected from the group consisting of:
- (1) —(CH$_2$)$_n$C$_{2-7}$heterocycloalkyl,
- (2) C$_{1-6}$alkyl,
- (3) —(CH$_2$)$_n$C$_{3-7}$cycloalkyl,
- (4) —(CH$_2$)$_n$C$_{2-7}$heterocycloalkyl,
- (5) —(CH$_2$)$_n$phenyl,
- (6) —(CH$_2$)$_n$heteroaryl,
- (7) —(CH$_2$)$_n$C(O)R$^5$,
- (8) —(CH$_2$)$_n$C(O)OR$^5$,
- (9) —(CH$_2$)$_n$C(OH)R$^5$,
- (10) —(CH$_2$)$_n$C(O)(CH$_2$)$_n$N(R$^5$)$_2$,
- (11) —(CH$_2$)$_n$C(O)(CH$_2$)$_n$NR$^7$R$^8$,
- (12) —(CH$_2$)$_n$—OR$^5$,
- (13) —(CH$_2$)$_n$—OC(O)R$^5$,
- (14) —(CH$_2$)$_n$—O—(CH$_2$)$_n$—N(R$^5$)$_2$,
- (15) —(CH$_2$)$_n$CN,
- (16) —(CH$_2$)$_n$N(R$^5$)$_2$,
- (17) —(CH$_2$)$_n$N(R$^5$)C(O)R$^5$,
- (18) —(CH$_2$)$_n$N(R$^5$)C(O)OR$^5$,
- (19) —(CH$_2$)$_n$N(R$^5$)C(O)(CH$_2$)$_n$N(R$^5$)$_2$,
- (20) —(CH$_2$)$_n$N(R$^5$)—S(O)—C$_{1-8}$ alkyl,
- (21) —(CH$_2$)$_n$N(R$^5$)—S(O)$_2$—C$_{1-8}$ alkyl,
- (22) —(CH$_2$)$_n$—S—R$^5$,
- (23) —(CH$_2$)$_n$—S(O)—R$^5$, and
- (24) —(CH$_2$)$_n$—S(O)$_2$—R$^5$, wherein phenyl, and heteroaryl are unsubstituted or substituted with one to three groups independently selected from R$^3$, and wherein alkyl, cycloalkyl and heterocycloalkyl are unsubstituted or substituted with one to three groups independently selected from R$^3$ and oxo, and wherein any methylene (CH$_2$) in R$^6$ is unsubstituted or substituted with one to two groups independently selected from halogen, hydroxy, and C$_{1-4}$ alkyl; or wherein two R$^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^7$ is independently selected from the group consisting of:
(1) hydrogen, and
(2) $C_{1-8}$ alkyl, wherein alkyl is unsubstituted or substituted with one to three groups independently selected from halogen, $C_{1-4}$ alkyl, hydroxy, and $C_{1-4}$ alkoxy;

each $R^8$ is independently selected from the group consisting of:
(1) $C_{1-6}$alkyl,
(2) —$(CH_2)_n$phenyl,
(3) —$(CH_2)_n$naphthyl,
(4) —$(CH_2)_n$heteroaryl,
(5) —$(CH_2)_nC_{2-7}$heterocycloalkyl,
(6) —$(CH_2)_nC_{3-7}$cycloalkyl,
(7) halogen,
(8) —$OR^5$,
(9) —$(CH_2)_nN(R^5)_2$,
(10) —$(CH_2)_nC\equiv N$,
(11) —$(CH_2)_nCO_2R^5$,
(12) —$NO_2$,
(13) —$(CH_2)_nNR^5S(O)_pR^5$
(14) —$(CH_2)_nS(O)_pN(R^5)_2$,
(15) —$(CH_2)_nS(O)_pR^5$,
(16) —$(CH_2)_nNR^5C(O)N(R^5)_2$,
(17) —$(CH_2)_nC(O)N(R^5)_2$,
(18) —$(CH_2)_nNR^5C(O)R^5$,
(19) —$(CH_2)_nNR^5CO_2R^5$,
(20) —$(CH_2)_nNR^5C(O)$-heteroaryl,
(21) —$(CH_2)_nC(O)NR^5N(R^5)_2$,
(22) —$(CH_2)_nC(O)NR^5NR^5C(O)R^5$,
(23) —$O(CH_2)_nC(O)N(R^5)_2$,
(24) —$CF_3$,
(25) —$CH_2CF_3$,
(26) —$OCF_3$, and
(27) —$OCH_2CF_3$;

wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy;

each $R^9$ is independently selected from the group consisting of:
(1) hydrogen,
(2) —OH,
(3) $C_{1-8}$alkyl,
(4) —$OC_{1-8}$alkyl,
(5) halogen;
(6) —$NR^5$,
(7) —$SR^5$, and
(8) —$CF_3$, wherein two $C_{1-8}$alkyl substituents along with the atoms to which they are attached can form a 4- to 8-membered ring;

r is 1 or 2;

s is 1 or 2;

n is 0, 1, 2, or 3; and p is 0, 1, or 2.

In yet a further embodiment of the compounds of the present invention, there are provided compounds of structural formula IIIa or IIIb of the indicated relative stereochemical configurations having the trans orientation of the phenyl and piperidinecarbonyl substituents:

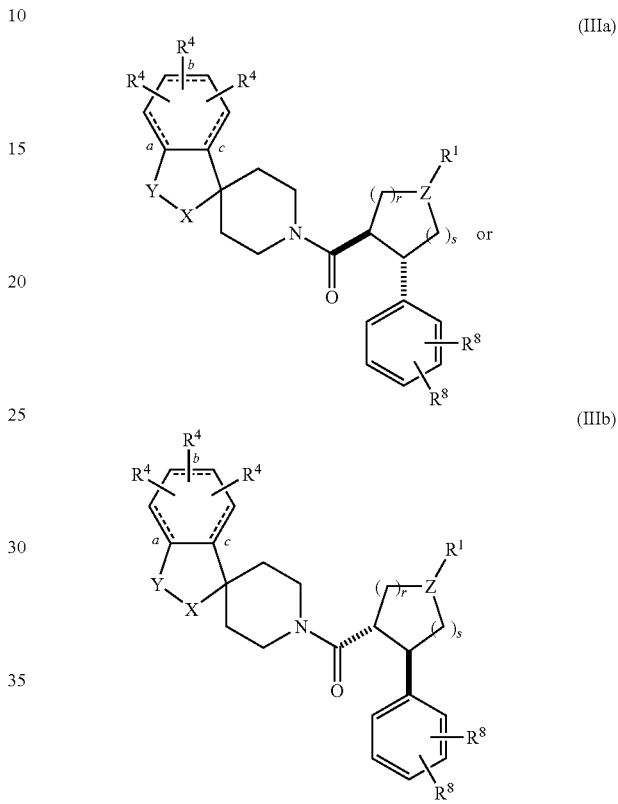

or a pharmaceutically acceptable salt thereof; wherein a, b and c are all single bonds or all double bonds;

Y is selected from the group consisting of:
(1) —$C(R^7)(R^6)$, and
(2) —$N(R^6)$, X is selected from the group consisting of:
(1) $CH_2$,
(2) $C(O)$,
(3) oxygen,
(4) sulfur,
(5) $S(O)$, and
(6) $S(O)_2$;

Z is selected from the group consisting of:
(1) CH, and
(2) N;

$R^1$ is selected from the group consisting of:
(1) —$(CH_2)_nC_{2-7}$heterocycloalkyl, and
(2) —$N(R^7)C_{2-7}$heterocycloalkyl, wherein heterocycloalkyl, and $(CH_2)_n$ are unsubstituted or substituted with one to three groups independently selected from $R^3$ and oxo;

each $R^3$ is independently selected from the group consisting of:
- (1) $C_{1-8}$ alkyl,
- (2) —$(CH_2)_n$phenyl,
- (3) —$(CH_2)_n$naphthyl,
- (4) —$(CH_2)_n$heteroaryl,
- (5) —$(CH_2)_n C_{2-7}$heterocycloalkyl,
- (6) —$(CH_2)_n C_{3-7}$cycloalkyl,
- (7) halogen,
- (8) —$OR^5$,
- (9) —$(CH_2)_n N(R^5)_2$,
- (10) —$(CH_2)_n C\equiv N$,
- (11) —$(CH_2)_n C(O)OR^5$,
- (12) —$(CH_2)_n OC(O)R^5$,
- (13) —$NO_2$,
- (14) —$(CH_2)_n NR^5 S(O)_p R^5$,
- (15) —$(CH_2)_n N(S(O)_p R^5)_2$,
- (16) —$(CH_2)_n S(O)_p N(R^5)_2$,
- (17) —$(CH_2)_n S(O)_p R^5$,
- (18) —$(CH_2)_n NR^5 C(O)N(R^5)_2$,
- (19) —$(CH_2)_n C(O)N(R^5)_2$,
- (20) —$(CH_2)_n NR^5 C(O)R^5$,
- (21) —$(CH_2)_n NR^5 CO_2 R^5$,
- (22) —$(CH_2)_n NR^5 C(O)$-heteroaryl,
- (23) —$(CH_2)_n NR^5 C(O)NR^5 N(R^5)_2$,
- (24) —$(CH_2)_n C(O)NR^5 NR^5 C(O)R^5$,
- (25) —$O(CH_2)_n C(O)N(R^5)_2$,
- (26) —$CF_3$,
- (27) —$CH_2 CF_3$,
- (28) —$OCF_3$, and
- (29) —$OCH_2 CF_3$;

wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

each $R^4$ is independently selected from the group consisting of:
- (1) hydrogen,
- (2) $C_{1-8}$ alkyl,
- (3) halogen,
- (4) —$OR^5$,
- (5) —$(CH_2)_n N(R^5)_2$,
- (6) —$(CH_2)_n C\equiv N$,
- (7) —$NO_2$, and
- (8) —$CF_3$, wherein alkyl and ($CH_2$) are unsubstituted or substituted with one to three substituents independently selected from halogen, hydroxy, oxo, $C_{1-4}$ alkyl, trifluoromethyl, and $C_{1-4}$ alkoxy;

each $R^5$ is independently selected from the group consisting of:
- (1) hydrogen,
- (2) $C_{1-8}$alkyl,
- (3) —$(CH_2)_n C_{3-7}$cycloalkyl,
- (4) —$(CH_2)_n C_{2-7}$heterocycloalkyl,
- (5) —$(CH_2)_n$phenyl,
- (6) —$(CH_2)_n$naphthyl,
- (7) —$(CH_2)_n$heteroaryl, and
- (8) —$(CH_2)_n C_{3-7}$ bicycloalkyl;

wherein allyl, phenyl, heteroaryl, heterocycloalkyl, naphthyl, cycloalkyl, bicycloalkyl and ($CH_2$) are unsubstituted or substituted with one to three groups independently selected from halogen, $C_{1-4}$ alkyl, hydroxy, and $C_{1-4}$ alkoxy, or wherein two $R^5$ groups together with the atom to which they are attached form a 4- to 8-membered mono- or bicyclic ring system optionally containing an additional heteroatom selected from O, S, and —$NC_{1-4}$ alkyl;

each $R^6$ is independently selected from the group consisting of:
- (1) $C_{1-6}$ alkyl,
- (2) —$(CH_2)_n$heteroaryl,
- (3) —$(CH_2)_n C(O)(CH_2)_n N(R^5)_2$,
- (4) —$(CH_2)_n C(O)(CH_2)_n NR^7 R^8$,
- (5) —$(CH_2)_n CN$,
- (6) —$(CH_2)_n N(R^5)_2$,
- (7) —$(CH_2)_n N(R^5)C(O)R^5$,
- (8) —$(CH_2)_n N(R^5)C(O)OR^5$,
- (9) —$(CH_2)_n N(R^5)$—$S(O)$—$C_{1-8}$ alkyl, and
- (10) —$(CH_2)_n N(R^5)$—$S(O)_2$—$C_{1-8}$ alkyl, wherein heteroaryl is unsubstituted or substituted with one to three groups independently selected from $R^3$, and wherein alkyl is unsubstituted or substituted with one to three groups independently selected from $R^3$ and oxo, and wherein any methylene ($CH_2$) in $R^6$ is unsubstituted or substituted with one to two groups independently selected from halogen, hydroxy, and $C_{1-4}$ alkyl; or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^7$ is independently selected from the group consisting of:
- (1) hydrogen, and
- (2) $C_{1-8}$ alkyl, wherein alkyl is unsubstituted or substituted with one to three groups independently selected from halogen, $C_{1-4}$ alkyl, hydroxy, and $C_{1-4}$ alkoxy;

each $R^8$ is independently selected from the group consisting of:
- (1) $C_{1-6}$ alkyl,
- (2) —$(CH_2)_n$-heteroaryl,
- (3) halogen,
- (4) —$OR^5$,
- (5) —$NO_2$,
- (6) —$SR^5$, and
- (7) $CF_3$, wherein heteroaryl is unsubstituted or substituted with one to three substituents independently selected from halogen, hydroxy, $C_{1-4}$ alkyl, trifluoromethyl, and $C_{1-4}$ alkoxy, and wherein alkyl and $(CH_2)_n$ are unsubstituted or substituted with one to three substituents independently selected from halogen, hydroxy, oxo, $C_{1-4}$ alkyl, trifluoromethyl, and $C_{1-4}$ alkoxy;

r is 1 or 2;

s is 1 or 2;

n is 0, 1, 2, or 3; and p is 0, 1, or 2.

In one class of the embodiments of the present invention, a, b and c are single bonds. In another class of the embodiment of the present invention, a, b and c are double bonds.

In another class of the embodiments of the present invention, X is independently selected from the group consisting of: $CH_2$, $C(O)$, oxygen, sulfur, $S(O)$, and $S(O)_2$. In a subclass of this class, X is independently selected from the group consisting of: $CH_2$, $C(O)$, and oxygen. In a subclass of this subclass, X is oxygen. In another subclass of this subclass, X is $CH_2$. In another subclass of this subclass, X is $C(O)$.

In another class of the embodiments of the present invention, Y is independently selected from the group consisting of: $—C(R^7)(R^6)$ and $—N(R^6)$. In a subclass of this class, Y is $—C(R^7)(R^6)$. In a subclass of this subclass, Y is $—C(R^7)(R^6)$ and X is $—CH_2$ or oxygen. In another subclass of this class, Y is $—NR^6$. In a subclass of this subclass, Y is $—N(R^6)$ and X is $C(O)$.

In another class of the embodiments of the present invention, Z is CH. In a subclass of this class, Z is CH and $R^1$ is $—NR^7C_{2-7}$heterocycloalkyl. In another subclass of this class, Z is CH and $R^1$ is $—C_{2-7}$heterocycloalkyl. In another class of the embodiments of the present invention, Z is N. In a subclass of this class, Z is N and $R^1$ is $—(CH_2)_nC_{2-7}$heterocycloalkyl. In a subclass of this subclass, Z is N and $R^1$ is $—C_{2-7}$heterocycloalkyl.

In another class of the embodiments of the present invention, $R^1$ is selected from the group consisting of $—(CH_2)_nC_{2-7}$heterocycloalkyl and $—N(R^7)C_{2-7}$heterocycloalkyl, wherein heterocycloalkyl is unsubstituted or substituted with one to three groups independently selected from $R^3$ and oxo. In a subclass of this class, $R^1$ is $—N(R^7)C_{2-7}$heterocycloalkyl. In another subclass of this subclass, $R^1$ is $—N(R^7)C_{2-7}$heterocycloalkyl and Z is $—CH$. In another subclass of this class, $R^1$ is $—(CH_2)_nC_{2-7}$heterocycloalkyl. In a subclass of this subclass, $R^1$ is $—C_{2-7}$heterocycloalkyl and Z is N or CH.

In another class of the embodiments of the present invention, $R^2$ is phenyl unsubstituted or substituted with one to three groups independently selected from $R^8$. In a subclass of this class, $R^2$ is phenyl substituted with one to three groups selected from $C_{1-4}$alkyl and halogen. In another subclass of this class, $R^2$ is phenyl substituted with one to three halogen groups.

In another class of the embodiments of the present invention, $R^3$ is selected from the group consisting of: hydrogen, $C_{1-8}$ alkyl, and halogen, wherein alkyl is unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group. In a subclass of this class, $R^3$ is methyl.

In another class of the embodiments of the present invention, $R^4$ is selected from the group consisting of: hydrogen, $C_{1-8}$ alkyl, halogen, $OR^5$, $—(CH_2)_nN(R^5)_2$, $—(CH_2)_nC≡N$, $—(CH_2)_nC(O)R^5$, $—(CH_2)_nC(O)OR^5$, $—(CH_2)_nOC(O)R^5$, $NO_2$, $CF_3$, $CH_2CF_3$, $OCF_3$, and $OCH_2CF_3$; wherein alkyl and ($CH_2$) are unsubstituted or substituted with one to three substituents independently selected from halogen, hydroxy, oxo, $C_{1-4}$ alkyl, trifluoromethyl, and $C_{1-4}$ alkoxy. In a subclass of this class, $R^4$ is selected from the group consisting of: hydrogen, $C_{1-8}$ alkyl, and halogen, wherein alkyl is unsubstituted or substituted with one to three substituents independently selected from halogen, hydroxy, oxo, $C_{1-4}$ alkyl, trifluoromethyl, and $C_{1-4}$ alkoxy. In a subclass of this subclass, $R^4$ is methyl or chloride.

In another class of the embodiments of the present invention, $R^6$ is independently selected from the group consisting of: $C_{1-6}$ alkyl, $—(CH_2)_n$-heteroaryl, $—(CH_2)_nC(O)(CH_2)_nN(R^5)_2$, $—(CH_2)_nC(O)(CH_2)_nNR^7R^8$, $—(CH_2)_nCN$, $—(CH_2)_nN(R^5)_2$, $—(CH_2)_nN(R^5)C(O)R^5$, $—(CH_2)_nN(R^5)C(O)OR^5$, $(CH_2)_nN(R^5)—S(O)—C_{1-8}$ alkyl, and $—(CH_2)_nN(R^5)—S(O)_2—C_{1-8}$ alkyl, wherein heteroaryl is unsubstituted or substituted with one to three groups independently selected from $R^3$, and wherein alkyl is unsubstituted or substituted with one to three groups independently selected from $R^3$ and oxo, and wherein any methylene ($CH_2$) in $R^6$ is unsubstituted or substituted with one to two groups independently selected from halogen, hydroxy, and $C_{1-4}$ alkyl; or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo. In a subclass of this class, $R^6$ is independently selected from the group consisting of: $C_{1-6}$ alkyl, $—(CH_2)_nCN$, and $—(CH_2)_nN(R^5)C(O)R^5$, wherein alkyl is unsubstituted or substituted with one to three groups independently selected from $R^3$ and oxo, and wherein any methylene ($CH_2$) in $R^6$ is unsubstituted or substituted with one to two groups independently selected from halogen, hydroxy, and $C_{1-4}$ alkyl; or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo.

In another class of the embodiments of the present invention, $R^8$ is independently selected from the group consisting of: $C_{1-6}$ alkyl, -heteroaryl, halogen, $OR^5$, $NO_2$, $—SR^5$, and $CF_3$. In a subclass of this class, $R^8$ is independently selected from the group consisting of: $C_{1-6}$ alkyl, and halogen. In a subclass of this subclass, $R^8$ is halogen. In another subclass of this subclass, $R^8$ is fluoro or chloro. In another subclass of this subclass, $R^8$ is fluoro.

In another class of the embodiments of the present invention, $R^9$ is independently selected from the group consisting of: $C_{1-6}$ alkyl, and hydrogen, wherein two $C_{1-6}$alkyl substituents along with the atoms to which they are attached can form a 4- to 8-membered ring. In a subclass of this class, $R^9$ methyl. In another subclass of this class, $R^9$ is hydrogen.

In another class of the embodiments of the present invention, r is 1 and s is 1. In another class of the embodiments of the present invention, r is 2 and s is 1.

In another class of the embodiments of the present invention, n is 0, 1, and 2. In a subclass of this class, p is 2. In another subclass of this class, p is 0.

In further embodiments of the compounds of structural formula I, there are provided compounds of structural formula IV, V, VI and VII:

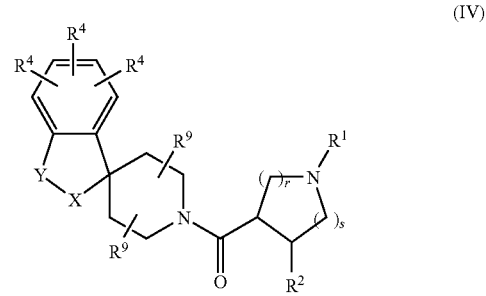

(IV)

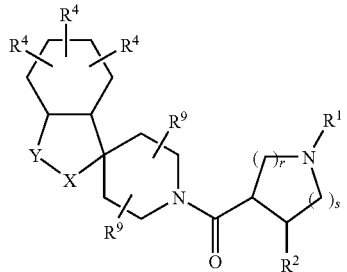
(V)
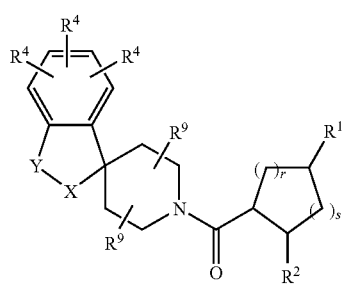
(VI)
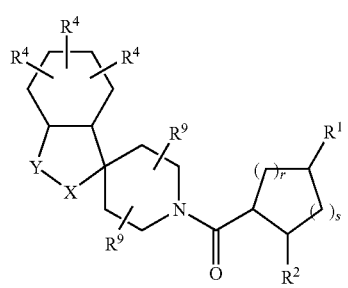
(VII)
Illustrative but nonlimiting examples of compounds of the present invention that are useful as melanocortin-4 receptor agonists are the following:
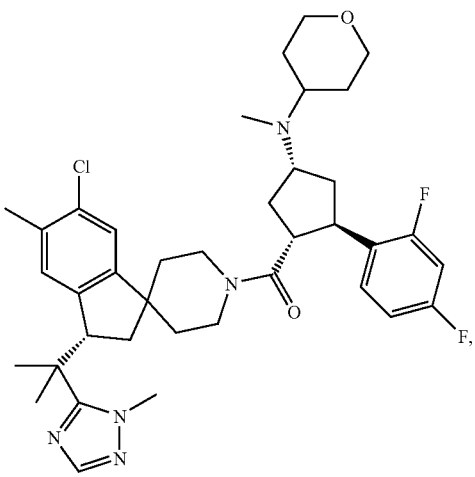
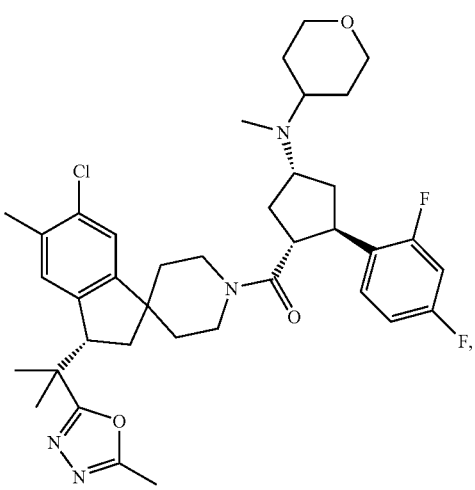
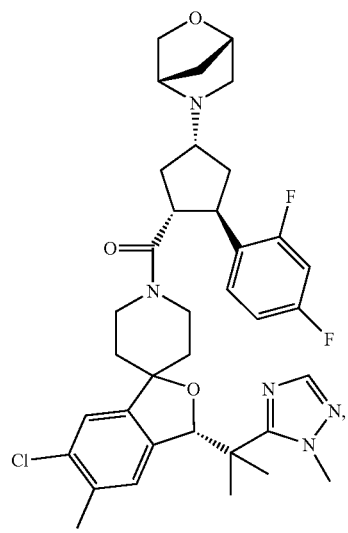
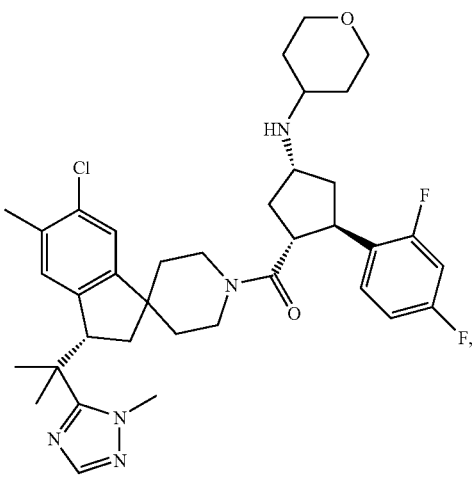

-continued

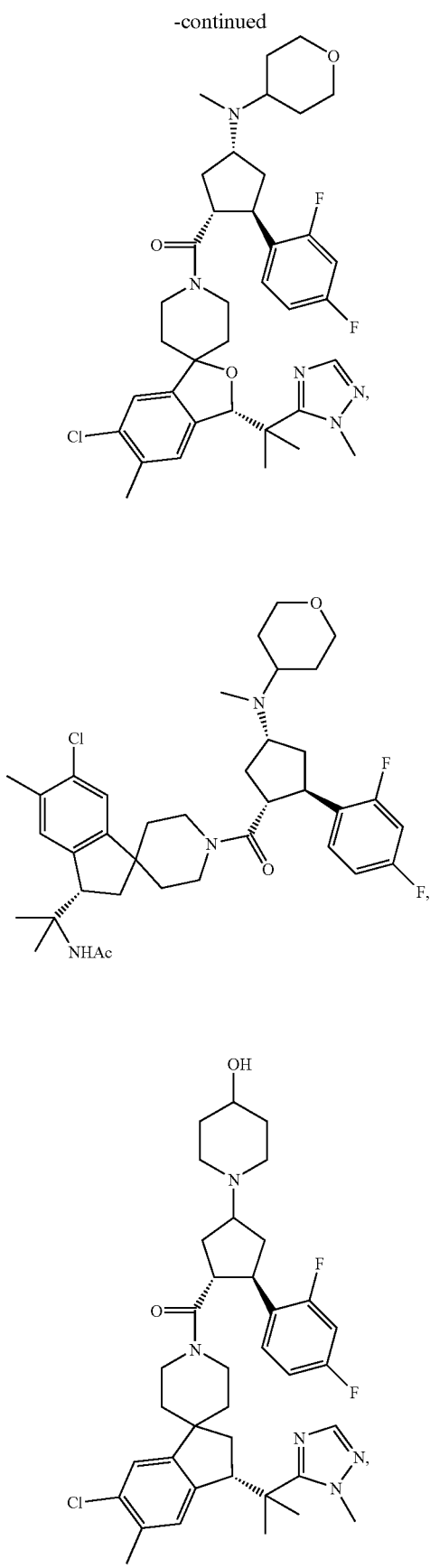

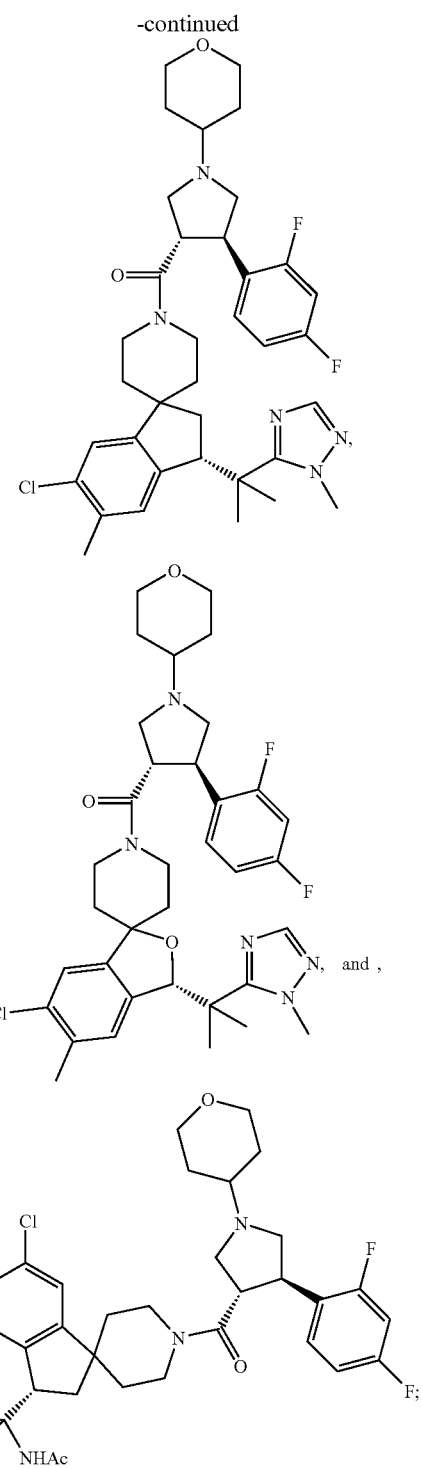

or a pharmaceutically acceptable salt thereof.

The compounds of structural formula I are effective as melanocortin receptor ligands and are particularly effective as selective ligands of the melanocortin-4 receptor. They are therefore useful for the treatment and/or prevention of disorders responsive to the modulation of the melanocortin-4 receptor, such as obesity, diabetes, obesity-related disorders, nicotine addiction, alcoholism, as well as male and female sexual dysfunction, and in particular male erectile dysfunction, cachexia, wasting, anorexia and weight loss.

More particularly, the selective melanocortin-4 receptor (MC-4R) agonists of formula I are useful for the treatment of disorders responsive to the activation of the melancortin-4 receptor, such as obesity, diabetes, nicotine addiction, alcoholism, male sexual dysfunction, and female sexual dysfunction. Another aspect of the present invention provides a method for the treatment or prevention of disorders, diseases or conditions responsive to the modulation of the melanocortin-4 receptor in a subject in need thereof which comprises administering to the subject a therapeutically or prophylactically effective amount of a compound according to claim 1, or a pharmaceutically acceptable salt thereof.

Furthermore, the selective melanocortin-4 receptor (MC-4R) antagonists of formula I are useful for the treatment of disorders responsive to the deactivation of the melanocortin-4 receptor, such as cachexia, wasting, anorexia, frailty, sarcopenia and weight loss.

Another aspect of the present invention provides a method for the treatment or prevention of obesity, diabetes, or an obesity related disorder in a subject in need thereof which comprises administering to said subject a therapeutically or prophylactically effective amount of a melanocortin-4 receptor agonist of the present invention. Another aspect of the present invention provides a method for the treatment or prevention of obesity in a subject in need thereof which comprises administering to the subject a therapeutically or prophylactically effective amount of a compound according to claim 1, or a pharmaceutically acceptable salt thereof. Another aspect of the present invention provides a method for the treatment or prevention of diabetes mellitus in a subject in need thereof comprising administering to the subject a therapeutically or prophylactically effective amount of a compound according to claim 1, or a pharmaceutically acceptable salt thereof. Another aspect of the present invention provides a method for the treatment or prevention of an obesity-related disorder selected from the group consisting of overeating, binge eating, and bulimia, hypertension, elevated plasma insulin concentrations, insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, metabolic syndrome, insulin resistance syndrome, sexual and reproductive dysfunction, infertility, hypogonadism, hirsutism, obesity-related gastro-esophageal reflux, Pickwickian syndrome, cardiovascular disorders, inflammation, systemic inflammation of the vasculature, arteriosclerosis, hypercholesterolemia, hyperuricaemia, lower back pain, gallbladder disease, gout, and kidney cancer, cardiac hypertrophy, left ventricular hypertrophy, nicotine addiction and alcoholism, in a subject in need thereof which comprises administering to the subject a therapeutically or prophylactically effective amount of a compound according to claim 1, or a pharmaceutically acceptable salt thereof.

The present invention also relates to methods for treating or preventing obesity by administering the melanocortin-4 receptor agonist of the present invention in combination with a therapeutically or prophylactically effective amount of another agent known to be useful to treat or prevent the condition.

The present invention also relates to methods for treating or preventing diabetes by administering the melanocortin-4 receptor agonist of the present invention in combination with a therapeutically or prophylactically effective amount of another agent known to be useful to treat or prevent the condition.

Another aspect of the present invention provides a method for the treatment or prevention of female or male sexual dysfunction, including male erectile dysfunction, which comprises administering to a subject in need of such treatment or prevention a therapeutically or prophylactically effective amount of a melanocortin-4 receptor agonist of the present invention. Another aspect of the present invention provides a method for the treatment or prevention of erectile dysfunction in a subject in need thereof comprising administering to the subject a therapeutically or prophylactically effective amount of a compound according to claim 1, or a pharmaceutically acceptable salt thereof. The present invention also relates to methods for treating or preventing erectile dysfunction by administering the melanocortin-4 receptor agonist of the present invention in combination with a therapeutically or prophylactically effective amount of another agent known to be useful to treat the condition.

Another aspect of the present invention provides a method for the treatment or prevention of alcoholism which comprises administering to a subject in need of such treatment or prevention a therapeutically or prophylactically effective amount of a melanocortin 4 receptor agonist of the present invention. The present invention also provides a method for reducing alcohol consumption which comprises administering to a subject in need of such treatment or prevention a therapeutically or prophylactically effective amount of a melanocortin 4 receptor agonist of the present invention.

Another aspect of the present invention provides a method for the treatment or prevention of nicotine addiction which comprises administering to a subject in need of such treatment or prevention a therapeutically or prophylactically effective amount of a melanocortin 4 receptor agonist of the present invention. The present invention also provides a method for reducing nicotine consumption which comprises administering to a subject in need of such treatment a therapeutically effective amount of a melanocortin 4 receptor agonist of the present invention. Yet another aspect of the present invention provides a method for the treatment or prevention of substance addiction which comprises administering to a subject in need of such treatment or prevention a therapeutically or prophylactically effective amount of a melanocortin 4 receptor agonist of the present invention.

Yet another aspect of the present invention provides a method for the treatment or prevention of cachexia which comprises administering to a subject in need of such treatment or prevention a therapeutically or prophylactically effective amount of a melanocortin 4 receptor antagonist of the present invention. The present invention also provides a method for the treatment or prevention of anorexia, wasting or weight loss which comprises administering to a subject in need of such treatment or prevention a therapeutically or prophylactically effective amount of a melanocortin 4 receptor antagonist of the present invention.

Another aspect of the present invention provides a pharmaceutical composition comprising a compound of structural formula I and a pharmaceutically acceptable carrier.

Yet another aspect of the present invention relates to the use of a compound of structural formula I for the manufacture of a medicament useful for the treatment or prevention, or suppression of a disease mediated by the melanocortin-4 receptor in a subject in need thereof.

Yet another aspect of the present invention relates to the use of a melanocortin-4 agonist of the present invention for the manufacture of a medicament useful for the treatment or prevention, or suppression of a disease mediated by the melanocortin-4 receptor, wherein the disease is selected from the group consisting of obesity, diabetes and an obesity-related disorder in a subject in need thereof.

Yet another aspect of the present invention relates to the use of a melanocortin-4 agonist of the present invention for the manufacture of a medicament useful for the treatment or prevention, or suppression of male and female sexual dysfunction, and male erectile dysfunction in a subject in need thereof.

Yet another aspect of the present invention relates to the use of a selective melanocortin-4 agonist of the present invention in the preparation of a medicament useful for treating or preventing alcoholism in a subject in need thereof. The present invention also relates to the use of a selective melanocortin-4 agonist of the present invention in the preparation of a medicament useful for reducing alcohol consumption in a subject in need thereof.

Yet another aspect of the present invention relates to the use of a selective melanocortin 4 receptor agonist of the present invention in the preparation of a medicament useful to treat or prevent nicotine addiction in a subject in need thereof. The present invention also relates to the use of a selective melanocortin 4 receptor agonist of the present invention in the preparation of a medicament useful to reduce nicotine consumption in a subject 1 in need thereof.

Yet another aspect of the present invention relates to the use of a selective melanocortin 4 receptor agonist of the present invention in the preparation of a medicament useful to treat substance addiction in a subject in need thereof.

Yet another aspect of the present invention relates to the use of a selective melanocortin 4 receptor antagonist of the present invention in the preparation of a medicament useful treat or prevent cachexia in a subject in need thereof. The present invention also relates to the use of a selective melanocortin 4 receptor antagonist of the present invention in the preparation of a medicament useful treat or prevent anorexia, wasting, frailty, sarcopenia, or weight loss in a subject in need thereof.

Yet another aspect of the present invention relates to the use of a therapeutically effective amount of a melanocortin-4 receptor agonist of formula I, or a pharmaceutically acceptable salt thereof, and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, a ghrelin receptor antagonist, and a NK-1 antagonist, or a pharmaceutically acceptable salt thereof, for the manufacture of a medicament useful for the treatment, control, or prevention of obesity, diabetes or an obesity-related disorder in a subject in need of such treatment. Yet another aspect of the present invention relates to the use of a therapeutically effective amount of a melanocortin-4 receptor agonist of formula I, and pharmaceutically acceptable salts and esters thereof, and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, a ghrelin receptor antagonist, and a NK-1 antagonist, or a pharmaceutically acceptable salt thereof, for the manufacture of a medicament for treatment or prevention of obesity, diabetes or an obesity-related disorder which comprises an effective amount of a melanocortin-4 receptor agonist of formula I and an effective amount of the agent, together or separately. Yet another aspect of the present invention relates to a product containing a therapeutically effective amount of a melanocortin-4 receptor agonist of formula I, or a pharmaceutically acceptable salt thereof, and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, a ghrelin receptor antagonist, and a NK-1 antagonist, or a pharmaceutically acceptable salt thereof, as a combined preparation for simultaneous, separate or sequential use in obesity, diabetes, or an obesity-related disorder.

Yet another aspect of the present invention relates to the use of a therapeutically effective amount of a melanocortin-4 receptor agonist of formula I, or a pharmaceutically acceptable salt thereof, and a therapeutically effective amount of an agent selected from the group consisting of: a type V cyclic-GMP-selective phosphodiesterase inhibitor, an $\alpha_2$-adrenergic receptor antagonist, and a dopaminergic agent, or a pharmaceutically acceptable salt thereof, for the manufacture of a medicament useful for the treatment, control, or prevention of male erectile dysfunction in a subject in need of such treatment. Yet another aspect of the present invention relates to the use of a therapeutically effective amount of a melanocortin-4 receptor agonist of formula I, or a pharmaceutically acceptable salt thereof; and a therapeutically effective amount of an agent selected from the group consisting of a type V cyclic-GMP-selective phosphodiesterase inhibitor, an $\alpha_2$-adrenergic receptor antagonist, and a dopaminergic agent, and pharmaceutically acceptable salts and esters thereof, for the manufacture of a medicament for treatment or prevention of male erectile dysfunction which comprises an effective amount of a compound of formula I and an effective amount of the agent, together or separately. Yet another aspect of the present invention relates to a product containing a therapeutically effective amount of a melanocortin-4 receptor agonist of formula I, or a pharmaceutically acceptable salt thereof; and a therapeutically effective amount of an agent selected from the group consisting of a type V cyclic-GMP-selective phosphodiesterase inhibitor, an $\alpha_2$-adrenergic receptor antagonist, and a dopaminergic agent, and pharmaceutically acceptable salts and esters thereof; as a combined preparation for simultaneous, separate or sequential use in male erectile dysfunction.

Melanocortin receptor agonist compounds can be provided in kit. Such a kit typically contains an active compound in dosage forms for administration. A dosage form contains a sufficient amount of active compound such that a beneficial effect can be obtained when administered to a patient during regular intervals, such as 1, 2, 3, 4, 5 or 6 times a day, during the course of 1 or more days. Preferably, a kit contains instructions indicating the use of the dosage form for weight reduction (e.g., to treat obesity) and the amount of dosage form to be taken over a specified time period.

Throughout the instant application, the following terms have the indicated meanings:

The term "alkyl", as well as other groups having the prefix "alk", such as alkoxy, alkanoyl, means carbon chains of the designated length which may be in a straight or branched configuration, or combinations thereof. The term alkyl also includes methylene groups which are designated as ($CH_2$) herein. Examples of alkyl groups include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethyl butyl, 1,2-dimethylbutyl, 1,3-dimethylbutyl, 2,2-dimethylbutyl, 2,3-dimethylbutyl, 3,3-dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl. 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, and the like.

The term "halogen" is intended to include the halogen atoms fluorine, chlorine, bromine and iodine.

The term "$C_{1-4}$ alkyliminoyl" means $C_{1-3}$alkylC(=NH)—.

The term "aryl" includes phenyl and naphthyl.

The term "heteroaryl" includes mono- and bicyclic aromatic rings containing from 1 to 4 heteroatoms selected from nitrogen, oxygen and sulfur. Examples thereof include, but are not limited to, pyridinyl, furyl, thienyl, pyrrolyl, oxazolyl, thiazolyl, triazolyl, triazinyl, tetrazolyl, thiadiazolyl, imidazolyl, isoxazolyl, isothiazolyl, oxadiazolyl, pyrazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, and the like.

In one embodiment of the present invention, heteroaryl is selected from the group consisting of pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, isoquinolyl, benzimidazolyl, benzofuryl, benzothienyl, indolyl, benzthiazolyl, and benzoxazolyl.

Bicyclic heteroaromatic rings include, but are not limited to, benzothiadiazole, indole, benzothiophene, benzofuran, benzimidazole, benzisoxazole, benzothiazole, quinoline, quinazoline, benzotriazole, benzoxazole, isoquinoline, purine, furopyridine, thienopyridine, benzisodiazole, triazolopyrimidine, and 5,6,7,8-tetrahydroquinoline.

The term "cycloalkyl" includes mono- or bicyclic non-aromatic rings containing only carbon atoms. Examples of cycloalkyl include, but are not limited to, cyclopropyl, cyclobutyl, cyclopentyl, cyclohexyl, cycloheptyl.

The term "heterocycloalkyl" includes two to ten carbon mono- or bicyclic ring systems with at least one non-aromatic heterocyclic ring containing one to four heteroatoms selected from nitrogen, oxygen, sulfur, sulfone, and sulfoxide. The heterocycloalkyl ring and bicyclic ring system may be unsubstituted or substituted with 1 or 2 substituents on any carbon and 0-1 substituent on any nitrogen. Examples of heterocycloalkyls include, but are not limited to, azetidine, piperidine, morpholine, thiamorpholine, tetrahydropyran, thiatetrahydropyran, pyrrolidine, imidazolidine, tetrahydrofuran, piperazine, 1-thia-4-aza-cyclohexane, and aza-bicyclo[2.2.1]heptane.

Certain of the above defined terms may occur more than once in the above formula and upon such occurrence each term shall be defined independently of the other; thus for example, $NR^4R^4$ may represent $NH_2$, $NHCH_3$, $N(CH_3)CH_2CH_3$, and the like.

The term "subject" means a mammal. One embodiment of the term "mammal" is a "human," said human being either male or female. The instant compounds are also useful for treating or preventing obesity and obesity related disorders in cats and dogs. As such, the term "mammal" includes companion animals such as cats and dogs. The term "mammal in need thereof" refers to a mammal who is in need of treatment or prophylaxis as determined by a researcher, veterinarian, medical doctor or other clinician.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By a melanocortin receptor "agonist" is meant an endogenous or drug substance or compound that can interact with a melanocortin receptor and initiate a pharmacological or biochemical response characteristic of melanocortin receptor activation. By a melanocortin receptor "antagonist" is meant a drug or a compound that inhibits the melanocortin receptor-associated responses induced by an agonist. The "agonistic" and "antagonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the present instance, the ability of a compound of structural formula I to bind to a melanocortin receptor. Binding affinities for the compounds of the present invention were measured in the binding assay described below and are expressed as $IC_{50}$'s.

"Efficacy" describes the relative intensity of response which different agonists produce even when they occupy the same number of receptors and with the same affinity. Efficacy is the property that describes the magnitude of response. Properties of compounds can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Compounds of structural formula I contain one or more asymmetric centers and can thus occur as racemates and racemic mixtures, single enantiomers, diastereomeric mixtures and individual diastereomers. The present invention is meant to comprehend all such isomeric forms of the compounds of structural formula I, including the E and Z geometric isomers of olefinic double bonds. Some of the compounds described herein may exist as tautomers such as keto-enol tautomers. The individual tautomers as well as mixtures thereof are encompassed within the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formula I, IIa, IIb, IIIa, IIIb, IV, V, VI and VII may be obtained by stereospecific synthesis using optically pure starting materials or reagents of known absolute configuration.

It will be understood that the compounds of the present invention include hydrates, solvates, polymorphs, crystalline, hydrated crystalline and amorphous forms of the compounds of the present invention, and pharmaceutically acceptable salts thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, TEA, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts, such as the hydrochloride salts.

Compounds of formula I are melanocortin receptor ligands and as such are useful in the treatment, control or prevention of diseases, disorders or conditions responsive to the modulation of one or more of the melanocortin receptors including, but are not limited to, MC-1, MC-2, MC-3, MC-4, or MC-5.

In particular, the compounds of formula I act as melanocortin-4 receptor agonists and antagonists useful in the treatment, control or prevention of diseases, disorders or conditions responsive to the activation or deactivation of the melanocortin-4 receptor. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including male impotence, loss of libido, female sexual arousal dysfunction, female orgasmic dysfunction, hypoactive sexual desire disorder, sexual pain disorder and male erectile dysfunction), fever, inflammation, immunemodulation, rheumatoid arthritis, skin tanning, acne and other skin disorders, neuroprotective and cognitive and memory enhancement including the treatment of Alzheimer's disease. Some agonists encompassed by formula I show highly selective affinity for the melanocortin-4 receptor (MC-4R) relative to MC-1R, MC-2R, MC-3R, and MC-5R, which makes them especially useful in the prevention and treatment of obesity, female sexual dysfunction, male sexual dysfunction including erectile dysfunction, alcoholism and nicotine addiction. Some antagonists encompassed by formula I show highly selective affinity for the melanocortin-4 receptor (MC-4R) relative to MC-1R, MC-2R, MC-3R, and MC-5R, which makes them especially useful in the prevention and treatment of cachexia, wasting and anorexia.

The compositions of the present invention are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating, binge eating, and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer, nicotine addiction, substance addiction and alcoholism. The compositions of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (ATP-M). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of treatment may be decreasing plasma triglycerides in a subject with elevated plasma triglycerides. Another outcome of treatment may be lowering LDL cholesterol in a subject with high LDL cholesterol levels. Another outcome of treatment may be increasing HDL cholesterol in a subject with low HDL cholesterol levels. Another outcome may be decreasing the LDL/HDL ratio in a subject in need thereof. Another outcome of treatment may be increasing insulin sensitivity. Another outcome of treatment may be enhancing glucose tolerance in a subject with glucose intolerance. Another outcome of treatment may be decreasing insulin resistance in a subject with increased insulin resistance or elevated levels of insulin. Another outcome may be decreasing triglycerides in a subject with elevated triglycerides. Yet another outcome may be improving LDL cholesterol, non-HDL cholesterol, triglyceride, HDL cholesterol or other lipid analyte profiles.

Prevention of diabetes mellitus refers to the administration of a compound or combination of the present invention to prevent the onset of diabetes in a subject at risk thereof.

"Obesity" is a condition in which there is an excess of body fat. The operational definition of obesity is based on the Body Mass Index (BMD), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus-type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, dermatological disorders, hypertension, insulin resistance, hypercholesterolemia, hypertriglyceridemia, and cholelithiasis.

"Male sexual dysfunction" includes impotence, loss of libido, and erectile dysfunction.

"Erectile dysfunction" is a disorder involving the failure of a male subject to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

Treatment of male sexual dysfunction refers to the administration of a compound or combination of the present invention to treat impotence and/or loss of libido, and/or erectile dysfunction in a male subject in need thereof. One outcome of treatment may be a decrease in impotence. Another outcome of treatment may be an increase in libido. Yet another outcome of treatment may be a decrease in the magnitude or frequency of erectile dysfunction. Treatment of male erectile dysfunction refers to the administration of a compound or combination of the present invention to treat one or more of the symptoms of male erectile dysfunction in a male subject in need thereof. One outcome of treatment may be increasing the ability to achieve an erection. Another outcome of treatment may be increasing the ability to maintain an erection. Another outcome of treatment may be reducing ejaculatory failure. Another outcome of treatment may be decreasing premature ejaculation. Yet another outcome of treatment may be increasing the ability to achieve an orgasm. Prevention of male sexual dysfunction and male erectile dysfunction refers to the administration of the compounds or combinations of the present invention to prevent the symptoms of sexual dysfunction and erectile dysfunction in a male subject at risk thereof.

"Female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

The compositions of the present invention are useful for the treatment or prevention of disorders associated with excessive food intake, such as obesity and obesity-related disorders.

"Cachexia" is a wasting disorder that is characterized by weight loss, loss of muscle protein, loss of lean body mass, anorexia, and weakness, and is typically associated with chronic diseases, including cancer cachexia and cachexia associated with AIDS, chronic obstructive pulmonary disease, rheumatiod arthritis, tuberculosis and Crohn's disease. Cancer cachexia is a syndrome of progressive weight loss, anorexia, and persistent erosion of the body in response to a malignant growth; cachexia may be present in early stages of tumor growth before any signs or symptoms of malignancy.

Treatment of cachexia refers to the administration of a compound or combination of the present invention to treat one or more of the symptoms of cachexia in a subject in need thereof.

Prevention of cachexia refers to the administration of the compounds or combinations of the present invention to prevent the symptoms of cachexia or wasting in a subject at risk thereof, including but not limited to, a subject diagnosed with cancer.

The compositions of the present invention are useful for the treatment or prevention of nicotine addiction, substance addiction, and alcoholism, as well as nicotine addiction related disorders, substance abuse related disorders, and alcoholism related disorders.

The term "nicotine" as used herein refers to nicotine contained in tobacco and other naturally occurring sources, as well as synthetic nicotine, and salts thereof, including but not limited to, the salicylate or bitartrate salt thereof. Nicotine addiction is a destructive pattern of nicotine use, leading to significant social occupational, or medical impairment and characterized by three or more of the following symptoms: 1) nicotine tolerance (a need for markedly increased amounts of nicotine to achieve intoxication, or markedly diminished effect with continued use of the same amount of nicotine); 2) nicotine withdrawal symptoms (sweating or rapid pulse, increased hand tremor, insomnia, nausea or vomiting, physical agitation, anxiety, transient visual, tactile, or auditory hallucinations or illusions, grand mal seizures), 3) nicotine administration to relieve or avoid withdrawal symptoms, 4) greater use than nicotine than intended, 5) unsuccessful efforts to cut down or control nicotine use, 6) persistent desire or unsuccessful efforts to cut down or control nicotine use, 7) great deal of time spent using nicotine, 8) nicotine caused reduction in social, occupational or recreational activities, and 9) continued use of nicotine despite knowledge of having a persistent or recurrent physical or psychological problem that is likely to have been worsened by nicotine use. Nicotine addiction-related disorders include, but are not limited to: cancer of the lung, mouth, pharynx, larynx, esophagus, cervix, kidney, ureter and bladder; chronic bronchitis; emphysema; asthma; heart disease, including stroke, heart attack, vascular disease, and aneurysm; premature delivery; spontaneous abortion; and infants with decreased birth weight; as well as nicotine withdrawal symptoms. "Treatment" (of nicotine addiction) refers to the administration of the compounds or combinations of the present invention to reduce or inhibit the use of nicotine by a subject One outcome of treatment may be reducing the use of nicotine in a subject relative to the subject's nicotine use prior to treatment. Another outcome of treatment may be inhibiting the use of nicotine in a subject. Another outcome of treatment may be decreasing the severity of nicotine intake, such as decreasing the amount of nicotine consumed, in a subject. "Prevention" (of nicotine addiction) refers to the administration of the compounds or combinations of the present invention to prevent nicotine abuse, nicotine addiction or developing a nicotine addiction-related disorder in a subject by administration prior to the start of nicotine use. One outcome of prevention may be to prevent nicotine use in a subject by administration prior to the start of nicotine use. Another outcome of prevention may be to prevent nicotine addiction in a subject. Another outcome of prevention may be to prevent the development of a nicotine addiction related disorder in a subject. Another outcome of prevention may be preventing nicotine use from occurring if the treatment is administered prior to the onset of nicotine use in a subject. Another outcome of prevention may be to administer the compounds or combinations of the present invention to prevent nicotine use in a subject at risk of developing nicotine addiction.

Substance addiction includes opiate addiction, cocaine addiction, marijuana addiction, and amphetamine addiction. The term "opiate" as used herein includes, but is not limited to, heroin; narcotics, such as morphine; opium; codeine; oxycodone (Oxycontin®); propoxyphene (Darvon®); hydrocodone (Vicodin®), hydromorphone (Dilaudid®); meperidine (Demerol®), and Lomotil®. The term "amphetamine(s)" as used herein includes, but is not limited to, amphetamine, dextroamphetamine, and methamphetamine. "Treatment" (of substance addiction) refers to the administration of the compounds or combinations of the present invention to reduce or inhibit the use of the substance by a subject. One outcome of treatment may be reducing the use of the substance in a subject relative to the subject's substance use prior to treatment. Another outcome of treatment may be inhibiting the use of the substance in a subject. Another outcome of treatment may be decreasing the occurrence of substance intake in a subject. Another outcome of treatment may be decreasing the severity of substance intake, such as decreasing the amount of the substance consumed, in a subject. Another outcome of treatment may be to administer the compounds or combinations of the present invention to reduce or inhibit the consumption of the substance in a subject in need thereof. "Prevention" (of substance addiction) refers to the administration of the compounds or combinations of the present invention to prevent substance addiction or developing a substance addiction-related disorder in a subject. One outcome of prevention may be to prevent substance use in a subject by administration prior to the start of substance use. Another outcome of prevention may be to prevent substance addiction in a subject. Another outcome of prevention may be to prevent the development of a substance addiction related disorder in a subject. Another outcome of prevention may be preventing substance use from occurring if the treatment is administered prior to the onset of substance use in a subject.

The compounds of the present invention are useful to inhibit or reduce voluntary alcohol consumption, and for the treatment or prevention of alcoholism, alcohol abuse, and alcohol-related disorders. Alcoholism is a disease that is characterized by abnormal alcohol seeking behavior that leads to impaired control over drinking, and may include some or all of the following symptoms: narrowing of drinking repertoire (drinking only one brand or type of alcoholic beverage); craving (a strong need or urge to drink), loss of control (not being able to stop drinking once drinking has begun), drink seeking behavior (attending only social events that include drinking); physical dependence (withdrawal symptoms, such as nausea, sweating, shakiness, and anxiety after cessation of drinking), drinking to relieve or avoid withdrawal symptoms; and tolerance (the need to drink greater amounts of alcohol to achieve previous effects); subjective awareness of the compulsion to drink or craving for alcohol; and relapse (a return to drinking after a period of abstinence). Alcohol related disorders include, but are not limited to: liver disease, such as hepatitis, inflammation of the liver, and alcoholic cirrhosis; heart disease; high blood pressure; stroke; certain forms of cancer, such as esophageal, mouth, throat, voice box, breast, colon and rectal cancer; pancreatitis; alcoholic dementia, Wernicke-Korsakoff syndrome, brain damage, slow bone healing; impaired wound healing; diminished immune defenses; and death. "Treatment" (of alcoholism) refers to the administration of the compounds or combinations of the present invention to reduce or inhibit the consumption of alcohol in a subject. One outcome of treatment may be reducing the consumption of alcohol in a subject relative to the subject's alcohol consumption prior to treatment. Another outcome of treatment may be inhibiting consumption of alcohol in a subject. Another outcome of treatment may be decreasing the occurrence of alcohol intake in a subject. Another outcome of treatment may be decreasing the severity of alcohol intake, such as decreasing the amount of alcohol consumed, in a subject. Another outcome of treatment may be to administer the compounds or combinations of the present invention to reduce or inhibit the consumption of alcohol in a subject in need thereof. "Prevention" (of alcoholism) refers to the administration of the compounds or combinations of the present invention to prevent alcohol intake, alcohol consumption, alcohol abuse, alcoholism or developing an alcohol-related disorder in a subject. One outcome of prevention may be to prevent alcohol intake in a subject by administration prior to the start of alcohol consumption. Another outcome of prevention may be to prevent alcoholism in a subject. Another outcome of prevention may be to administer the compounds or combinations of the present invention to prevent alcohol intake in a subject at risk of alcoholism or developing an alcohol-related disorder in a subject. Moreover, if treatment is commenced in a subject already consuming alcohol, such treatment may prevent the occurrence, progression or severity of alcohol-related disorders.

The terms "administration of" and or "administering" a compound should be understood to mean providing a compound of the invention or a prodrug of a compound of the invention to a subject in need of treatment. The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art. The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder. The therapeutically or prophylactically effective amount, or dosage, of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgement.

Administration and Dose Ranges

Any suitable route of administration may be employed for providing a subject or mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of formula I are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 50 milligram per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

For the treatment of sexual dysfunction compounds of formula I are given in a dose range of 0.001 milligram to about 50 milligram per kilogram of body weight, preferably as a single dose orally or as a nasal spray.

When treating cachexia or weight loss, satisfactory results are obtained when the compounds of formula I are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

In the case where an oral composition is employed, a suitable dosage range is, e.g. from about 0.01 mg to about 1500 mg of a compound of Formula I per day, preferably from about 0.1 mg to about 600 mg per day, more preferably from about 0.1 mg to about 100 mg per day. For oral administration, the compositions are preferably provided in the form of tablets containing from 0.01 to 1,000 mg, preferably 0.01, 0.05, 0.1, 0.5, 1, 2.5, 5, 10, 15, 20, 25, 30, 40, 50, 100, 250, 500, 600, 750, 1000, 1250 or 1500 milligrams of the active ingredient for the symptomatic adjustment of the dosage to the patient to be treated.

For use where a composition for intranasal administration is employed, intranasal formulations for intranasal administration comprising 0.001-10% by weight solutions or suspensions of the compounds of Formula I in an acceptable intranasal formulation may be used.

For use where a composition for intravenous administration is employed, a suitable dosage range is from about 0.001 mg to about 50 mg, preferably from 0.01 mg to about 50 mg, more preferably 0.1 mg to 10 mg, of a compound of Formula I per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compounds of Formula I in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual patient. Such dosage may be ascertained readily by a person skilled in the art.

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Examples of other active ingredients that may be combined with a compound of Formula I for the treatment or prevention of obesity and/or diabetes, either administered separately or in the same pharmaceutical compositions, include, but are not limited to:

(a) insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like), and compounds disclosed in WO 97/10813, WO 97/27857, WO 97/28115, WO 97/28137, and WO 97/27847; (iii) biguanides such as metformin and phenformin;

(b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-$NH_2$);

(c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide;

(d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR14, and the like;

(e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activator receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) anti-oxidants, such as probucol, (vi) vitamin E, and (vii) thyromimetics;

(f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579 by Glaxo;

(g) PPARδ agonists, such as those disclosed in WO97/28149;

(h) PPAR α/δ agonists, such as muraglitazar, and the compounds disclosed in U.S. Pat. No. 6,414,002;

(i) smoking cessation agents, such as a nicotine agonist or a partial nicotine agonist such as varenicline, or a monoamine oxidase inhibitor (MAOI), or another active ingredient demonstrating efficacy in aiding cessation of tobacco consumption; for example, an antidepressant such as bupropion, doxepine, omortriptyline; or an anxiolytic such as buspirone or clonidine; and (i) anti-obesity agents, such as (1) growth hormone secretagogues, growth hormone secretagogue receptor agonists/antagonists, such as NN$_7$O$_3$, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid CB$_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. No. 5,705,515, and U.S. Pat. No. 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan 11 or those described in WO 99/64002 and WO 00/74679; (15) other Mc4r (melanocortin 4 receptor) agonists, such as CHIR86036 (Chiron), ME-10142, and ME-10145 (Melacure), CHIR86036 (Chiron); PT-141, and PT-14 (Palatin), and those disclosed in: U.S. Pat. Nos. 6,410,548; 6,294,534; 6,350,760; 6,458,790; 6,472,398; 6,376,509; and 6,818,658; US Patent Publication No. US2002/0137664; US2003/0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanol]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm.(Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); 26) PDE (phosphodiesterase) inhibitors, such as theophylline, pentoxifylline, zaprinast, sildenafil, aminone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) BRS3 (bombesin receptor subtype 3) agonists such as [D-Phe6,beta-Ala11,Phe13, Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444; and the compounds disclosed in U.S. Pat. No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5,696,093, U.S. Pat. No. 5,936,092, U.S. Pat. No. 6,046,162, U.S. Pat. No. 6,046,167, U.S. Pat. No. 6,093, 692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966, which are incorporated herein by reference; (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (54) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (56) Opioid antagonists such as nalmefene (Revex®), 3-methoxynaltrexone, naloxone, naltrexone, and those disclosed in: PCT Application No. WO 00/21509; (57) 11 HSD-1 (1-beta hydroxy steroid dehydrogenase type 1) inhibitor such as BVT 3498, BVT 2733, and those disclosed in WO 01/90091, WO 01/90090, WO 01/90092, and U.S. Pat. No. 6,730,690 and US Publication No. US 2004-0133011, which are incorporated by reference herein in their entirety; and (58) a minorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; (88) zonisamide, and (89) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710.

Examples of other anti-obesity agents that can be employed in combination with a compound of Formula I are disclosed in "Patent focus on new anti-obesity agents," *Exp.*

*Opin. Ther. Patents,* 10: 819-831 (2000); "Novel anti-obesity drugs," *Exp. Opin. Invest. Drugs,* 9: 1317-1326 (2000); and "Recent advances in feeding suppressing agents: potential therapeutic strategy for the treatment of obesity, *Exp. Opin. Ther. Patents,* 11: 1677-1692 (2001). The role of neuropeptide Y in obesity is discussed in *Exp. Opin. Invest. Drugs,* 9: 1327-1346 (2000). Cannabinoid receptor ligands are discussed in *Exp. Opin. Invest. Drugs,* 9: 1553-1571 (2000).

Examples of other active ingredients that may be combined with a compound of Formula I for the treatment or prevention of male or female sexual dysfunction, in particular, male erectile dysfunction, either administered separately or in the same pharmaceutical compositions, include, but are not limited to (a) type V cyclic-GMP-specific phosphodiesterase (PDE-V) inhibitors, including sildenafil and (6R, 12aR)-2,3, 6,7,12,12a-hexahydro-2-methyl-6-(3,4-methylenedioxyphenyl)-pyrazino[2',1':6,1]pyrido[3,4-b]indole-1,4-dione (IC-351); (b) alpha-adrenergic receptor antagonists, including phentolamine and yohimbine or pharmaceutically acceptable salts thereof; (c) dopamine receptor agonists, such as apomorphine or pharmaceutically acceptable salts thereof; and (d) nitric oxide (NO) donors.

The instant invention also includes administration of a single pharmaceutical dosage formulation which contains both the MC-4R agonist in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the MC-4R agonist and the second active ingredient is realized by the patient at substantially the same time. Such beneficial effect is preferably achieved when the target blood level concentrations of each active ingredient are maintained at substantially the same time. It is preferred that the combination of the MC-4R agonist and the second active ingredient be co-administered concurrently on a once-a-day dosing schedule; however, varying dosing schedules, such as the MC-4R agonist once a day and the second active ingredient once, twice or more times per day or the MC-4R agonist three times a day and the second active ingredient once, twice or more times per day, is also encompassed herein. A single oral dosage formulation comprised of both a MC-4R agonist and a second active ingredient is preferred. A single dosage formulation will provide convenience for the patient, which is an important consideration especially for patients with diabetes or obese patients who may be in need of multiple medications.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the melanocortin-4 receptor agonist, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form. In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Another aspect of the present invention provides pharmaceutical compositions which comprise a compound of Formula I, as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the typical oral dosage unit form, in which case solid pharmaceutical carriers are typically employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of structural formula I of the present invention can be prepared according to the procedures of the following Schemes and Examples, using appropriate materials and are further exemplified by the following specific examples. Moreover, by utilizing the procedures described in detail in PCT International Application Publication WO 04/089307 in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations Used in the Description of the Preparation of the Compounds of the Present Invention: BOC (Boc) is t-butyloxycarbonyl, BOP is benzotriazol-1-yloxytris(dimethylamino)-phosphonium hexafluorophosphate, Bn is benzyl, Bu is butyl, calc. or calc'd is Calculated, celite is Celite™ diatomaceous earth, CBZ (Cbz) is benzyloxycarbonyl, c-hex is cyclohexyl, c-pen is cyclopentyl, c-pro is cyclopropyl, DEAD is diethyl azodicarboxylate, DIPEA is diisopropylethylamine, DMAP is 4-dimethylaminopyridine, DMF is N,N-dimethylformamide, dppf is 1,1'-Bis(diphenylphosphino)ferrocene, EDC is 1-(3-dimethylaminopropyl)-3-ethylcarbodiimide HCl, eq is equivalent(s), ES-MS and ESI-MS are electron spray ion-mass spectroscopy, Et is ethyl, EtOAc is ethyl acetate, h or hr is hour(s), HATU is O-(7-azabenzotriazol-1-yl)-1,1,3,3-tetramethyluronium hexafluorophosphate, HMPA is hexamethyl phosphoramide, HOAt is 1-hydroxy-7-azabenzotriazole, HOBt or HOBT is 1-hydroxybenzotriazole hydrate, HPLC is high performance liquid chromatography, LC-MS or LC-MASS is liquid chromatography mass spectrum, LDA is lithium diisopropylamide, MC-xR is melanocortin receptor (x being a number), Me is methyl, MF is molecular formula, mL is milliliter, mmol is millimole(s), MPLC is medium pressure liquid chromatography, MS is mass spectrum, Ms is methane sulfonyl, MTBE is tert-butyl methyl ether, NMM is N-Methylmorpholine, NMO is N-Methylmorpholine-N-oxide, OTf is trifluoromethanesulfonyl, Ph is phenyl, Phe is phenyl alanine, Pr is propyl, iPr is isopropyl, prep. is prepared, PyBOP is benzotriazol-1-yloxytripyrrolidine-phosphonium hexafluorophosphate, PyBrop is bromo-tris-pyrrolidino-phosphonium hexafluoro-phosphate, r.t. or rt is room temperature, SCF $CO_2$ S is super critical fluid carbon dioxide, TEA is triethylamine, Tf is triflate or trifluoromethanesulfonate, TFA is trifluoroacetic acid, THF is tetrahydrofuran, and TLC is thin-layer chromatography.

Reaction Schemes A-O illustrate methods employed in the synthesis of the compounds of the present invention of structural formula I. All substituents are as defined above unless indicated otherwise.

Reaction Scheme A illustrates a key step in the synthesis of the novel compounds of structural formula I of the present invention. As shown in reaction Scheme A, the reaction of a piperidine derivative of type 1 with a carboxylic acid derivative of formula 2 affords a title compound of structural formula I. The amide bond coupling reaction illustrated in reaction Scheme A is conducted in an appropriate inert solvent such as DMF, methylene chloride or the like and may be performed with a variety of reagents suitable for amide coupling reactions such as HATU, EDC or PyBOP. Preferred conditions for the amide bond coupling reaction shown in reaction Scheme A are known to those skilled in organic synthesis. Such modifications may include, but are not limited to, the use of basic reagents such as TEA, DIPEA, or NMM, or the addition of an additive such as HOAt or HOBt. Alternatively, 4-substituted piperidines of formula 1 may be treated with an active ester or acid chloride derived from carboxylic acid 2 which also affords compounds of structural formula I. The amide bond coupling shown in reaction Scheme A is usually conducted at a temperature between 0° C. and room temperature, occasionally at elevated temperatures, and the coupling reaction is typically conducted for periods of 1 to 24 hours.

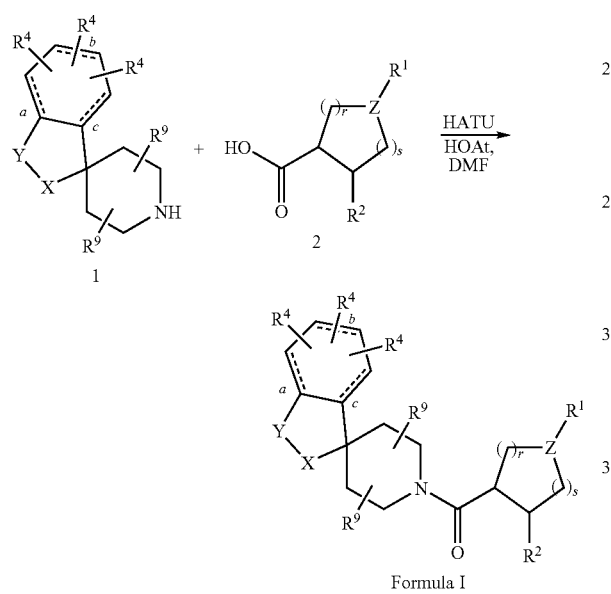

Scheme A

Formula I

If it is desired to produce a compound of structural formula I wherein Z is a nitrogen and $R^1$ is a hydrogen, the N—BOC protected analogs of structural formula I may be used in the synthesis and deprotected under acidic conditions, for instance using trifluoroacetic acid in a solvent like methylene chloride or hydrogen chloride in a solvent such as ethyl acetate at a temperature between 0° C. and room temperature.

When it is desired to prepare compounds of structural formula I wherein Z is a nitrogen and $R^1$ is not a hydrogen, the compounds of general formula I (Z=N, $R^1$=H) may be further modified using the methodology described below in reaction Scheme B. For example, the N—BOC protected compound of structural formula I can be deprotected under acidic conditions for instance by treatment with hydrogen chloride in ethyl acetate or using trifluoroacetic acid in dichloromethane as previously described. The resulting heterocyclic compound of structural formula I (Z=N, $R^1$=H) may then be subjected to one of several alkylation strategies known in organic chemistry to add another $R^1$ group. For instance, compounds (I) (Z=N, $R^1$=H) may be utilized in a reductive amination reaction with a suitable carbonyl containing reagent 3. The reductive amination is achieved by initial formation of an imine between the amine of formula I (Z=N, $R^1$=H) and either an aldehyde or ketone of formula 3. The intermediate imine is then treated with a reducing agent capable of reducing carbon-nitrogen double bonds such as sodium cyanoborohydride or sodium triacetoxyborohydride and an alkylated product of structural formula I is produced. Alternatively, a heterocyclic compound of structural formula (I) (Z=N, $R^1$=H) may be directly alkylated using an alkylating agent such as 4 in a polar aprotic solvent such as DMF. In this reaction, the substituent leaving group, LG, of compound 4 is a leaving group such as a halide, mesylate or triflate, and the product is the compound of structural formula I (Z=N) bearing the $R^1$ substituent.

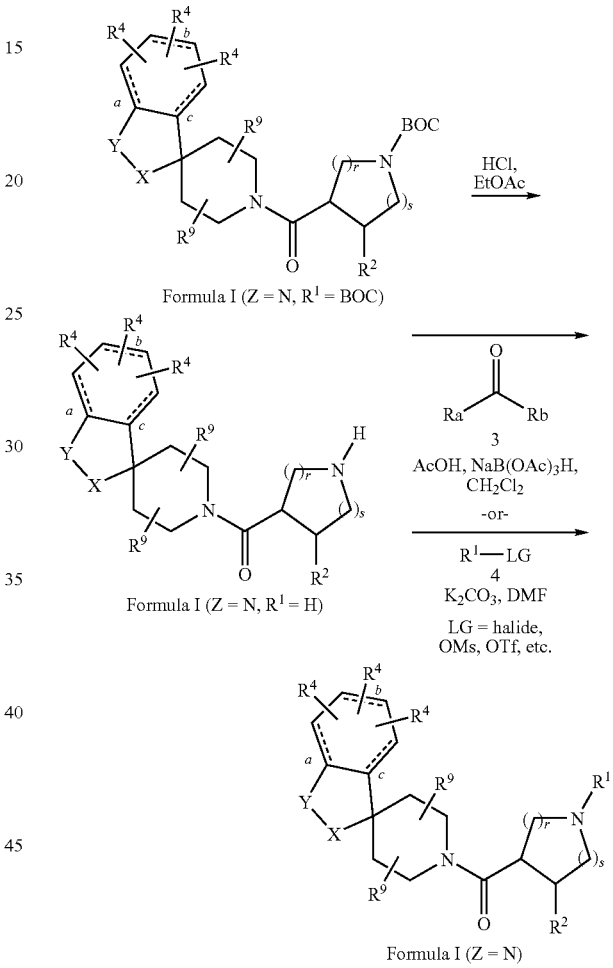

Scheme B

Reaction Schemes C-T illustrate methods for the synthesis of the carboxylic acids of general formula 2 that are utilized in the amide bond coupling reaction shown in reaction Scheme A. These schemes also feature methods for modification or elaboration of compounds of general formula I. Reaction Schemes P-U illustrate additional methods for the synthesis of 4,4-disubstituted piperidines of general formula 1 that are used in the amide bond coupling reaction, and also feature methods for elaboration of compounds of general formula I.

Reaction Scheme C illustrates a preferred method for the synthesis of compounds of general formula 2 wherein Z is a nitrogen, r is 2 and s is 1 such that the resulting heterocycle is a 3-aryl-4-piperidine carboxylic acid derivative 11 (n=1); and the synthesis of compounds of formula 2 wherein Z is a nitrogen, r is 1 and s is 1 such that the resulting heterocycle is a 3-aryl-4-piperidine carboxylic acid derivative 14 (n=2). The synthesis of 11 and 14 begins with a commercially available substituted benzene 5, such as difluorobenzene, which is derivatized to give the chloro ketone 6 via treatment with aluminum chloride and chloroacetylchloride. The ketone of 6 is reduced to the alcohol 7 using a borane N,N diethylaniline complex and a solution of (S)-2-methyl-CBS oxazaborolidine in MTBE, and the chlorine is displaced by $R^1NH_2$, for instance tert-butyl amine to give 8. The secondary amine nitrogen of 8 is alkylated with 4-bromo butyl nitrile (n=2) or 3-bromo propyl nitrile (n=1) to give nitrile compounds 9 and 12, which may be cyclized to the piperidine 13 and pyrrolidine 10 by treatment with LiHMDS and diethylphosphoryl chloride. Treatment of the nitrites 10 and 13 with sodium hydroxide provides the amides, which are subsequently converted to the corresponding methyl esters using HCl/MeOH and acetyl chloride, and to acids 11 and 14 by treatment with concentrated HCl. The resulting pyrrolidine acid 11 and piperidine acid 14 may be utilized in the coupling reaction shown in Scheme A.

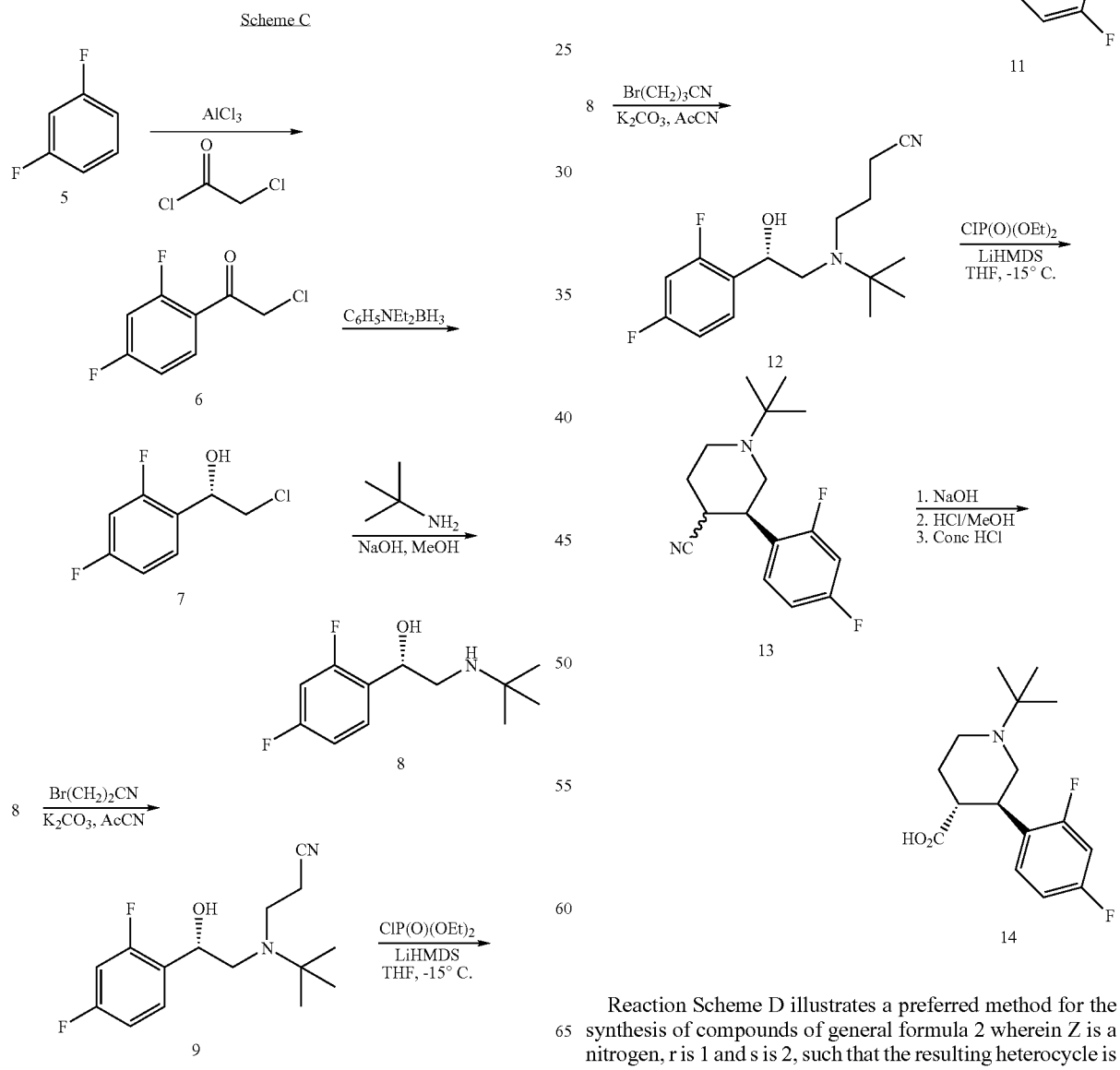

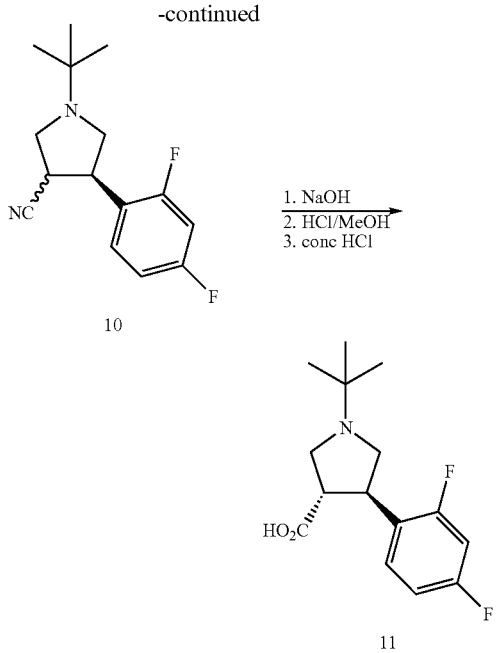

Reaction Scheme D illustrates a preferred method for the synthesis of compounds of general formula 2 wherein Z is a nitrogen, r is 1 and s is 2, such that the resulting heterocycle is a 4-aryl-3-piperidine-carboxylic acid derivative 21. The synthesis of 21 is similar to the synthesis shown in reaction Scheme C, and may begin with either of the commercially available β-keto esters 15 or 16. Conversion of 15 or 16 to the N—BOC-protected piperidine 17 is performed as shown and the resulting 0-keto ester is subjected to the two-step arylation protocol previously described in Scheme C to yield 19. Reduction of the double bond of 19 using conditions appropriate for obtaining either cis or trans 20 is followed by ester hydrolysis which affords either a cis or trans 4-aryl-3-piperidine-carboxylic acid of general formula 21 which corresponds to an acid of general formula 2 wherein Z is a nitrogen, r is 1 and s is 2. The cis or trans carboxylic acids of general formula 21 are produced as racemates and either may be resolved to afford enantiomerically pure compounds by methods known in organic synthesis. Preferred methods include resolution by crystallization of diastereoisomeric salts derived from the acids 21 and a chiral amine base or by the use of chiral stationary phase liquid chromatography columns. As before, the cis or trans carboxylic esters 20 can also be resolved by the use of chiral stationary phase liquid chromatography columns.

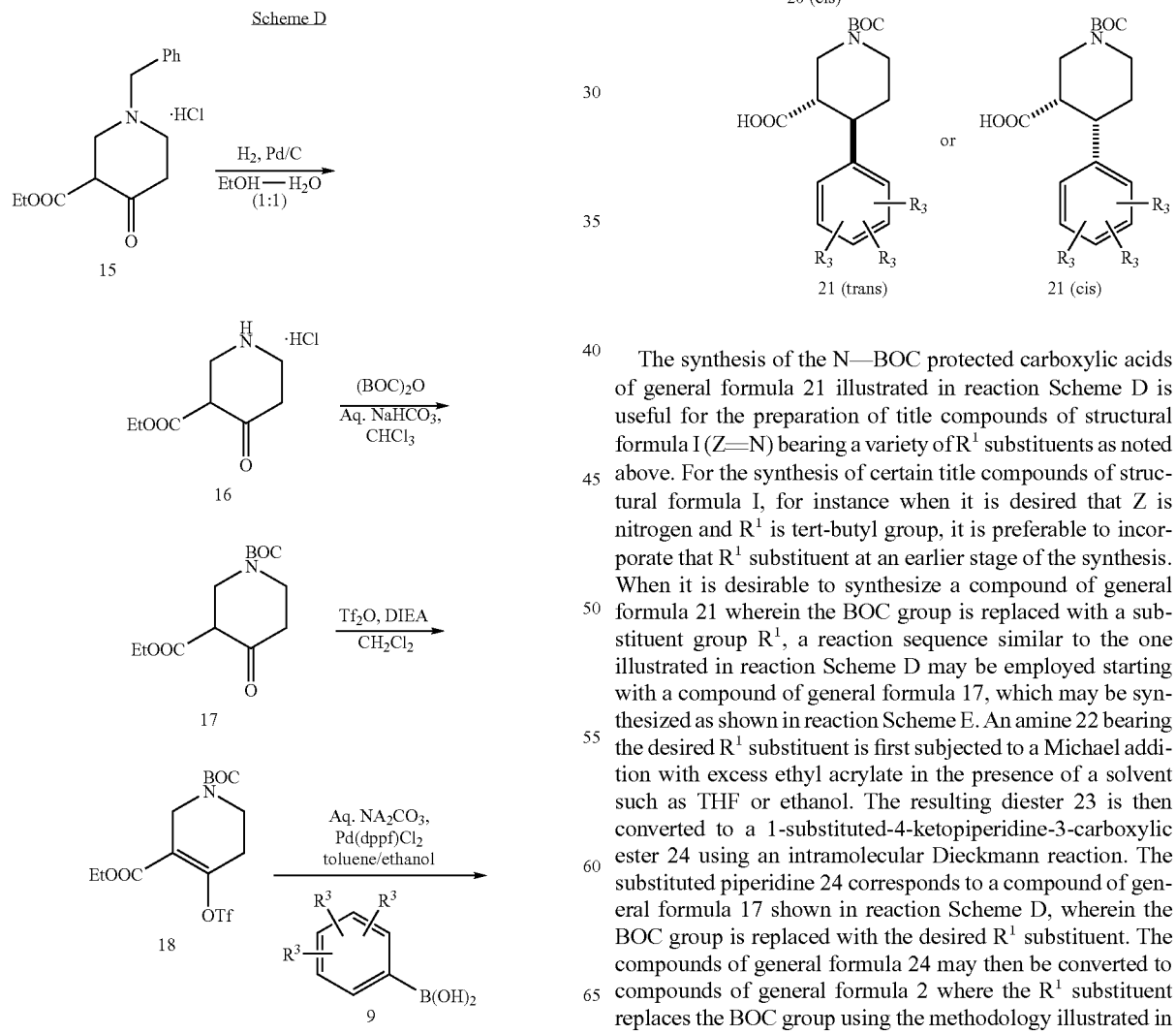

The synthesis of the N—BOC protected carboxylic acids of general formula 21 illustrated in reaction Scheme D is useful for the preparation of title compounds of structural formula I (Z=N) bearing a variety of $R^1$ substituents as noted above. For the synthesis of certain title compounds of structural formula I, for instance when it is desired that Z is nitrogen and $R^1$ is tert-butyl group, it is preferable to incorporate that $R^1$ substituent at an earlier stage of the synthesis. When it is desirable to synthesize a compound of general formula 21 wherein the BOC group is replaced with a substituent group $R^1$, a reaction sequence similar to the one illustrated in reaction Scheme D may be employed starting with a compound of general formula 17, which may be synthesized as shown in reaction Scheme E. An amine 22 bearing the desired $R^1$ substituent is first subjected to a Michael addition with excess ethyl acrylate in the presence of a solvent such as THF or ethanol. The resulting diester 23 is then converted to a 1-substituted-4-ketopiperidine-3-carboxylic ester 24 using an intramolecular Dieckmann reaction. The substituted piperidine 24 corresponds to a compound of general formula 17 shown in reaction Scheme D, wherein the BOC group is replaced with the desired $R^1$ substituent. The compounds of general formula 24 may then be converted to compounds of general formula 2 where the $R^1$ substituent replaces the BOC group using the methodology illustrated in reaction Scheme D.

Scheme E

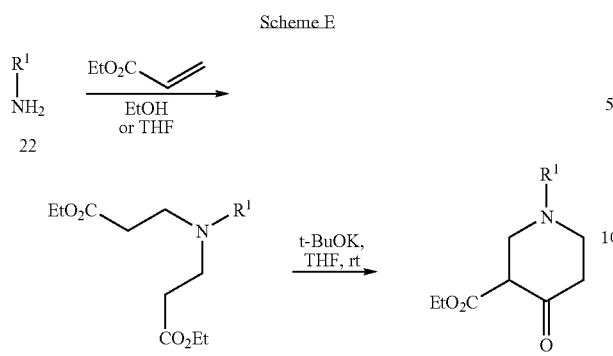

Reaction Schemes F and G illustrate the synthesis of the novel compounds of structural formula I (Z=C) when it is preferred to effect the amide bond coupling step prior to incorporation of the basic substituent $R^1$ as mentioned above. Reaction Scheme F illustrates a preferred method for the synthesis of compounds of structural formula I which employs a piperidine of general formula 1 and a cycloalkanone carboxylic acid of general formula 25 as the partners in the amide bond coupling step. The piperidine of formula 1 and the carboxylic acid of formula 25 are first coupled to afford an amide of general formula 26 using the reagents and conditions described for the generalized amide coupling shown in reaction Scheme A. The $R^1$ substituent ($R^1$=$NR^7R^8$) may then be incorporated at the position of the carbonyl group by performing a reductive amination reaction with an amine of general formula 27. Typical conditions for effecting such a reductive amination include preforming an imine 28 from ketone 26 and amine 27 followed by reduction of the intermediate imine with reducing agents such as sodium borohydride, sodium cyanoborohydride or sodium triacetoxyborohydride. Formation of the intermediate imine 28 derived from piperidine 1 and acid 25 may occur spontaneously in solution or it may be promoted with agents such as titanium (IV) isopropoxide in a solvent such as methanol or with anhydrous magnesium sulfate in chloroform. The formation of the imine 28 is generally performed at temperatures between 0° C. and the reflux temperature of the solvent, frequently at room temperature. The imine formation step is generally allowed to proceed to completion over a period of several hours to 1 day prior to the reduction step which minimizes the formation of secondary alcohols formed by simple reduction of the keto group in compounds of general formula 26. The intermediate imine 28 may in some cases be isolated and purified, however it is generally preferred to use it directly in the reduction step. The reduction of the imine 28 is typically conducted in an alcoholic solvent such as methanol or ethanol at temperatures between 0° C. and room temperature, and the reduction is generally completed in periods of several hours or less.

Scheme F

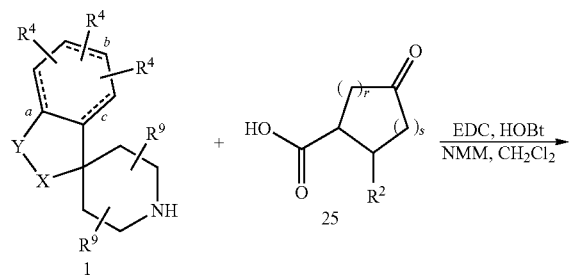

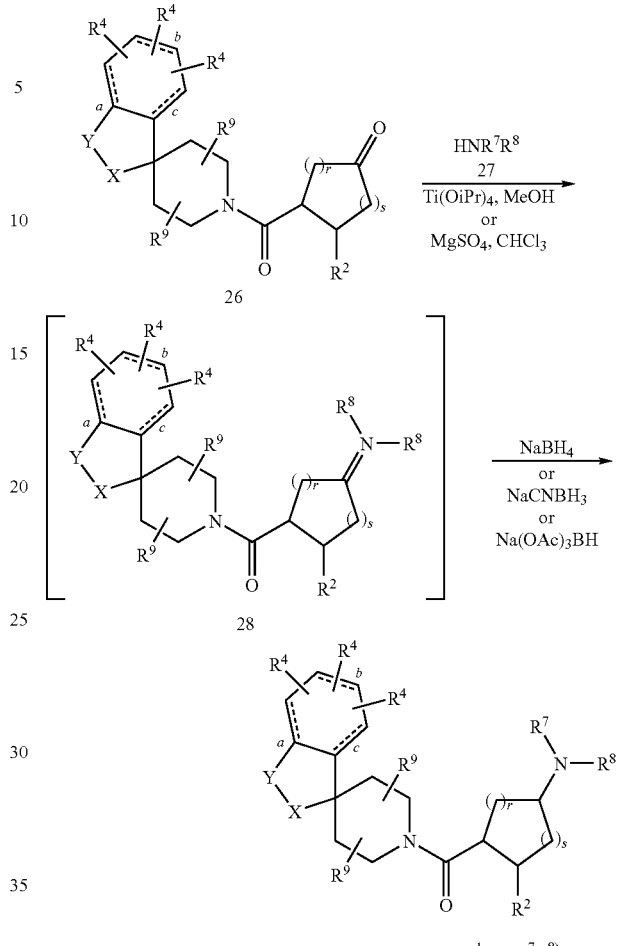

Formula I (Z = C, $R^1$ = $NR^7R^8$)

Reaction Scheme G illustrates a preferred method for the synthesis of compounds of structural formula I (Z=C) which employs a piperidine of general formula 1 and a hydroxyl-substituted cycloalkyl carboxylic acid of general formula 29 as the partners in the amide bond coupling step. The amide bond coupling step between piperidine 1 and carboxylic acid 29 is performed first, typically using a carbodimide reagent like EDC to promote the coupling as described above or by any of the other methods described in the discussion for reaction Scheme A. The hydroxyl-substituted amide 30 which is produced is then further synthetically modified to incorporate the $R^1$ substituent present in the title compounds of structural formula I (Z=C). A variety of methods known to those skilled in organic synthesis may be used to incorporate the $R^1$ substituent. For instance, the hydroxyl group of compounds of general formula 30 may be oxidized using a variety of methods to afford carbonyl compounds of general formula 26. The resulting ketoamides of general formula 26 may then be converted to the title compounds of structural formula I (Z=C) using the reductive amination method described in reaction Scheme F.

Occasionally, it may be preferable to utilize hydroxyl-substituted compounds of general formula 30 in a Fukuyama-Mitsunobu reaction (Fukuyama, T.; Cheung, M.; Jow, C.-K.; Hidai, Y.; Kan, T. *Tetrahedron Lett.* 1997, 33, 5831-4) sequence as shown in reaction Scheme H. In this method for the synthesis of the novel title compounds of structural formula I (Z=C), the intermediate hydroxyl-substituted cycloalkylamide 30 is reacted with a 2,4-dinitrobenzenesulfonamide of general formula 31 in the presence of triphenylphosphine and an azodicarboxylate reagent such as DEAD. The reaction is performed in a suitable aprotic solvent such as benzene, toluene or THF, typically at room temperature, and the reaction is generally complete in 0.5-3 hours. The product of this reaction is the secondary 2,4-dinitrobenzenesulfonamide of general formula 32, which may then be readily converted to a title compound of structural formula I (Z=C) wherein $R^8$=H. The deprotection of the sulfonamide group is accomplished by reaction of 32 with either a base like n-propylamine in a solvent like methylene chloride or by reaction of 32 with a nucleophilic reagent such as mercaptoacetic acid with TEA in methylene chloride. In either case the reaction is typically conducted at room temperature, for periods of 5 minutes to one hour. An advantage of the Fukuyama-Mitsunobu reaction sequence is that the stereochemistry of the carbon atom undergoing substitution is cleanly inverted. Thus if the hydroxyl-substituted cycloalkylamide 30 is a single diastereoisomer, then the product 32 will be a single diastereoisomer also. This is in contrast to the reductive amination strategy discussed in reaction Scheme F which generally affords a mixture of epimeric products.

The secondary amine of formula I (Z=C, $R^1$=N(H)$R^7$) shown in reaction Scheme G may then be further synthetically modified using a variety of methods known in organic synthesis to incorporate other embodiments of the $R^8$ substituent. For instance, a compound of structural formula I (Z=C) where $R^8$=H may be subjected to a reductive amination reaction with an appropriate aldehyde or ketone using the conditions described in reaction Scheme F. Alternatively, a compound of structural formula I (Z=C) where $R^8$=H may be directly alkylated with an appropriate alkylating agent using the conditions described in reaction Scheme B.

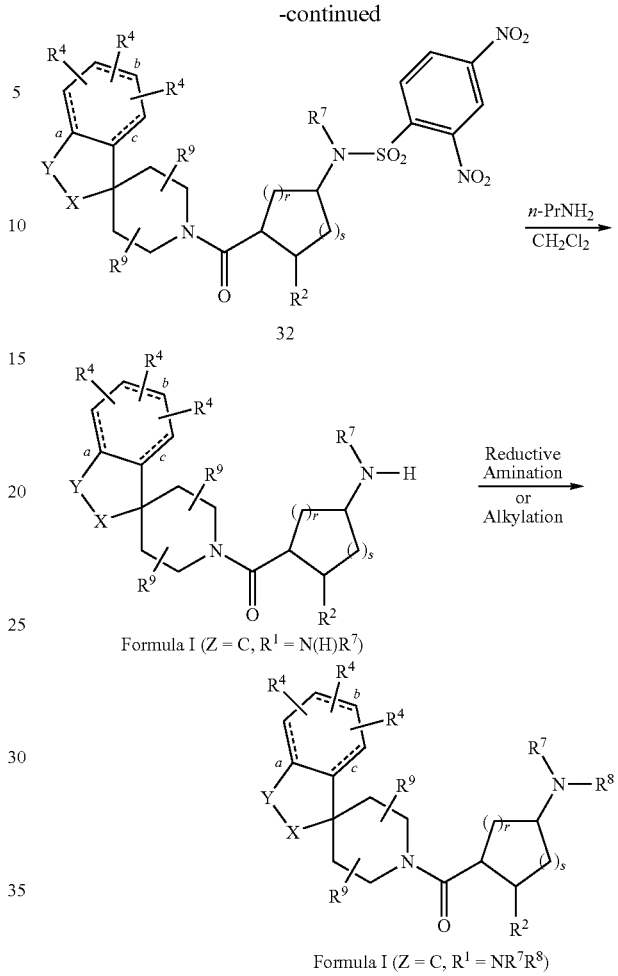

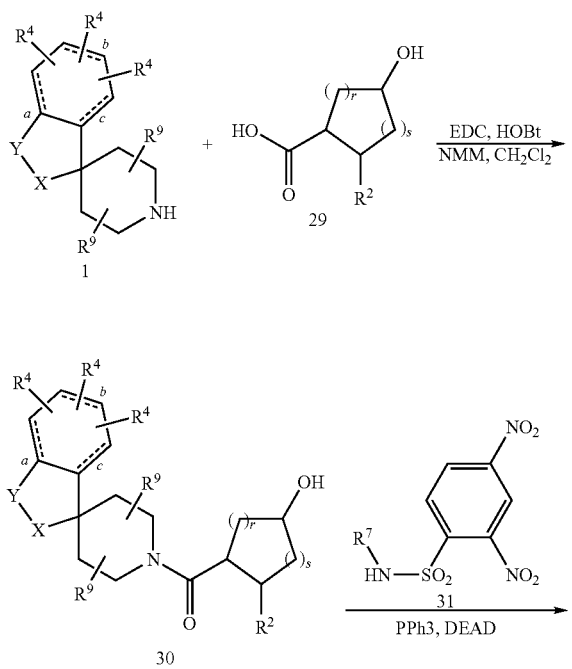

Enantiomerically pure compounds may be prepared from starting materials bearing a suitable covalently attached chiral auxiliary group using synthetic transformations similar to those outlined above. Reaction Scheme H illustrates the use of a covalently attached chiral oxazolidinone auxiliary for the preparation of enantiomerically pure cyclopentanones of general formula 41. In this synthetic method, cinnamyl oxazolidinones of general formula 35 are readily prepared from cinnamic acids and (S)-(−)-4-benzyl-2-oxazolidinone using published methodology (Ho, G.-J.; Mathre, D. J. *J. Org. Chem.* 1995, 60, 2271 and references cited therein). The acylation of chiral auxiliary 34 with cinnamic acids of formula 33 is performed by initial activation of the acid to afford a mixed anhydride. Typically acids of general formula 33 are reacted with an acid chloride such as pivaloyl chloride in the presence of a base such as TEA and in a suitable aprotic solvent such as THF. The intermediate cinnamyl-pivaloyl anhydride is converted to the product 35 by reaction with the oxazolidinone 34 in the presence of lithium chloride, an amine base such as TEA and in a solvent such as THF, and the reaction is conducted at temperatures between −20° C. and room temperature for periods of 1-24 hours. Alternatively, the oxazolidinone 34 may be deprotonated with a strong base such as n-butyllithium in THF at low temperatures such as −78° C. and then reacted with a mixed anhydride obtained from acid 33 and an acid chloride like pivaloyl chloride as noted above. The α,β-unsaturated acyloxazolidone of general formula 35 is subjected to the trimethylenemethane cycloaddition reaction (Trost, B. M.; Chan, D. M. T. *J. Am. Chem. Soc.* 1979, 101, 6429) with compound 36 to afford a cyclopentane derivatives of general formula 37 and 38. The cycloaddition is performed by reacting the α,β-unsaturated ester of general formula 35 with 2-[(trimethylsilyl)methyl]-2-propen-1-yl acetate 36 in the presence of a palladium(0) catalyst in a solvent such as THF. A preferred palladium (0) catalyst for the cycloaddition may be generated by mixing palladium acetate and triisopropyl phosphite in the reaction mixture. The cycloaddition reaction is typically conducted at the reflux temperature of the solvent, for instance 65° C., and the reaction is usually completed in periods of 2-8 hours. The olefin geometry of the starting α,β-unsaturated ester of general formula 35 determines the relative stereochemistry of the two substituents on the five-membered ring. Thus a trans α,β-unsaturated ester 35 affords the trans-disubstituted products 37 and 38 as shown, whereas the corresponding cis isomer of compounds of general formula 35 affords the corresponding cis-disubstituted isomer of 37 and 38. The exocyclic olefin present in compounds of general formula 40 is oxidatively removed to afford a cyclopentanone derivative of general formula 41.

Compounds of general formulae 37 and 38 are readily separated from each other by conventional chromatographic methods or by recrystallization, and may then be converted to the compounds of general formula 41 individually. This process is illustrated at the bottom of reaction Scheme H for the case of the cyclopentane with the absolute stereochemistry shown in formula 39. The enantiomerically pure compounds of general formula 39 are first hydrolyzed to afford intermediate carboxylic acids and (S)-(−)-4-benzyl-2-oxazolidinone using a reagent such as lithium hydroperoxide, typically generated in situ, in a suitable solvent system such as aqueous THF. The carboxylic acid formed is generally then converted to a methyl ester 40 using diazomethane, trimethylsilyldiazomethane or any of the esterification methods commonly employed in organic synthesis. The olefin present in the esters of general formula 40 is then subjected to oxidative cleavage to afford enantiomerically pure compounds of general formula 41. The methylene cyclopentane derivative of formula 40 is first oxidized to a 1,2-diol derivative using catalytic osmium tetraoxide in the presence of a stoichiometric reoxidant such as N-methylmorpholine-N-oxide and a solvent system such as acetone-water. The intermediate 1,2-diol which forms is generally not isolated, but is in turn subjected to cleavage with sodium periodate in a solvent system like methanol-water to afford ketones of general formula 41. Both steps in the oxidative cleavage sequence are generally completed during periods of several minutes to a few hours and the reaction steps are typically conducted at low temperatures, for instance between 0° C. and room temperature. Alternatively, the oxidative cleavage of olefins of general formula 40 may be accomplished using ozone, or by other methods known in organic synthesis. The cyclopentanones of general formula 41 may then be hydrolyzed, for instance using sodium hydroxide in methanol, to afford the carboxylic acids of general formula 42 (r=1, s=1). The acids of general formula 42 are finally converted to the novel title compounds of structural formula I (Z=C) using the methodology described above in reaction Schemes F and G.

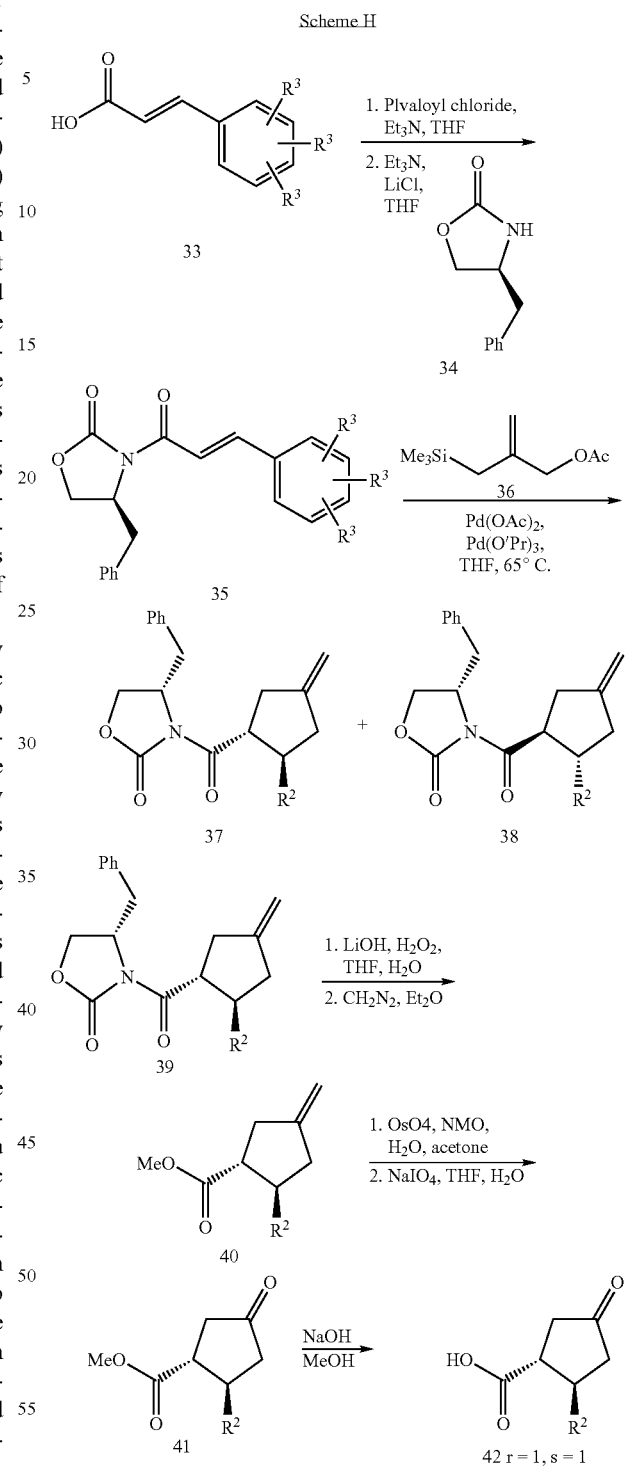

When it is desired to prepare individual enantiomers of the novel title compounds of structural formula I, it is possible to perform a resolution of the compounds of structural formula I using one of the methods known in the art of organic synthesis. For instance, enantiomerically pure compounds (I) may be prepared by crystallization of diastereoisomeric salts formed from the racemic compounds of structural formula I and an optically active carboxylic acid. The two diastereoisomberic salts are separated from each other by fractional crystallization, then the enantiomerically pure compounds of structural formula I are regenerated by treatment of the purified salts with a base. Alternatively, racemic compounds of structural formula I may be resolved by preparative HPLC using commercially available chiral stationary phase columns. Another strategy for the preparation of enantiomerically pure compounds of structural formula I involves preparing enantiomerically pure compounds of general formula 2 prior to their use in the amide bond forming reaction outlined in reaction Scheme A. Racemic compounds of general formula 2, or intermediates used to prepare compounds of formula 2 as described in the previous reaction Schemes (i.e. acids 11, 14, 21, and 42, or esters 20 and 41) may also be resolved using the classical methods previously discussed.

Scheme I discloses examples of 4,4-disubstituted piperidine intermediates of general formula 1 used as indicated in the examples of the present invention. The 4,4-disubstituted piperidine intermediates of general formula I-1, I-2 and I-3 in Scheme I, which may be employed to synthesize the compounds of this invention, may be prepared according to the methods disclosed in U.S. Pat. No. 5,804,578 (Sep. 8, 1998), U.S. Pat. No. 5,578,593 (Nov. 26, 1996), U.S. Pat. No. 6,472,398 (Oct. 29, 2002), U.S. Pat. No. 6,294,534 (Sep. 25, 2001), WO 01/70337, WO 99/64002, and WO 04/089307.

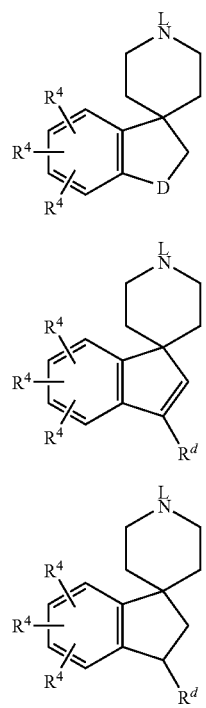

L is H or a protecting group
D is O, S, NR, NH, NS(O)$_2$R, S(O), or S (O)$_2$ or CH(R$^7$)
R$^7$ is (CH$_2$)$_n$ aryl, -C(O)R$^2$, -SO$_2$R$^2$, -C(O)NR$^2$)$_2$, -CO$_2$R$^2$, -SO$_2$NR$^2$, or as defined in 5,804,578

R$^2$ is as defined in 5,804,578
R$^d$ is (CH$_2$)$_n$CO$_2$H, (CH$_2$)$_n$CO$_2$Me, -CON(R$^2$)$_2$, -OTs, -OTf, CN, -SMe, tetrazole, pyridine, -Sn(Me)$_3$ or as defined in 5,804,578

Reaction Scheme J illustrates a preferred method for the synthesis of a compound of general formula 1 X=C, Y=CHN(H)CBZ, R$^9$ is H). In this method, a carboxylic acid such as 43 is subjected to the Curtius reaction to afford a product of general formula 44. The reaction is performed by reacting acid 43 with diphenylphosphoryl azide in the presence of a tertiary amine such as TEA or diisopropylamine in a solvent such as toluene. The rearrangment is typically conducted at the reflux temperature of the solvent, for instance 110° C., and the rearrangement is usually completed in periods of 1-5 hours. The intermediate isocyanate which forms is generally not isolated, but is in turn subjected to in-situ reaction with a suitable alcohol such as benzyl alcohol to afford a product of general formula 44. The N—BOC group can be removed by any of the known methods such as treatment with a protic acid such as hydrogen chloride in an inert organic solvent such as ethyl acetate or trifluoroacetic acid in methylene chloride. The product amine 45 can be used as a coupling partner in reaction Scheme A.

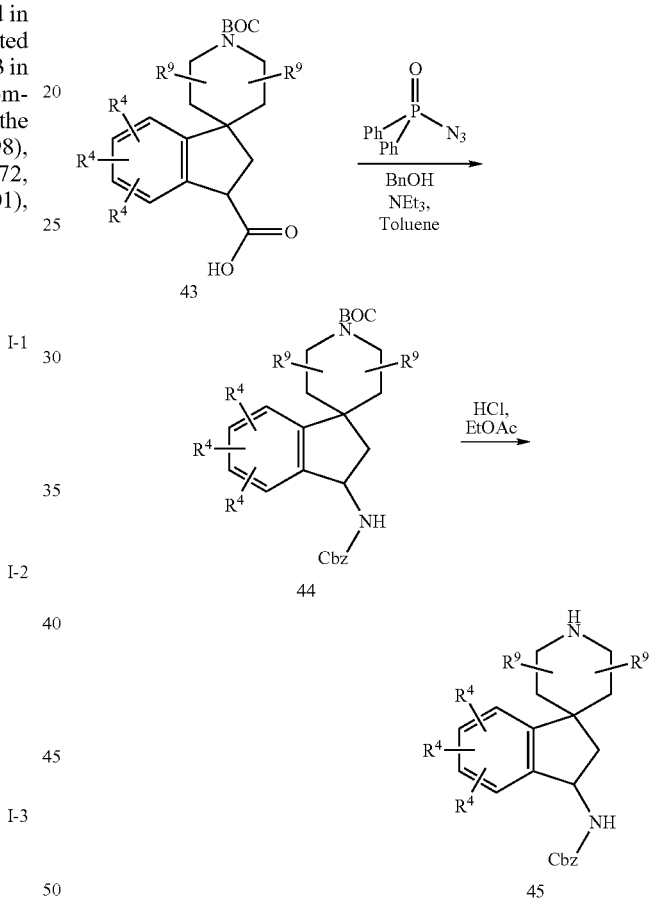

Reaction Scheme K illustrates general methods for the elaboration of the Y substituent following assembly of compounds of structural formula I (X=C, Y=CHCO$_2$Me) as described in reaction Scheme A. For example, conversion of the methyl ester to the carboxylic acid of structural formula I (X=C, Y=CHCO$_2$H) can be affected by dealkylation using potassium trimethylsilanolate at room temperature in an inert organic solvent such as THF for a period of about one to about 24 hours to provide, after acidification, the corresponding carboxylic acid. In certain cases, a base-catalyzed hydrolysis known to those skilled in the art may be used to effect this same transformation. The acid may be reacted further to form an amide by treatment with a primary or secondary amine under a variety of amide coupling protocols such as those described in Scheme A to provide a compound of structural formula I (X=C, Y=CHCONR$^7$R$^8$).

Scheme K

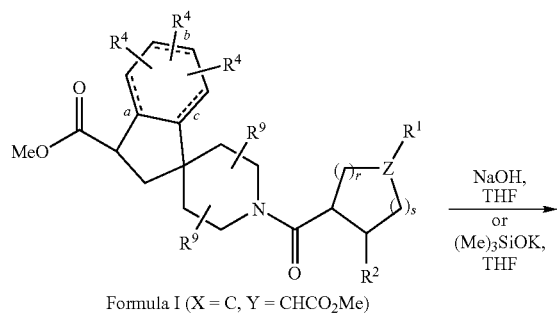

Formula I (X = C, Y = CHCO$_2$Me)

NaOH, THF
or
(Me)$_3$SiOK, THF

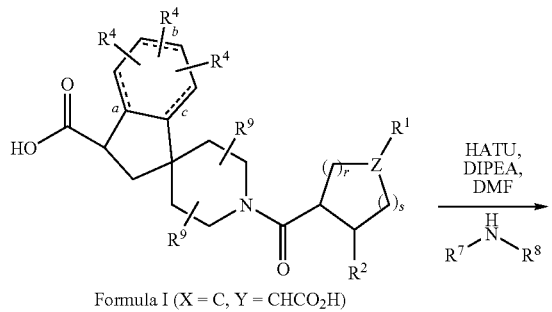

Formula I (X = C, Y = CHCO$_2$H)

HATU, DIPEA, DMF

R$^7$—N(H)—R$^8$

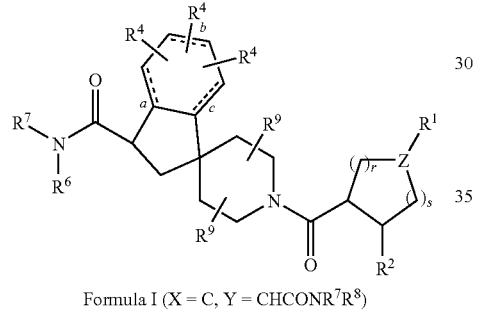

Formula I (X = C, Y = CHCONR$^7$R$^8$)

Scheme L

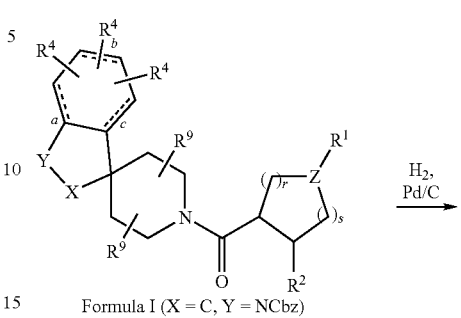

Formula I (X = C, Y = NCbz)
Formula I (X = C, Y = CHN(H)Cbz)

H$_2$, Pd/C

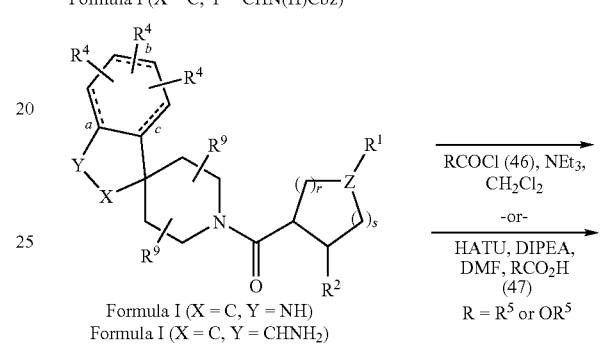

Formula I (X = C, Y = NH)
Formula I (X = C, Y = CHNH$_2$)

RCOCl (46), NEt$_3$, CH$_2$Cl$_2$
-or-
HATU, DIPEA, DMF, RCO$_2$H (47)

R = R$^5$ or OR$^5$

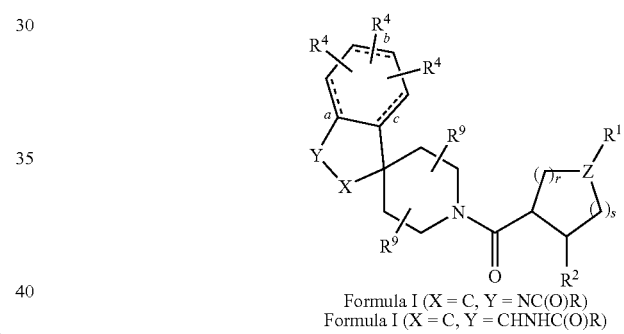

Formula I (X = C, Y = NC(O)R)
Formula I (X = C, Y = CHNHC(O)R)

Reaction Scheme L illustrates general methods for the elaboration of the Y substituent following assembly of compounds of structural formula I (X═C, Y═N(H)CBZ or CHN (H)CBZ) as described in reaction Scheme A. The N—CBZ protected compound of structural formula I (X═C, Y═N(H) CBZ or CHN(H)CBZ) is first deprotected by hydrogenolysis using a palladium-on-carbon catalyst in a solvent system such as methanol, ethanol, acetic acid or mixtures thereof under a hydrogen atmosphere. The resulting compound of structural formula I (X═C, Y═NH or CHNH$_2$) may then be subject to one of several acylation methods known in organic chemistry. For instance, a compound of structural formula I (X═C, Y═NH or CHNH$_2$) can be reacted with a carboxylic acid 47 under a variety of amide coupling protocols such as those described in the discussion for Scheme A to provide a product of structural formula I (X═C, Y═NC(O)R or CHNHC(O) R). Alternatively, a compound of structural formula I (X═C, Y═NH or CHNH$_2$) may be acylated using an acid chloride derivative 46. The acylation reaction is typically conducted in the presence of a tertiary amine such as triethylamine, N,N-diisopropylethylamine or N-methylmorpholine in an aprotic solvent such as methylene chloride or DMF to afford a product of structural formula I (X═C, Y═NC(O)R or CHNHC (O)R) as shown in Scheme L.

Reaction Scheme M illustrates general methods for the elaboration of the Y substituent following assembly of compounds of structural formula I (X═C, Y═NH) as described in the preceeding reaction Scheme L. For example, a compound of structural formula I (X═C, Y═NH) may be subjected to one of several alkylation strategies known in organic chemistry. For instance, compound (1) (X═C, Y═NH) may be utilized in a reductive amination reaction with a suitable carbonyl containing partner (67). The reductive amination is achieved by initial formation of an imine between the amine of formula I (X═C, Y═NH) and either an aldehyde or ketone of formula 48. The intermediate imine is then treated with a reducing agent capable of reducing carbon-nitrogen double bonds such as sodium cyanoborohydride or sodium triacetoxyborohydride and an alkylated product of structural formula I (X═C, Y═NR) is produced. Alternatively, a compound of structural formula (I) (X═C, Y═NH) may be directly alkylated using an alkylating agent such as 49 in a polar aprotic solvent such as DMF. In this reaction, the substituent leaving group, LG, of compound 49 is a leaving group such as a halide, mesylate or triflate and the product is the compound of structural formula I (X═C, Y═NR$^6$).

Scheme M

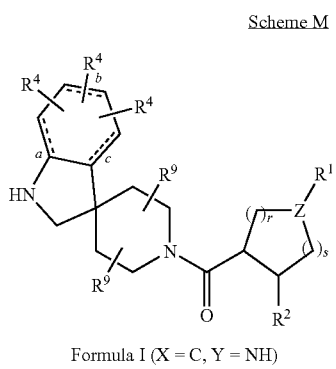

Formula I (X = C, Y = NH)

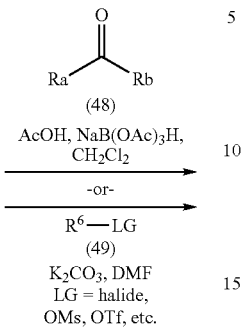

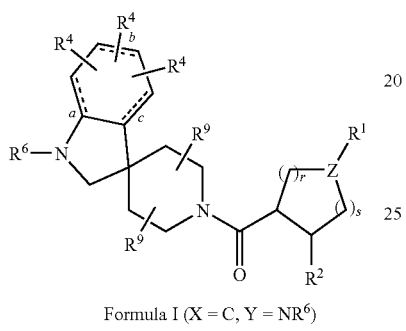

Formula I (X = C, Y = NR$^6$)

In a similar manner to the conditions described in reaction Scheme M, compounds of structural formula I (X=C, Y=CHNH$_2$) can be elaborated to products of structural formula I (X=C, Y=CHN(H)R), and can be further elaborated to products of structural formula I (X=C, Y=CN(R)$_2$), as shown in Scheme N.

Scheme N

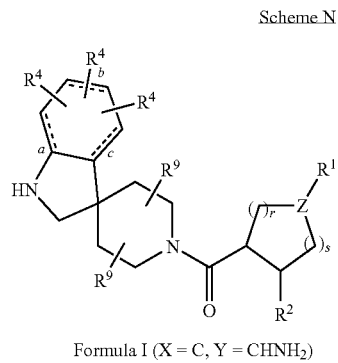

Formula I (X = C, Y = CHNH$_2$)

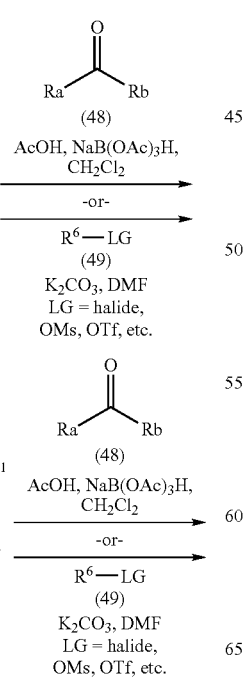

Formula I (X = C; and Y = CHN(H)R - wherein N(H)R = R$^6$)

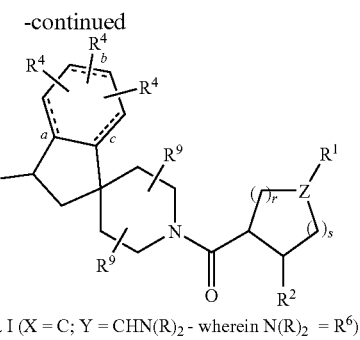

Formula I (X = C; Y = CHN(R)$_2$ - wherein N(R)$_2$ = R$^6$)

Reaction Scheme O illustrates a general method for reducing the aryl ring of compounds of general formula O-1 to provide the cyclohexyl compounds of general formula O-2. The aryl ring of a compound of formula O-1 may be reduced by hydrogenation in the presence of a platinum (IV) oxide catalyst in a solvent such as glacial acetic acid at an elevated pressure, such as 45 psi of hydrogen gas.

Scheme O

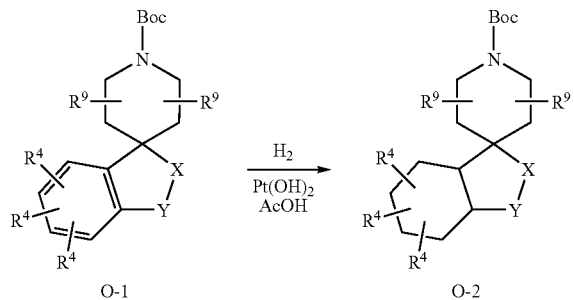

The following examples are provided to illustrate the invention and are not to be construed as limiting the scope of the invention in any manner.

Scheme P

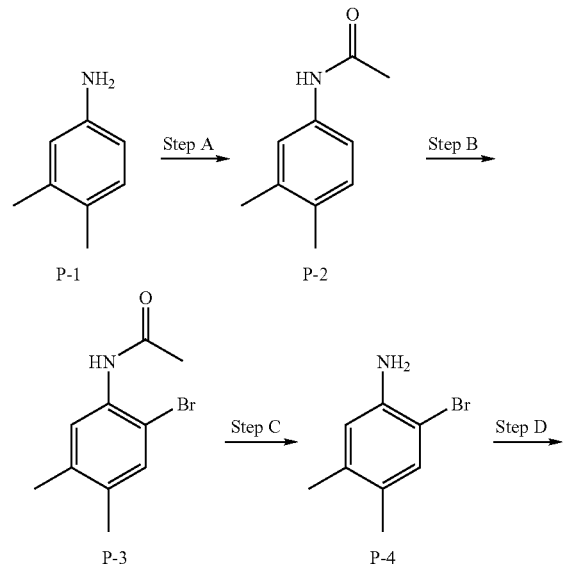

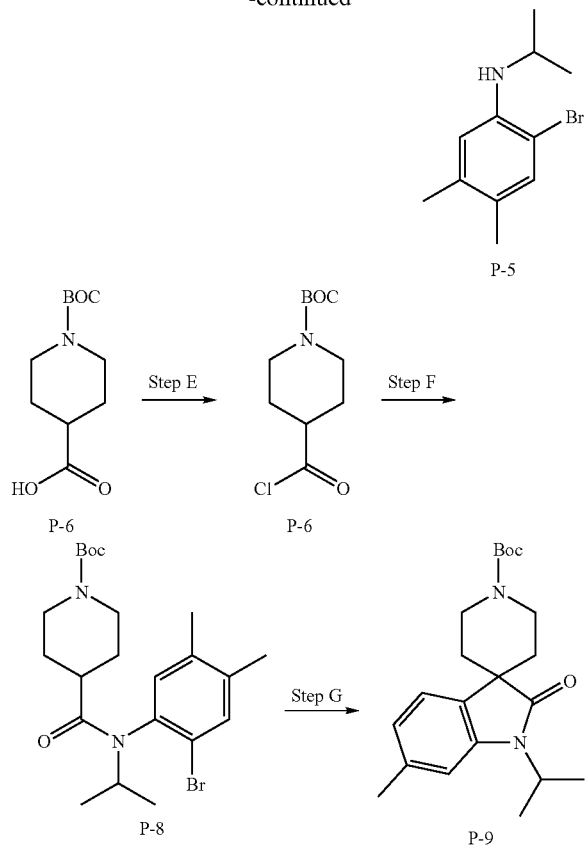

Step A: Acetic anhydride (38.9 mL) was added to a stirred solution of 3,4-dimethylaniline P-1 (10.0 g, as prepared in WO 2004/089307) in pyridine (150 mL) at ambient temperature. After stirring at approximately 60° C. for 2 h, the volatiles were removed in vacuo, and the residue was partitioned between diethyl ether and aqueous 1 N hydrochloric acid. The organic phase was separated and washed with saturated aqueous sodium bicarbonate, brine, dried (sodium sulfate) and concentrated in vacuo to afford P-2 as a white crystalline solid.

Step B: Bromine (5.08 mL) was added over 1 h to a stirred solution of N-(3,4-dimethylphenyl)acetamide P-2 (13.5 g) in acetic acid (200 mL) at approximately 15° C. After 15 minutes, water (400 mL) was added until no further precipitation was observed. The resultant solid was filtered, washed with water (until white) and dried in vacuo to afford P-3 as a white crystalline solid.

Step C: Potassium hydroxide (15.9 g) was added to a stirred solution of N-(2-bromo-4,5-dimethylphenyl)acetamide P-3 (17.2 g) in methanol (350 mL) at ambient temperature. After stirring at approximately 80° C. for 118 h, the reaction mixture was cooled and the organic volatiles removed in vacuo. The remaining aqueous phase was diluted with additional water (65 mL) and the resultant solid product was filtered, washed with water and dried in vacuo to afford P-4 as a white solid.

Step D: A solution of acetone (5.60 mL) and aqueous 4 M sulfuric acid (5.20 mL) in THF (15 mL) was added dropwise to a stirred solution of 2-bromo-4,5-dimethylaniline P-4 (13.9 g) in THF (40 mL) at approximately 0° C. Sodium borohydride (2.62 g) was added cautiously and the resulting mixture allowed to warm to ambient temperature. After 30 min, the reaction was quenched by the careful sequential addition of water (25 mL) and sodium hydroxide pellets (until strongly alkaline). The reaction mixture was extracted with tert-butyl methyl ether (150 mL) and the organic phase was washed with brine, dried (sodium sulfate) and concentrated in vacuo to give a crude residue. Purification of the crude residue by flash chromatography over silica gel (gradient elution; 0%-20% ethyl acetate/hexanes as eluent) afforded P-5 as a clear, pale orange oil.

Step E: Oxalyl chloride (32.7 mL of a 2 M solution in methylene chloride) followed by N,N-DMF (0.5 mL) were added to a stirred solution of 1-(tert-butoxycarbonyl)piperidine-4-carboxylic acid P-6 (10.0 g) in methylene chloride (150 mL) at approximately 0° C. After 1 h, the volatiles were removed in vacuo, azeotroping twice with toluene to afford P-7 as an orange oil. Compound P-7 was dissolved in methylene chloride to generate 43.6 mL of a 1M solution and used as such in the subsequent reaction.

Step F: N,N-dimethylaniline (7.12 mL) followed by tert-butyl 4-(chlorocarbonyl)-piperidine-1-carboxylate P-7 (42.1 mL of a 1 M solution in methylene chloride) were added to a neat stirred mixture of 2-bromo-N-isopropyl-4,5-dimethylaniline P-5 (6.80 g) and N,N-dimethylamino-pyridine (172 mg) at approximately 0° C. The resulting mixture was heated to reflux for 30 min, cooled to ambient temperature and partitioned between diethyl ether and aqueous 1 N hydrochloric acid. The organic phase was separated and washed successively with aqueous 1 N hydrochloric acid, saturated aqueous sodium bicarbonate, brine, dried (sodium sulfate) and concentrated in vacuo to give a crude residue. Purification of the crude residue by flash chromatography over silica gel (gradient elution; 0%-40% ethyl acetate/hexanes as eluent) afforded P-8 as a white solid.

Step G: A stirred mixture of tert-butyl 4-{[(2-bromo-4,5-dimethylphenyl)-(isopropyl)amino]-carbonyl}piperidine-1-carboxylate P-8 (3 g), bis(dibenzylideneacetone)-palladium (187 mg), racemic 2,2'-bis(diphenylphosphino)-1,1'-binaphthyl (309 mg) and sodium tert-butoxide (954 mg) in dioxane (100 mL) was heated at approximately 100° C. for 18 h. The reaction mixture was poured into aqueous 2 N hydrochloric acid and extracted three times with diethyl ether. The combined ethereal extracts were washed with brine, dried (sodium sulfate) and concentrated in vacuo to give a crude residue. Purification of the crude residue by flash chromatography over silica gel (gradient elution; 0%-40% ethyl acetate/hexanes as eluent) afforded P-9 as an off-white solid.

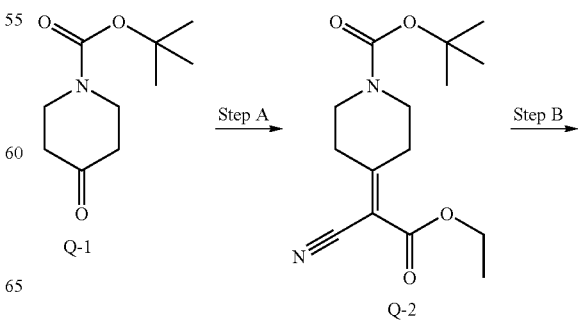

-continued
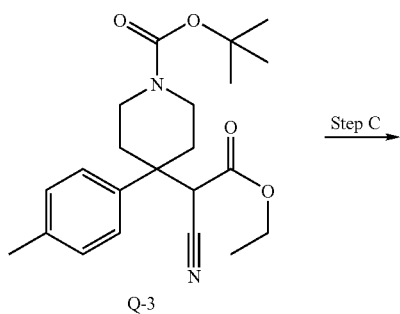
Q-3
→ Step C
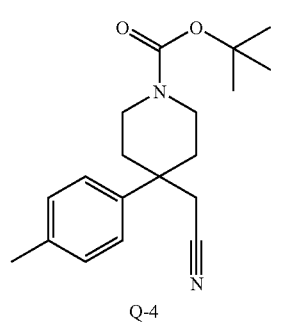
Q-4
→ Step D
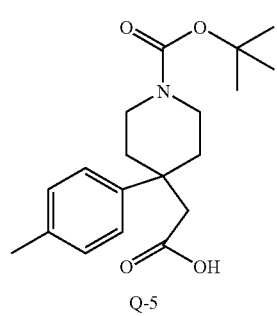
Q-5
→ Step E
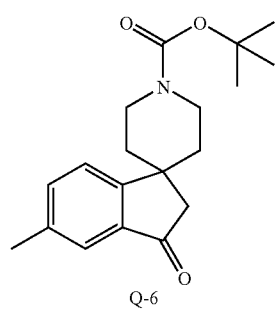
Q-6
→ Step F
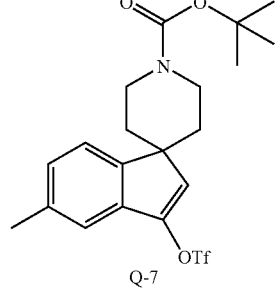
Q-7
→ Step G
-continued
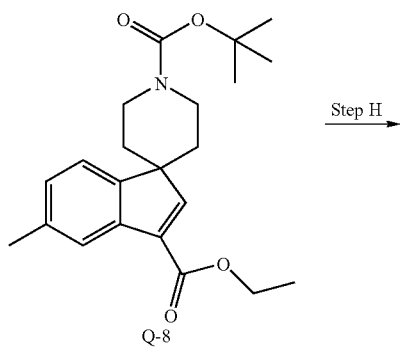
Q-8
→ Step H
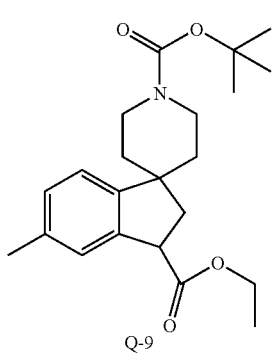
Q-9
→ Step I
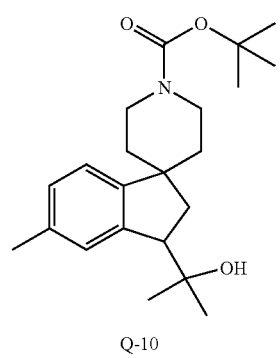
Q-10
→ Step J
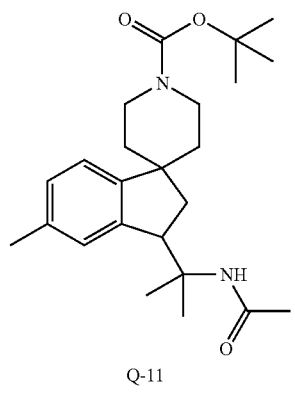
Q-11
→ Step K

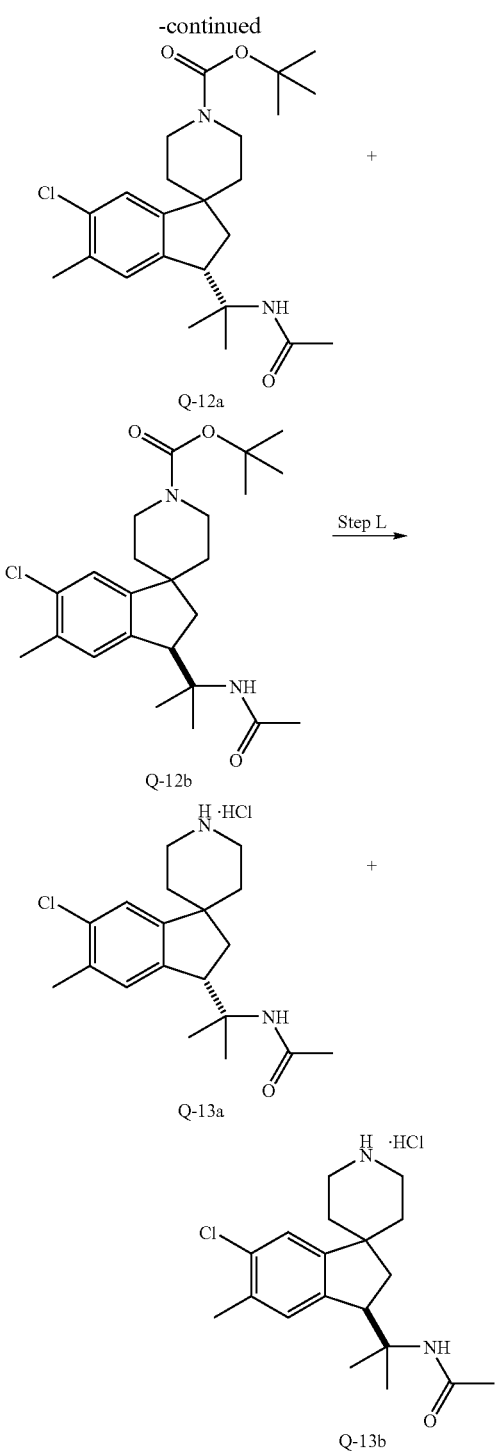

Step A: Ethyl cyanoacetate (11.0 mL), ammonium acetate (0.976 g) and acetic acid (0.715 mL) were added to a solution of tert-butyl 4-oxopiperidine-1-carboxylate Q-1 (25.0 g) in 200 mL of benzene at ambient temperature. After stirring at reflux with azeotropic removal of water (Dean-Stark apparatus), the reaction mixture was cooled to ambient temperature and diluted with ethyl acetate (500 mL). The organics were washed with saturated aqueous sodium bicarbonate, brine, dried (magnesium sulfate), and concentrated in vacuo to give a crude residue. Purification of the crude residue by recrystallization from 10% ethyl acetate/hexanes afforded Q-2 as a white crystalline solid.

Step B: p-Tolylmagnesium bromide (250 mL of a 1.0 M solution in diethyl ether) was added to a suspension of copper (1) cyanide (11.0 g) in anhydrous THF (150 mL) under nitrogen at approximately −50° C. After stirring at approximately −50° C. for 10 min, the reaction mixture was allowed to warm to ambient temperature over 1 h then recooled to approximately −50° C. A solution of tert-butyl 4-(1-cyano-2-ethoxy-2-oxoethylidene) piperidine-1-carboxylate Q-2 (30.0 g) in THF (50 mL) was added. The reaction mixture was allowed to warm to ambient temperature over 4 h. The reaction mixture was cooled to 0° C. and quenched with saturated aqueous ammonium chloride. The reaction mixture was extracted with ethyl acetate and hexanes. The organic layers were washed with brine, dried (sodium sulfate) and concentrated in vacuo to give compound Q-3 as an oil.

Step C: Lithium chloride (8.65 g) and water (14.7 mL) were added to a solution of Q-3 (102 mmol, crude from Step B) in dimethyl sulfoxide (200 mL). After stirring at approximately 160° C. for 4 h the reaction mixture was cooled to ambient temperature, poured into ice and extracted with ethyl acetate and hexanes (4×400 mL). The organic phase were washed with water, brine, dried (sodium sulfate) and concentrated in vacuo to give a crude residue. Purification of the crude residue by flash chromatography over silica gel with 25% ethyl acetate/hexanes as eluent afforded compound Q-4 as a white solid.

Step D: A mixture of concentrated hydrochloric acid (200 mL) and Q-4 (28.0 g) was heated to reflux overnight. The reaction mixture was concentrated in vacuo to give a crude residue. The residue was treated with aqueous sodium hydroxide (5 M, 45 mL) and the mixture was concentrated in vacuo. The residue was again treated with aqueous sodium hydroxide (5 M, 45 mL) and the mixture was concentrated in vacuo. The residue was treated with water (100 mL), 1,4-dioxane (100 mL) followed by di-tert-butyl dicarbonate (26.7 g). The mixture was stirred at ambient temperature overnight. The volatiles were removed in vacuo and the residue was extracted with ethyl acetate and hexanes. The organic layers were washed with brine and dried (sodium sulfate) and concentrated in vacuo to give a residue. Purification of the residue by flash chromatography over silica gel with 25% ethyl acetate/hexanes as eluent) afforded compound Q-5 as a white solid.

Step E: Oxalyl chloride (4.0 mL) was added to a solution of Q-5 (12.78 g) and N,N-dimethylamide (20 mg) at 0° C. The mixture was warmed to ambient temperature and stirred for 2.5 h. Hydrogen chloride (4.0 M in 1,4-dioxane) was added and the mixture was concentrated in vacuo. The residue was left under high vacuum pump for 0.5 h. The residue was treated with dichloromethane (100 mL) and cooled to 0° C. To this suspension was added anhydrous aluminum chloride (12.8 g). After 30 min at 0° C., the mixture was warm to ambient temperature and stirred for 1 h. The reaction mixture was poured into ice and aqueous sodium hydroxide (5 M, 50 mL). The pH of the mixture was adjusted to 9-10. The mixture was treated with 1,4-dioxane (200 mL) followed by di-tert-butyl dicarbonate (12.6 g). The mixture was stirred at ambient temperature overnight. Volatiles were removed in vacuo and the residue was extracted with ethyl acetate and dichloromethane. The organic layers were washed with brine and dried (sodium sulfate) to afford a residue. Purification of the crude residue by flash chromatography over silica gel (gradient elution; 5%-25% ethyl acetate/hexanes as eluent) afforded compound Q-6 as a white solid.

Step F: Sodium bis(trimethylsilyl)amide (14.3 mL, 1.0 M in THF) was slowly added to a solution of compound Q-6 (3.0 g) in anhydrous THF (60 mL) at approximately −78° C. After stirring at 0° C. for 1 h, the reaction mixture was cooled to −78° C. and a solution of 2-[N,N-bis(trifluoromethylsulfonyl)amino]-5-chloropyridine (4.12 g) in anhydrous THF (20 mL) was added. The reaction mixture was slowly warmed to ambient temperature overnight. The reaction mixture was cooled to −78° C., quenched by dropwise addition of saturated aqueous sodium hydrogen carbonate and warmed to ambient temperature. The mixture was extracted with ethyl acetate and hexanes twice. The organic phase was washed with brine, dried (sodium sulfate) and concentrated in vacuo to give a crude residue. Purification of the crude residue by flash chromatography over silica gel (gradient elution; 5%-12% ethyl acetate/hexanes as eluent) afforded compound Q-7 as a white solid.

Step G: A mixture of compound Q-7 (4.27 g), TEA (2.66 mL), triphenylphosphine (1.00 g), and palladium acetate (429 mg) in ethanol (20 mL) and DMF (40 mL) was purged for 10 minutes with carbon monoxide. After stirring under an atmosphere of carbon monoxide for 40 h, the volatiles were removed in vacuo and the reaction mixture was diluted with water and extracted with ethyl acetate and hexanes. The organic phase was washed with water and brine, dried (sodium sulfate) and concentrated in vacuo to give a crude residue. Purification of the crude residue by flash chromatography over silica gel (15% ethyl acetate/hexanes as eluent) afforded compound Q-8 as a white solid.

Step H: A mixture of compound Q-8 (2.5 g) and 10% Pd on carbon (145 mg) in ethyl acetate (50 mL) was hydrogenated with a hydrogen balloon at ambient temperature for 1 h. The resulting mixture was filtered and the filtrate was evaporated in vacuo to give compound Q-9 as a white solid.

Step I: Methyllithium (35 mL of a 1.6 N solution in THF) was added to a solution of compound Q-9 (2.1 g) in anhydrous THF (65 mL) at approximately −78° C. After stirring at −78° C. for 2 h, additional methyllithium (10 mL of a 1.6 N solution in THF) was added to the solution at approximately −78° C. After stirring at −78° C. for 1 h the reaction mixture was quenched with saturated aqueous sodium hydrogen carbonate and extracted with ethyl acetate and hexanes. The organic phase was washed with brine, dried (sodium sulfate) and concentrated in vacuo to give a Q-10.

Step J: Concentrated sulfuric acid (4.59 mL) in acetonitrile (100 mL) was added to a solution of compound Q-10 (5.63 mmol) in acetonitrile (100 mL) at ambient temperature. After stirring at ambient temperature for 40 h, the reaction mixture was quenched with small amount of ice and water. Volatiles were removed in vacuo to give a crude residue. This residue was treated with ice, aqueous sodium hydroxide (5.0M, 40 mL), followed by 1,4-dioxane (100 mL) and di-ter-butyl dicarbonate (2.46 g). The mixture was stirred at ambient temperature overnight. Volatiles were removed and the residue was extracted 3 times with ethyl acetate and hexanes. The combined organic layers were washed with brine, dried (sodium sulfate) and concentrated in vacuo to give a residue. Purification of the residue by flash chromatography over silica gel (75% ethyl acetate/hexanes as eluent) afforded a racemic mixture of compound Q-11.

Step J: Solid N-chlorosuccimide (88 mg) was added to a solution of compound Q-11 (134 mg) in DMF (1 mL) at ambient temperature. The mixture was heated in an oil bath (50° C.) for 1.5 h. The reaction mixture was cooled to 0° C. and quenched with saturated aqueous sodium hydrogen carbonate followed by saturated aqueous sodium thiosulfate. The mixture was extracted with ethyl acetate and hexanes. The organic phase was washed with brine, dried (sodium sulfate) and concentrated in vacuo to give a residue. Purification of the residue by flash chromatography over silica gel (gradient elution; 75%-100% ethyl acetate/hexanes as eluent) afforded a racemic mixture of Q-12a and Q-12b. The racemic mixture was resolved on high performance chromatography with ChiralPak AD column (Chiral Pak AD-H 4.6×250 mm 5 u column, flow rate at 0.5 mL/min of 7% ethanol in heptane, and UV detection at 220 nM) to afford two separate enantiomers Q-12a and Q-12b.

Step L: To a solution of amine Q-12a (100 mg) in dichloromethane (0.5 ml) was added HCl (3 ml, 4.0M in dioxane) and stirred at room temperature for 30 minutes. The reaction mixture was concentrated to give compound Q-13a as the HCl salt. ESI-MS calculated for $C_{19}H_{27}ClN_2O$: 334; Found: 335 (M+H).

To a solution of amine Q-12b (31 mg) in dichloromethane (0.3 ml) was added HCl (1.5 ml, 4.0M in dioxane) and stirred at room temperature for 30 minutes. The reaction mixture was concentrated to give compound Q-13b as the HCl salt. ESI-MS calculated for $C_{19}H_{27}ClN_2O$: 334; Found: 335 (M+H).

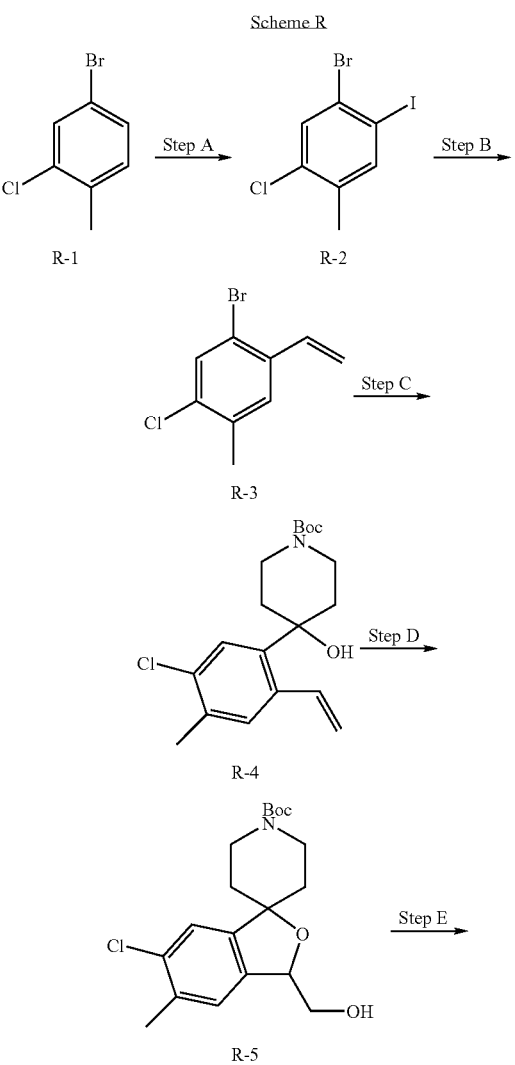

Scheme R

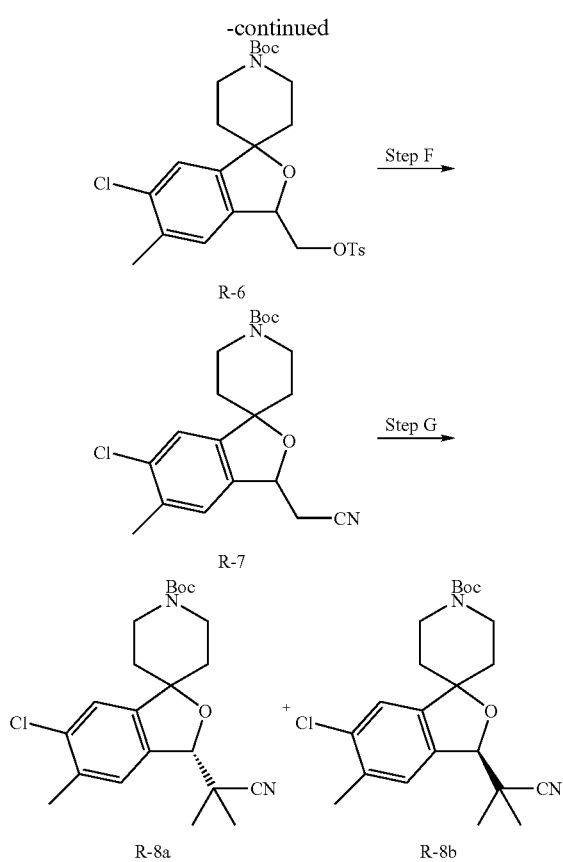

Step A: To a mixture of 4-bromo-2-chlorotoluene R-1 (25.0 g) and trifloroacetic acid (120 mL) was added N-iodosuccinimide (27.4 g) at room temperature and the mixture was stirred for 3 days. The volatiles were removed under vacuum and the residue was purified by flash column chromatograph on silica gel eluting with hexane to give R-2 as white solid. ESI-MS calc. for $C_7H_5BrClI$: 330; Found: 330 (M+).

Step B: To a solution of 4-bromo-2-chloro-5-iodotoluene R-2 (11.5 g) in dimethylformide (120 mL) were added tri-n-butylethyenylstannane (12.1 g), LiCl (4.41 g), [1,3-bis(diphenylphosphino)propane]palladium(II) dichloride (0.616 g), and a few crystals of 2,6-di-tert-butyl-4-methylphenol. The resulting suspension was stirred at room temperature for 3 days and quenched with water (500 μL), followed by extraction with hexane (3×250mL). The organic layers were combined, washed with brine, dried over anhydrous magnesium sulfate, filtered, and concentrated. The resulting residue was purified by a flash column chromatography on silica gel eluting with hexane to yield R-3 as colorless oil. ESI-MS calc. for $C_9H_8BrCl$: 230; Found: 230 (M+).

Step C: A 2.5 M solution of n-butyllithium (13.0 mL) in hexane was added dropwise to a solution of 1-bromo-3-chloro-4-methyl-2-vinylbenzene R-3 (7.50 g) in THF (30 mL) and ether (30 mL) at −78° C. under nitrogen atmosphere. The mixture was stirred for 1 h at −78° C. then 1-t-butoxycarbonyl-4-piperidone (7.10 g) in ether (30 mL) was added at the same temperature. After stirring at −78° C. for 1 h, the mixture was warmed to room temperature and stirred for 6 h. Water was added and the mixture was extracted with ethyl acetate. The extract was washed with brine, dried over anhydrous magnesium sulfate and concentrated under vacuum. The resulting residue was purified by flash column chromatography on silica gel eluting with hexane to 20% ethyl acetate in hexane to give R-4 as a white solid. ESI-MS calc. for $C_{19}H_{26}ClNO_3$: 351; Found: 352 (M+H).

Step D: To a solution of t-butyl 4-hydroxy-4-(5-chloro-4-methyl-2-vinylphenyl)piperidine-1-carboxylate R-4 (6.50 g) in 100 mL of dichloromethane was added 3-chloroperbenzoic acid (6.37 g). The mixture was stirred at reflux overnight, then cooled to room temperature. The mixture was washed with saturated sodium bicarbonate aqueous solution (2×) and brine, dried over anhydrous magnesium sulfate, concentrated. The resulting residue was purified by a flash column chromatograph to give R-5 as white solid. ESI-MS calc. for $C_{19}H_{26}ClNO_4$: 367; Found: 368 (M+H).

Step E: A solution of compound R-5 (1.60 g) in dichloromethane (50 mL), DMAP (0.053 g), and TEA (1.52 mL) was cooled to 0° C., then toluenesulfonyl chloride (0.995 g) was added. The reaction mixture was stirred at 0° C. for 7 h, then slowly warmed up to room temperature and stirred overnight. The volatiles were removed under reduced pressure and the resulting residue was purified by flash column chromatography on silica gel eluted with 15% to 33% ethyl acetate in hexane to give compound R-6. ESI-MS calc. for $C_{26}H_{32}ClNO_6S$: 521; Found: 522 (M+H).

Step F: A mixture of compound R-6 (2.00 g), potassium cyanide (1.25 g), and sodium iodine (0.057 g) in dimethyl sulfoxide (25 mL) was warmed up to 110° C. and stirred overnight. After cooling to room temperature, the mixture was quenched with 250 mL of 1 N sodium hydroxide and extracted with ethyl acetate (3×250 mL). The combined organic layers were washed with brine, dried over anhydrous magnesium sulfate, filtered, and concentrated. The resulting residue was purified by a flash column chromatography on silica gel to give R-7 as white solid. ESI-MS calc. for $C_{20}H_{25}ClN_2O_3$: 376; Found: 377 (M+H).

Step G: To a solution of compound R-7 (1.00 g) in anhydrous THF (10 mL) was added a 1 N solution of sodium bis(trimethylsilyl)amide in THF (7.96 mL) at −78° C. After stirring for 30 min, iodomethane (0.661 mL) was added, and the mixture was stirred for 5 h at −78° C., then slowly warmed up to room temperature and stirred overnight. The volatiles were removed under reduced pressure and the resulting residue was purified with a flash column chromatography on silica gel to give a racemic mixture of R-8a and R-8b. The racemic mixture was resolved on high performance chromatography with ChiralPak OD column (Chiral Pak OD 10×250 mm 5u column, flow rate at 9 mL/min of 0.5% isopropanol in heptane, and UV detection at 220 nM) to afford two separate enantiomers R-8a and R-8b. R-8a: ESI-MS calc. for $C_{22}H_{29}ClN_2O_3$: 404; Found: 405 (M+1H); R-8b: ESI-MS calc. for $C_{22}H_{29}ClN_2O_3$: 404; Found: 405 (M+H).

Scheme S

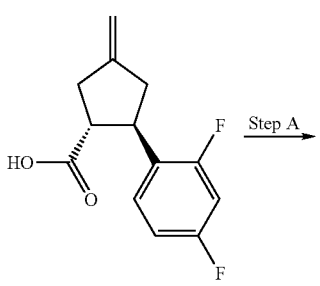

1-5

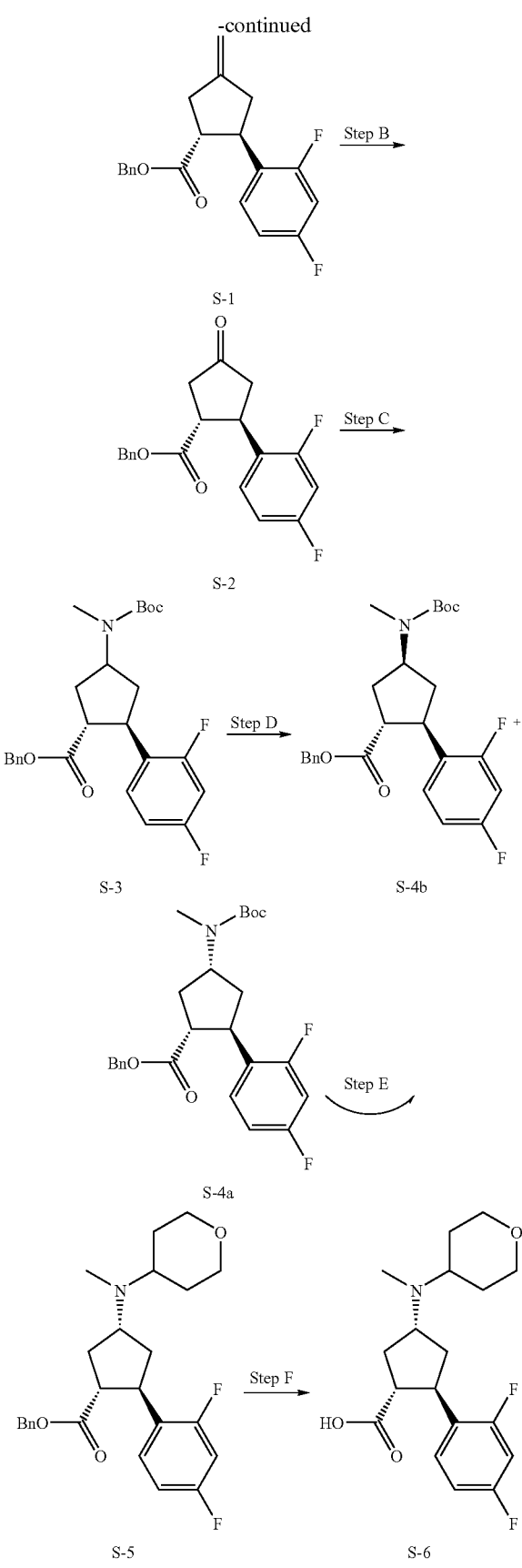

Step A: To a solution of acid 1-5 (6.05 g) in anhydrous CH$_2$Cl$_2$ (100 mL) was added Et$_3$N (4.1 mL). The reaction mixture was cooled to 0° C., then PhCH$_2$OCOCl (1.05 eq., 3.7 mL) was added via a syringe dropwise under N$_2$. After stirring for 5 min at 0° C., solid DMAP (0.1 eq., 310 mg) was added and the reaction was stirred at 0° C. for 1 h. The reaction was quenched by ice, followed by NaHCO$_3$ (sat. aq.). The mixture was extracted with EtOAc/hexanes 3 times. The organic layer was separated, washed with brine, dried over Na$_2$SO$_4$ and concentrated to give the crude product S-1 (6.83 g), which was used in the next step without further purification.

Step B: Ester S-1 (25.4 mmol) was treated with t-BuOH (72 mL) followed by H$_2$O (24 mL) at room temperature. To this mixture was added OsO$_4$ (2.5% in t-BuOH, 3.2 mL) followed by NaIO$_4$ (13.6 g) at 2 min later at room temperature. After stirring 1.5 h at room temperature, the reaction mixture was filtered through celite and the solid was washed with EtOAc (3 times). The filtrate was washed with water and organic layer was separated, then washed with Na$_2$S$_2$O$_3$ (saturated aqueous) followed by brine. The aqueous layer was extracted with EtOAc. Organic layers were combined and washed with Na$_2$S$_2$O$_3$ (saturated aqueous) and brine. The combined organic layers were dried (Na$_2$SO$_4$) and concentrated to give the crude product S-2, which was used the next step without purification.

Step C: A mixture of crude ketone S-3 (25 mmol), molecular sieves (48 g, Aldrich catalog no 233668), MeNH$_2$.HCl (16.9 g) and Et$_3$N (70 mL) in CH$_2$Cl$_2$ (500 mL) was cooled to 0° C. Solid NaBH(OAc)$_3$ (53 g) was added. The bath was removed and the reaction was stirred at RT overnight. The reaction was filtered through celite. The solid was washed with cold 2 N NaOH (two times) followed by CH$_2$Cl$_2$ (two times). The CH$_2$Cl$_2$ layer was separated and the aqueous layer was extracted with CH$_2$Cl$_2$ (3 times). The combined CH$_2$Cl$_2$ layers were dried over Na$_2$SO$_4$ and concentrated to afford a residue, which was dissolved in CH$_2$Cl$_2$ (50 mL). The solution was treated with 2 N NaOH (aq, 20 mL) and Et$_3$N (14 mL, 100 mol, 4 eq.) followed Boc$_2$O (10.9 g) at 0° C. The bath was removed and the reaction was stirred at room temperature for 2 h. The reaction was diluted with water, CH$_2$Cl$_2$ layer was separated and the aqueous layer was extracted with CH$_2$Cl$_2$ (3 times). The combined CH$_2$Cl$_2$ layers were dried over Na$_2$SO$_4$ and concentrated to afford a residue, which was purified (2% EtOAc to 40% EtOAc in Hex) to afford a diastereomeric mixture S-3 (7.3 g, ratio ca. 2:1).

Step D: Compound S-3 was separated with prep Chiral HPLC to afford S-4-a (4.3 g) and S-4-b (2.05 g). Analytical conditions: Chiral OJ 4.6×250 mm 5u column, flow rate at 0.5 mL/min with 20% 2-propanol in heptane, and UV detection at 220 nm, $t_R$(S-4-a) 9.460 min, $t_R$(S-4-b) 14.460 min.

Step E: A solution of S4a (3.75 g) in CH$_2$Cl$_2$ (5 mL) was treated with 4 NHCl in dioxane (30 mL). After 30 min, the mixture was concentrated to afford a residue, which was treated with molecular sieve (16 g, Aldrich catalog no 233668), Et$_3$N (23 mL), tetrahydro-4H-pyran-4-one (4.22 g) and CH$_2$Cl$_2$ (150 mL). To this mixture was added NaBH(OAc)$_3$ (17.9 g). The mixture was stirred at room temperature for 38 h, then worked-up analogous to the work up procedure of Step C. The resulting crude product was dissolved in CH$_2$Cl$_2$, and treated with Et$_3$N (4.7 mL), Boc$_2$O (1.84 g), and NaOH (1N, 20 mL) analogous to Step C. The work-up of this reaction was also analogous to Step C. The resulting crude product was purified by MPLC on silica gel (2% acetone in hexanes to 100% acetone) to give the product S-5.

Step F: A solution of S-5 (200 mg) in 2-propanol (2 mL) was treated with HCl (1M, 0.7 mL, 1.5 eq) followed by Pd/C (10%, 49 mg). The mixture was hydrogenated with a H$_2$

Scheme T

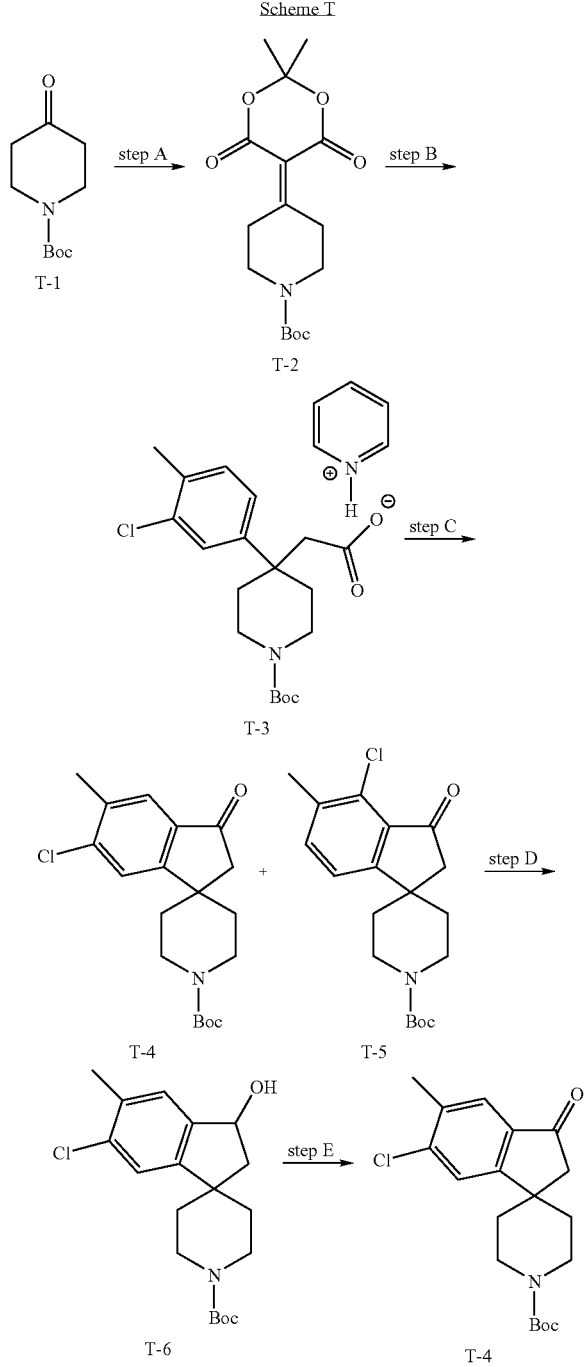

flask was filled with N$_2$ and THF (150 mL), then a solution of 4-bromo-2-chloro-toluene (95.7 g, 0.4658 mol) in THF (300 mL) was added starting with 50 mL, then dropwise, while the internal temperature was maintained below 40° C. The mixture was stirred overnight, then diluted with THF (200 mL) and compound T-2 was added slowly. The temperature was maintained under 40° C. using ice and water. Upon completion of addition, stirring was continued at room temperature for 2 h. Then the reaction mixture was poured into NH$_4$Cl (saturated aqueous, 2 L) and adjusted to pH 5 with 2 N HCl (about 300 mL). The organic layer was separated and the aqueous layer was extracted with toluene twice. The combined organic layers were washed with water, then heated at reflux for 4-5 h. Then the mixture volume was reduced to ~50% by atmospheric distillation until the temperature reached 110° C. The mixture was maintained at reflux for 3 h and stirred at room temperature overnight. Pyridine (35 mL) was added and the mixture was kept at 50° C. for 10 minutes. Crystallization by the addition of heptane afforded compound T-3.

Step C: To a solution of compound T-3 (22.2 g) in CH$_2$Cl$_2$ (200 mL) was added (COCl)$_2$ (2.0 M in CH$_2$Cl$_2$, 37.3 mL) via syringe at 0° C. The reaction was allowed to stir at room temperature for 1.5 h. AlCl$_3$ was added in 2 batches (10 g each, 5 min apart) at 0° C. The reaction was kept at 0° C. for 2 h, then ice was added piece by piece to quench the reaction. To the mixture was added NaOH (aq., 2.5N, 400 mL) at 0° C., Et$_3$N (30 mL), Boc$_2$O (16.3 g), and the mixture was stirred at room temperature overnight. Aqueous workup and extraction with ethyl acetate afforded the crude product as a mixture of T4 and T-5, which was used in the next step without purification.

Step D: To a solution of crude mixture of T4 and T-5 (assume 49.7 mmol) in MeOH (200 mL) was added NaBH$_4$ (1.88 g, 1 eq) in one batch at 0° C. After 30 min at 0° C., the reaction was quenched with NaOH (aq., 2N, 100 mL). Most MeOH was removed in vacuo. The reaction mixture was extracted with 3 times with CH$_2$Cl$_2$. The combined CH$_2$Cl$_2$ layers were dried (Na$_2$SO$_4$) and purified via MPLC (silica, 25% EtOAc in hexane to 100% EtOAc) to afford alcohol T-6.

Step E: Alcohol T-6 (9.57 g) was dissolved in CH$_2$Cl$_2$ (35 mL) and cooled in an ice-water bath. 2,2,6,6-Tetramethyl-1-piperidinyloxy free radical (43 mg) was added as a solution in CH$_2$Cl$_2$ (0.5 mL), followed by KBr (1.0 M aq., 2.7 mL). Commercial bleach (Chlorox®, 6% NaOCl, 0.81 M, 50.6 mL) was diluted with water (50.6 mL) and treated with solid NaHCO$_3$ (5.7 g). The bleach mixture was added to the alcohol solution at 0° C. After 10 minutes, the reaction was quenched with NaOH (1 N, 100 mL). The mixture was extracted with CH$_2$Cl$_2$ (3×100 mL) and the combined CH$_2$Cl$_2$ layers were dried (Na$_2$SO$_4$) to give a crude product. The crude product was purified by MPLC (silica, gradient 5% EtOAc in hexane to 100% EtOAc) to give ketone T-4.

Step A: To a mixture of N-(tert-butoxycarbonyl)-4-piperidone T-1 (100 g, 0.502 mol), Meldrum's acid (79.6 g, 0.552 mol), ethyl acetate (1000 mL) and triisopropyl borate (231 mL, 1.004 mol) was added NH$_4$OH (8.4 mL) and acetic acid (5.8 mL). The reaction mixture was stirred at room temperature under N$_2$ overnight. The reaction was cooled in an ice bath for 1 h and filtered to give a solid, which was washed with ethyl acetate and dried to afford T-2.

Step B: Mg turnings (11.3 g) in a flask with a rubber septum were stirred vigorously under high vacuum for 2-3 h. The

EXAMPLE 1

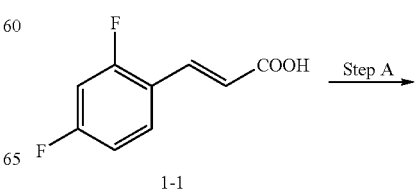

1-1

-continued

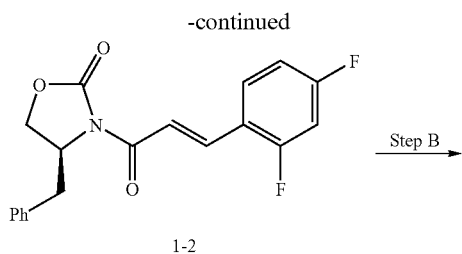
1-2

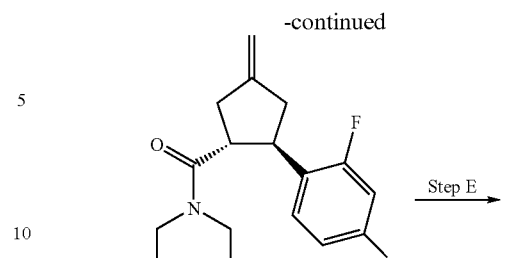
1-6

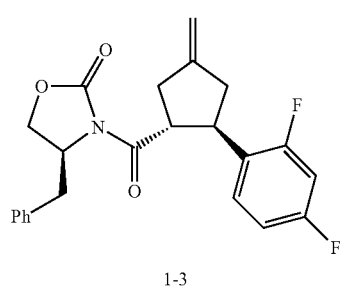
1-3

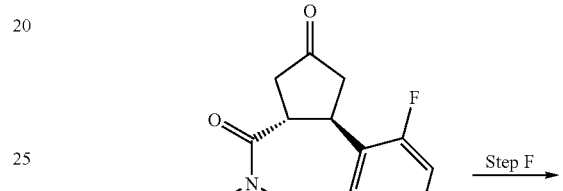

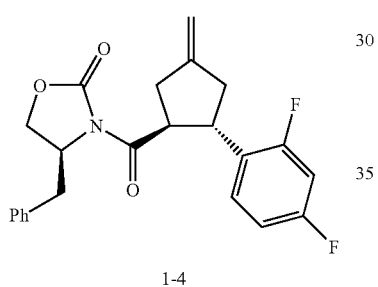
1-4

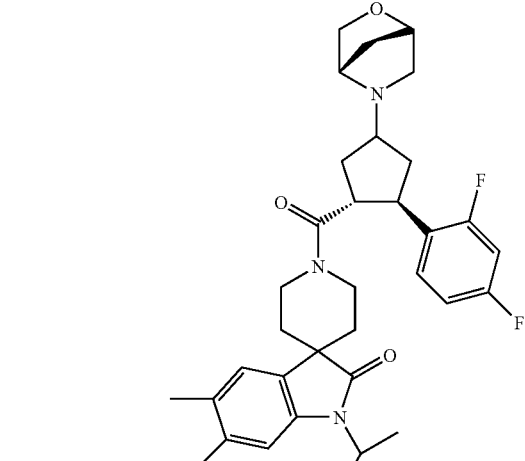
1-7

1-3 →Step C→ 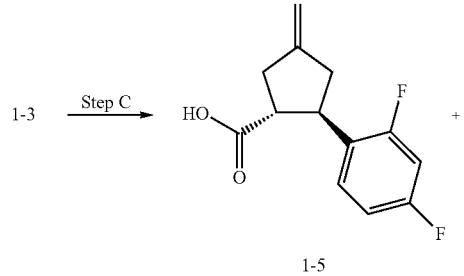
1-5

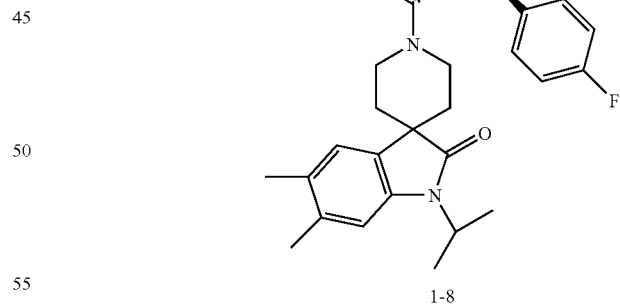
1-8

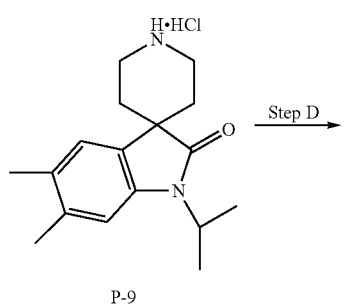
P-9

Step A: To a solution of trans-2,4-difluorocinnamic acid 1-1 (7.6 g) in THF (150 mL) was added TEA (17.3 mL). The reaction mixture was cooled to −40° C. and trimethyl acetic chloride (5.1 mL) was added slowly. The reaction mixture was stirred at −40° C. for 2 hrs, then lithium chloride (1.93 g) was added, followed by s-4-benzyl-2-oxazolidinone (7.31 g). After stirring at −40° C. for 20 minutes, reaction mixture was allowed to warm up to room temperature and stirred at rt for 18 hrs. The reaction mixture was then poured into saturated aqueous ammonium chloride (180 mL); the phases were separated and the aqueous phase was extracted with ethyl acetate. The combined organic extracts were washed with brine, dried over MgSO$_4$ and concentrated to give a residue. The resulting residue was purified by crystallization from EtOAc/hexane to give compound 1-2. ESI-MS calc. for C$_{19}$H$_{15}$F$_2$NO3: 343; Found: 344 (M+H), 366 (M+Na).

Step B: To a solution of Compound 1-2 (2.3 g) in THF (30 mL) was added palladium acetate (73.6 mg) and 2-[(trimethylsilyl)methyl]-2-propenol-yl acetate (1.8 mL), then the reaction vessel was evacuated under vacuum and purged with nitrogen 3 times, then triisopropyl phosphate (0.45 mL) was added. The reaction mixture was heated at 65° C. for 18 hrs, then cooled to rt and the solvent was removed. The resulting residue was partitioned between ethyl acetate and water, the aqueous layer was extracted with ethyl acetate. The combined organic extracts were washed with brine, dried over MgSO$_4$ and concentrated to give a residue. The resulting residue was purified by flash column chromatography on silica gel (2-30% ethyl acetate in hexane) to give yellow oil 1-4 (fast elusion) and white solid 1-3 (slow elusion). ESI-MS calc. for C$_{23}$H$_{21}$F$_2$NO$_3$: 397; Found: 398 (M+H), 420 (M+Na).

Step C: To a solution of Compound 1-3 (1.7 g) in THF (24 mL) and water (6 mL) under nitrogen at 0° C. was added lithium hydroxide mono hydrate (0.36 g) and H$_2$O$_2$ (30% solution, 2.5 mL). The reaction mixture was stirred at 0° C. for 30 minutes, then warmed up to rt and stirred for 1.5 hrs. The solvent was removed, the pH was adjusted to pH 9-10 with saturated NaHCO$_3$, and the solution was extracted with CH$_2$Cl$_2$. The pH of the aqueous layer was adjusted to pH 1-2 with 2N HCl and the solution was extracted with CH$_2$Cl$_2$. The combined organic layers were dried over MgSO$_4$ and concentrated to give a colorless oil D-5. ESI-MS calc. for C$_{13}$H$_{12}$F$_2$O$_2$: 238; Found: 239 (M+H).

Step D: To a solution of compound 1-5 (0.17 g) in dichloromethane (15 mL) was added NMM (0.11 mL), HOBt (0.096 g), EDC (0.187 g) and amine P-9 (0.20 g). The reaction mixture was stirred at room temperature overnight, diluted with dichloromethane, and washed with water and brine. The organic layer was dried over anhydrous magnesium sulfate, filtered, and concentrated to give compound 1-6 (0.32 g). ESI-MS calc. for C$_{30}$H$_{34}$F$_2$N$_2$O$_2$: 492; Found: 493 (M+H).

Step E: To a solution of Compound 1-6 (0.32 g) in THF (10 mL) and water (10 mL) at room temperature was added OsO4 (2.5 wt % solution in t-BuOH, 0.87 mL). After stirring the reaction mixture at r.t. for 10 minutes, sodium periodate (0.443 g in 4.5 mL H$_2$O) was added slowly over 15 minutes, and the mixture was stirred for 1.5 hrs. Then sodium thiosulfate pentahydrate (0.51 g, saturated) was added, and the reaction mixture was stirred for an additional 15 minutes. The layers were separated, the aqueous layer was extracted with EtOAc, dried over MgSO$_4$, filtered and concentrated to give 1-7 (0.32 g) as a black solid. ESI-MS calc. for C$_{29}$H$_{32}$F$_2$N$_2$O$_3$: 494; Found: 495 (M+H).

Step F: To a solution of 2-oxa-5-azabicyclo[2.2.1]heptane hydrochloride (13.7 mg) in dichloromethane 32 mL) was added TEA (0.0282 mL). After stirring at room temperature for 10 minutes, Compound 1-7 (50 mg) and acetic acid (0.012 mL) were added. The reaction mixture was stirred at room temperature for 10 minutes, followed by the addition of sodium triacetoxyborohydride (85.8 mg). After stirring 18 hours, the reaction mixture was diluted with CH$_2$Cl$_2$, washed with saturated NaHCO$_3$ and brine, dried over anhydrous sodium sulfate, filtered and concentrated to give a residue. The resulting residue was purified by prep TLC (CHCl$_3$:2N NH$_3$ in CH$_3$OH=10:1) to give compound 1-8 (34 mg). ESI-MS calc. for C$_{35}$H$_{41}$F$_2$N$_3$O$_3$: 578; Found: 579 (M+H). $^1$H NMR (500 HMz, CD$_3$OD): 7.6-7.3 (m, 1H), 7.0-6.9 (m, 4H), 4.6-4.4 (m, 2H), 4.2-4.0 (m, 2H), 4.0-3.8 (m, 3H), 3.8-3.6 (m, 5H), 3.6-3.4 (m, 2H), 3.0-2.95 (m, 1H), 2.8-2.6 (m, 1H), 2.4-2.3 (m, 1H), 2.25 (s, 3H), 2.22 (s, 3H), 2.2-2.1 (m, 1H), 2.05-1.95 (m, 1H), 1.95-1.82 (m, 1H), 1.8-1.45 (m, 3H), 1.42 (d, 6H), 1.05-0.95 (m, 1H)

The following compounds were prepared using the appropriate amine and intermediate 1-7 following procedures similar to that described above for Example 1, Step F:

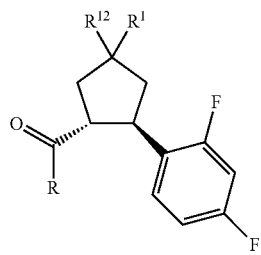

| Example | R | R$^1$ | R$^{12}$ | Calculated MW | Parent Ion m/z (M + H) ESI-MS |
|---|---|---|---|---|---|
| 2 | | F, F mixture | H | C$_{34}$H$_{41}$F$_4$N$_3$O$_2$ 600 | 601 |

-continued
| Example | R | R[1] | R[12] | Calculated MW | Parent Ion m/z (M + H) ESI-MS |
|---|---|---|---|---|---|
| 3 | (1-methyl-5,6-dimethyl-N-isopropyl-spirooxindole-piperidine) | 3,3-difluoro-1-methylpiperidine (F, F) | H | $C_{34}H_{41}F_4N_3O_2$ 600 mixture | 601 |
EXAMPLE 4
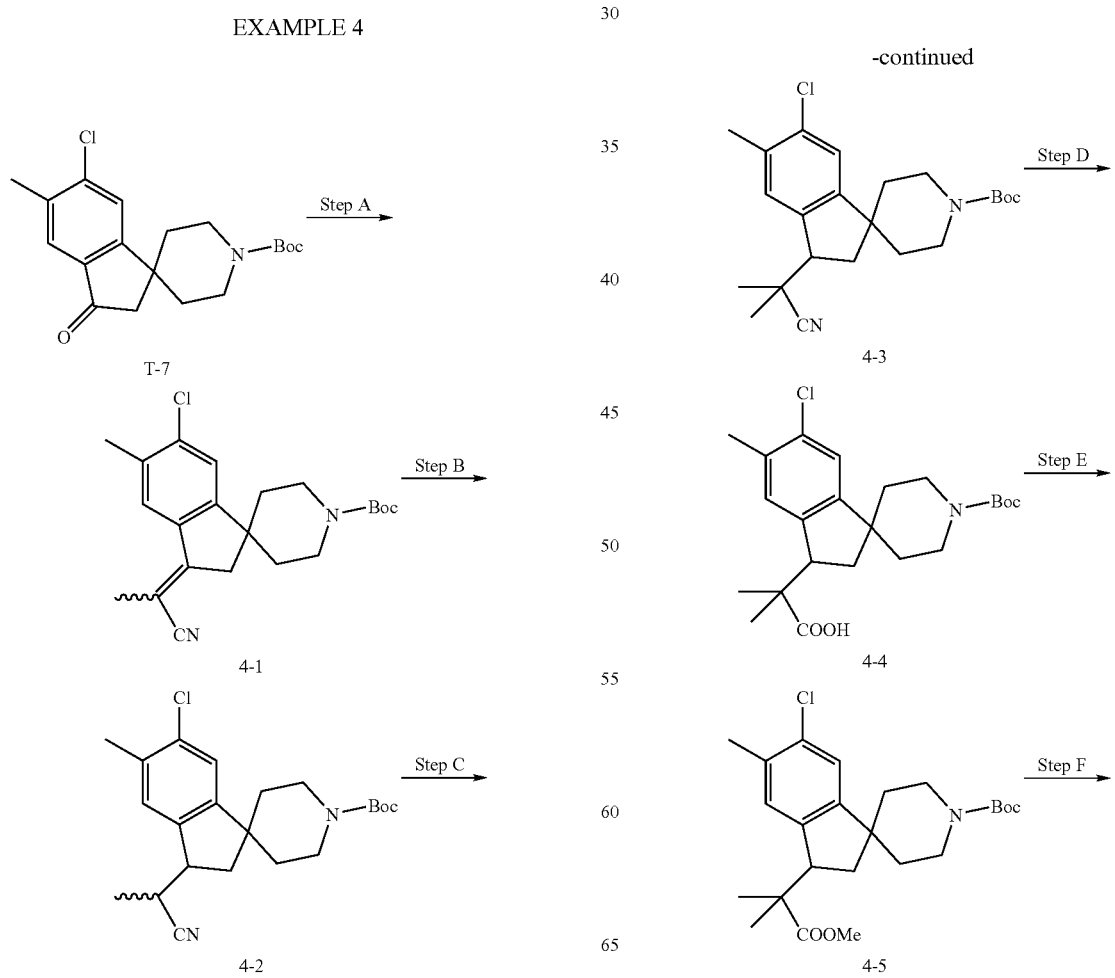

-continued
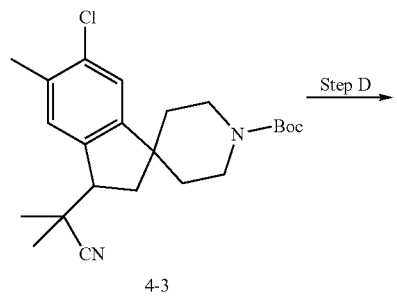
4-3
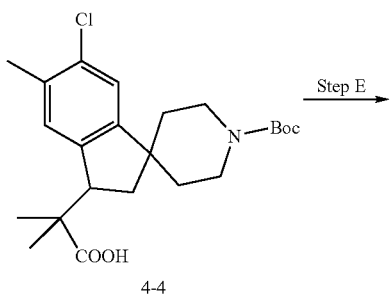
4-4
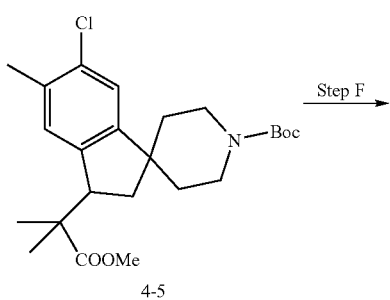
4-5
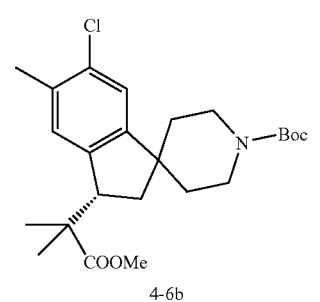
4-6a
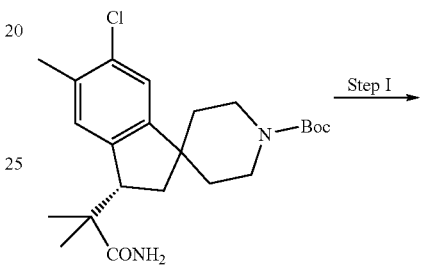
4-6b
-continued
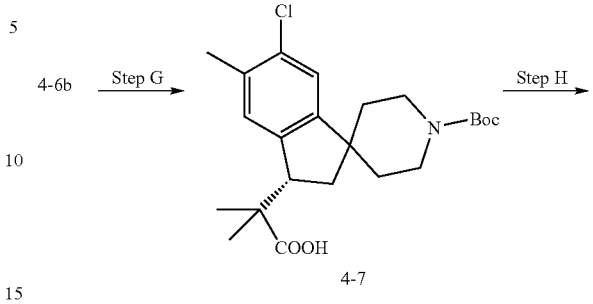
4-7
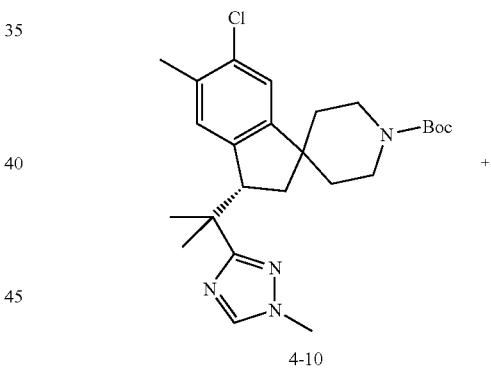
4-8
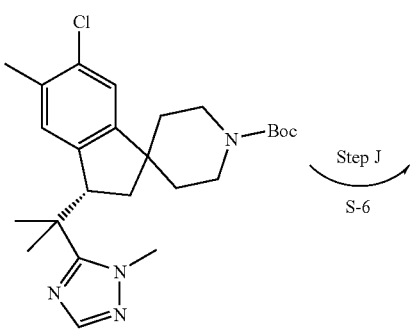
4-10
4-9

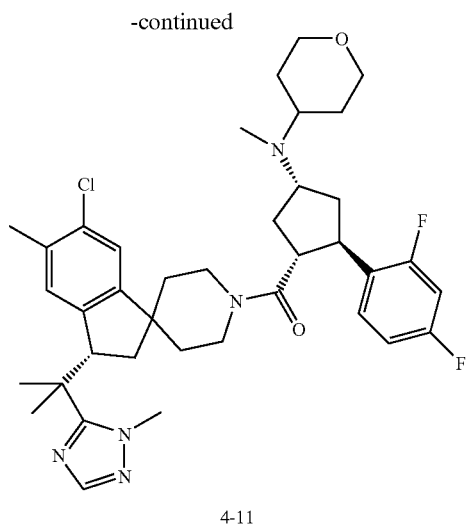

4-11

Step A: To a suspension of NaH (60% in mineral oil, 4.40 g) in THF (100 mL) was added diethyl (1-cyanoethyl) phosphonate (23 g) in THF (65 mL) at 0° C. The mixture was warmed to room temperature and heated to reflux for 15 min. The reaction flask was lifted from the oil bath and ketone T-7 (12.7 g) was added as a solution in THF (65 mL). The mixture was heated to reflux overnight. The reaction was cooled to 0° C. and quenched by NaHCO$_3$ (saturated aqueous). Most THF was removed in vacuo and the mixture was partitioned between EtOAc-hexanes and water. The organic layer was separated and the aqueous layer was extracted one more time with EtOAc-Hexanes. The combined organic layers were washed with brine and dried (Na$_2$SO$_4$). Removal of the solvent in vacuo afforded nitrile 4-1 as a mixture of geometric isomers, which was used in the next step without further purification.

Step B: To a solution of nitrile 4-1 (obtained in Step A) in MeOH (160 mL) were added Mg turnings (3.50 g) at room temperature. After 1 h of vigorous stirring at room temperature, gas bubbles were observed and the reaction flask became warm. The reaction mixture was cooled with an ice-water bath for about 20 min. The cold bath was removed and the reaction mixture was stirred at room temperature for 2 h. To this solution was added an additional portion of Mg turnings (0.5 g) at room temperature. After 1 additional hour at room temperature, the reaction was poured into a mixture of ice, 2 N HCl (aq.) and EtOAc. The mixture was stirred until all of the ice melted. The mixture was extracted with EtOAc/hexanes (3 times). The combined organic extracts were washed with NaHCO$_3$ (saturated aqueous), brine and dried (Na$_2$SO$_4$) to afford an oil, which was purified on silica gel with a gradient of 5% EtOAc in hexanes to 100% EtOAc in hexanes to give the nitrile 4-2 as a diastereomeric mixture.

Step C: To a solution of diisopropylamine (12 mL) in THF (100 mL) was added n-BuLi (2.5 M in hexanes, 30 mL) at 0° C. The mixture was stirred at 0° C. for 30 min. To this solution was added nitrile 4-2 (36.4 mmol, obtained above, azeotroped with toluene once) in THF (40 mL) 0° C. The mixture was stirred at 0° C. for 45 min. To this mixture was added a mixture of MeI (4.65 mL) and HMPA (13 mL) at 0° C. The reaction mixture was stirred at 0° C. for 1 hr, cooled to −78° C. and quenched by dropwise addition of NH$_4$Cl (sat. aq.). The mixture was partitioned between EtOAc-hexanes and water. The organic layer was separated and the aqueous layer was extracted with EtOAc-hexanes once more. The combined organic layers were washed with brine and dried (Na$_2$SO$_4$). Evaporation of the solvent afforded crude nitrile 4-3, which was used in the next step.

Step D: Nitrile 4-3 obtained above was azeotroped with toluene, and the resulting residue was treated with concentrated HCl (100 mL) and heated to reflux overnight. Additional conc. HCl (100 mL) was added and reflux continued overnight. More concentrated HCl (100 mL) was added and the reaction was stirred at room temperature over the weekend. Heating to reflux was resumed and continued for 2 additional days. Volatiles were removed in vacuo and the residue was treated with ice (50 g), NaOH (5N, 200 mL) 1,4-dioxane (200 mL) and di-tert-butyl dicarbonate (13.9 g). The mixture was stirred at room temperature overnight. Additional di-tert-butyl dicarbonate (5.5 g) was added and the mixture was stirred at room temperature for 1 hour. The layers were separated and concentrated separately. The crude material from each layer was combined, and the residue was treated with ice and 2 N HCl (aq.). The mixture was extracted with CH$_2$Cl$_2$ (3 times), and the combined organic layers were dried (Na$_2$SO$_4$) and concentrated to give a solid, which was purified on silica gel with a gradient of 5% acetone/CH$_2$Cl$_2$ to 50% acetone/CH$_2$Cl$_2$ to give acid 4-4.

Step E: To a suspension of acid 4-4 (10.0 g) in CH$_3$OH (100 mL) was added (trimethylsilyl)diazomethane (2.0 M in diethyl ether, 50 mL) at 0° C. Upon addition, the ice water bath was removed and the reaction was stirred at room temperature for 2 hours. Additional (trimethylsilyl)diazomethane (2.0 M in diethyl ether, 30 mL) was added at 0° C., and the reaction was then stirred another hour at room temperature. The reaction mixture was concentrated and purified on silica gel with a gradient of 5% EtOAc in hexanes to 75% EtOAc in hexanes to give the ester 4-5 as a racemic mixture.

Step F: Chiral resolution of the racemic mixture of compound 4-5 was carried out with ChiralCel OJ column (10% MeOH in SCF CO$_2$). With ChiralCel OJ 4.6×250 mm column, flow rate at 2.11 mL/min of 10% MeOH in SCF CO$_2$, and UV detection at 220 nM, the retention times of the fast eluting enantiomer 4-6a and the slow eluting enantiomer 4-6b are 2.417 min and 3.071 min, respectively.

Step G: To a solution of compound 4-6a (2.95 g) in 50 mL of THF/MeOH/H$_2$O (2.5:1:1) was added LiOH.H$_2$O (2.3 g). The solution was heated overnight in an oil bath (80° C.). The next day, additional LiOH.H$_2$O (0.8 g) was added and heating continued overnight. The mixture was concentrated in vacuo. The residue was treated with ice and 2 N HCl. The mixture was extracted with CH$_2$Cl$_2$ (3 times). The combined organic layers were dried (Na$_2$SO$_4$) and concentrated to give a solid, which was purified on silica gel with a gradient of 5% acetone in CH$_2$Cl$_2$ to 50% acetone in CH$_2$Cl$_2$ to give acid 4-7.

Step H: To a solution of compound 4-7 (100 mg) in DMF (3 mL) was added 1-hydroxy-7-azabenzotriazole (49 mg) and 1-(3-dimethylaminopropyl)-3-ethylcarbodiimide (68.3 mg) at room temperature. The reaction mixture was stirred overnight. The following day, the reaction mixture was cooled with an ice water bath, and ammonium hydroxide (14.8 N, 0.17 mL) was added. The cold bath was removed after 30 minutes, and the resulting mixture was stirred at room temperature for 90 minutes. The mixture was diluted with water and extracted 3 times with EtOAc. The combined organic layers were washed with water, 1N HCl (aq.), 1N NaOH (aq.), brine and dried (Na$_2$SO$_4$) to give a crude residue, which was purified by silica gel prep TLC (40% acetone in hexanes) to afford amide 4-8.

Step I: A suspension of compound 4-8 (790 mg) in DMF dimethyl acetal (1 mL) was heated in an oil bath (120° C.) for 2 hours. The reaction flask was removed from the oil bath and concentrated in vacuo by azeotroping with toluene. The resulting oil was then placed on a vacuum pump for 90 minutes. The crude material was suspended in acetic acid (8 mL), and methyl hydrazine (0.1 µL) was added at room temperature. The reaction mixture was heated on an oil bath (90° C.) for 75 minutes, then concentrated in vacuo by azeotroping with toluene. The resulting crude oil was dissolved in $CH_2Cl_2$ (10 mL) and treated with $Et_3N$ (3 mL), 2N NaOH (5 mL) and di-tert-butyl dicarbonate (165 mg). The mixture was stirred overnight at room temperature. The reaction mixture was diluted with water and extracted 3 times with $CH_2Cl_2$. The combined organic layers were dried ($Na_2SO_4$) and purified over silica gel with a gradient of 5% acetone in hexanes to 60% acetone in hexanes to give fast eluting triazole (major isomer) 4-9 and slow eluting triazole (minor isomer) 4-10.

Step J: A solution of compound 4-9 (135 mg) in $CH_2Cl_2$ (3 mL) was treated with HCl (4 M in 1,4-dioxane, 7 mL) at room temperature. The resulting mixture was stirred at room temperature for 20 minutes. The mixture was concentrated in vacuo to give a crude residue. A mixture of this residue, acid S-6 (133 mg), HATU (134.6 mg), HOAT (48.2 mg) and 4-methylmorpholine (160 mL) in $CH_2Cl_2$ (10 mL) was stirred at room temperature overnight. The volatiles were removed to afford a residue, which was purified with HPLC on a C18 reversed phase column with a gradient 10% to 55% of water (0.1% TFA) and acetonitrile (0.1% TFA) and lypholized to afford compound 4-11. $^1$H NMR (500 MHz, $CD_3OD$): δ 7.86 (m, 1H), 7.47 (q, 0.67H), 7.30 (q, 0.33H), 7.11 (s, 0.33H), 7.03 (q, 1.33H), 6.91 (t, 0.67H), 6.71 (s, 0.67H), 6.2 (m, 1H) 4.51 (m, 1H), 4.02 (m, 5H), 3.9 (d, 1H), 3.74 (m, 2H), 3.57 (m, 0.67H), 3.49 (m, 0.33H), 3.42 (t, 2H), 3.13 (t, 0.67H), 3.02 (m, 1.33H), 2.76 (m, 1H), 2.42 (s, 3H), 2.31 (m, 3H), 2.16 (s, 3H), 2.08 (m, 2H), 1.89 (t, 0.33H), 1.79 (m, 2H), 1.70 (m, 2.67H), 1.48 (m, 2H), 1.40 (m, 6H), 1.25 (m, 1.33H), 1.16 (t, 0.67H) 0.88 (t, 1H)

The following compounds were prepared using the appropriate starting materials and reagents following procedures similar to that described above for Example 1 and Example 4:

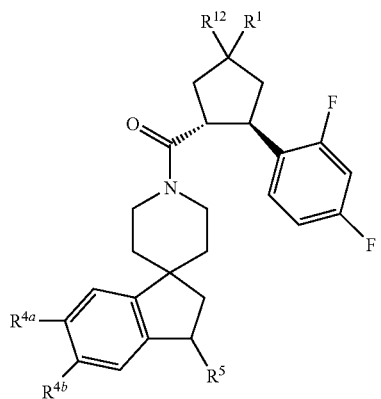

| Example | $R^{4a}$ | $R^{4b}$ | $R^5$ | $R^1$ | $R^{12}$ | Calculated MW | Parent Ion m/z (M + H) ESI-MS |
|---|---|---|---|---|---|---|---|
| 5 | Cl | $CH_3$ | (cyclobutyl with gem-diF, ketone, t-Bu) | (oxa-azabicyclic, N-Me) | H | $C_{38}H_{44}ClF_4N_3O_3$ 701 | 702.29 |
| 6 | Cl | $CH_3$ | (N-methyltriazole, t-Bu) | (oxa-azabicyclic, N-Me) | H | $C_{37}H_{44}ClF_2N_5O_2$ 663 | 664.49 |
| 7 | Cl | $CH_3$ | (N-methyltriazole, t-Bu) | (3-fluoropyrrolidine, N-Me) | H | $C_{36}H_{43}ClF_3N_5O$ 653 | 654.50 |

-continued

| Example | R⁴ᵃ | R⁴ᵇ | R⁵ | R¹ | R¹² | Calculated MW | Parent Ion m/z (M + H) ESI-MS |
|---|---|---|---|---|---|---|---|
| 8 | Cl | CH₃ | pivaloyl methylamide | 2-oxa-5-azabicyclo[2.2.1]heptane (N-methyl) | H | $C_{36}H_{44}ClF_2N_3O_3$ 639 | 640.20 |
| 9 | Cl | CH₃ | pivaloyl methylamide | 4-(dimethylamino)tetrahydropyran | H | $C_{37}H_{48}ClF_2N_3O_3$ 655 | 656.22 |
| 10 | Cl | CH₃ | 3-tert-butyl-1-methyl-1,2,4-triazol-5-yl | 4-(dimethylamino)tetrahydropyran | H | $C_{38}H_{48}ClF_2N_5O_2$ 679 | 680.26 |
| 11 | Cl | CH₃ | 3-tert-butyl-1-methyl-1,2,4-triazol-5-yl | (3-hydroxy-1-methylpyrrolidinium) TFA | H | $C_{36}H_{44}ClF_2N_5O_2$ 651 | 652.20 |
| 12 | Cl | CH₃ | 3-tert-butyl-1-methyl-1,2,4-triazol-5-yl | 4-methylpiperazin-1-yl (N-methyl) | H | $C_{37}H_{47}ClF_2N_6O$ 664 | 655.22 |
| 13 | Cl | CH₃ | 3-tert-butyl-1-methyl-1,2,4-triazol-5-yl | 4-hydroxy-1-methylpiperidine | H | $C_{37}H_{46}ClF_2N_5O_2$ 665 | 666.24 |

-continued

| Example | R⁴ᵃ | R⁴ᵇ | R⁵ | R¹ | R¹² | Calculated MW | Parent Ion m/z (M + H) ESI-MS |
|---|---|---|---|---|---|---|---|
| 14 | Cl | CH₃ | 5-tert-butyl-1-methyl-1H-1,2,4-triazol-3-yl | 4-(methylamino)tetrahydro-2H-pyran-4-yl | H | C₃₇H₄₆ClF₂N₅O₂  665 | 666.22 |
| 15 | Cl | CH₃ | 5-tert-butyl-1-methyl-1H-1,2,4-triazol-3-yl | 2-(dimethylamino)ethanol | H | C₃₅H₄₄ClF₂N₅O₂  639 | 640.21 |
| 16 | Cl | CH₃ | 5-tert-butyl-1-methyl-1H-1,2,4-triazol-3-yl | 2-[(2-hydroxyethyl)(methyl)amino]ethanol | H | C₃₆H₄₆ClF₂N₅O₃  669 | 670.20 |
| 17 | Cl | CH₃ | 5-tert-butyl-1-methyl-1H-1,2,4-triazol-3-yl | 2-(methylamino)ethanol | H | C₃₄H₄₂ClF₂N₅O₂  625 | 626.18 |
| 18 | Cl | CH₃ | 5-tert-butyl-1-methyl-1H-1,2,4-triazol-3-yl | N-methyl-tetrahydro-2H-pyran-4-amine | H | C₃₈H₄₈ClF₂N₅O₂  679 | 680.43 |
| 19 | Cl | CH₃ | 2-methyl-1-(methylamino)-1-oxopropan-2-yl | N-methyl-tetrahydro-2H-pyran-4-amine | H | C₃₇H₄₈ClF₂N₃O₃  655 | 656.37 |

-continued

| Example | R4a | R4b | R5 | R1 | R12 | Calculated MW | Parent Ion m/z (M + H) ESI-MS |
|---|---|---|---|---|---|---|---|
| 20 | Cl | CH3 | *t*-Bu-oxadiazole-methyl | tetrahydropyran-4-yl-N(CH3) | H | $C_{38}H_{47}ClF_2N_4O_3$ 680 | 681.43 |
| 21 | Cl | CH3 | pivaloyl-(3R)-hydroxypyrrolidinyl | tetrahydropyran-4-yl-N(CH3) | H | $C_{40}H_{52}ClF_2N_3O_4$ 711 | 712.74 |
| 22 | CH3 | Cl | *t*-Bu-NH-C(O)- | tetrahydropyran-4-yl-N(CH3) | H | $C_{37}H_{48}ClF_2N_3O_3$ 655 | 656.49 |
| 23 | CH3 | Cl | *t*-Bu-NH-C(O)- | tetrahydropyran-4-yl-N(CH3) | H | $C_{37}H_{48}ClF_2N_3O_3$ 655 | 656.48 |
| 24 | Cl | CH3 | *t*-Bu-oxadiazolone | tetrahydropyran-4-yl-N(CH3) | H | $C_{37}H_{45}ClF_2N_4O_4$ 682 | 683.70 |
| 25 | Cl | CH3 | *t*-Bu-(1-methyl-triazol-5-yl) | tetrahydropyran-4-yl-methyl-NH-CH3 | H | $C_{38}H_{48}ClF_2N_5O_2$ 679 | 680.52 |

-continued
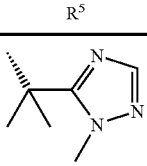
| Example | R⁴ᵃ | R⁴ᵇ | R⁵ | R¹ | R¹² | Calculated MW | Parent Ion m/z (M + H) ESI-MS |
|---|---|---|---|---|---|---|---|
| 26 | Cl | CH₃ | 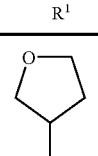 | 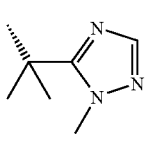 | H | $C_{37}H_{46}ClF_2N_5O_2$ 665 | 666.51 |
| 27 | Cl | CH₃ | 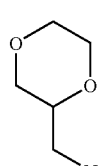 | 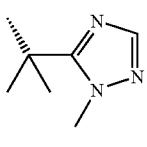 | H | $C_{37}H_{46}ClF_2N_5O_3$ 681 | 682.51 |
| 28 | Cl | CH₃ | 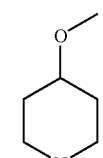 | 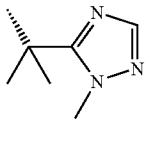 | H | $C_{38}H_{48}ClF_2N_5O_2$ 679 | 680.49 |
| 29 | Cl | CH₃ | 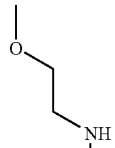 | 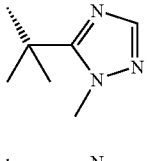 | H | $C_{35}H_{44}ClF_2N_5O_2$ 639 | 640.44 |
| 30 | Cl | CH₃ | 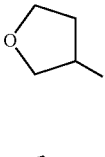 | 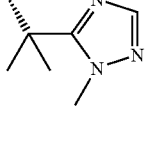 | H | $C_{36}H_{44}ClF_2N_5O_2$ 651 | 652.46 |
| 31 | Cl | CH₃ | | 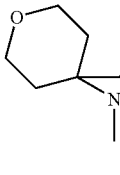 | H | $C_{38}H_{48}ClF_2N_5O_3$ 695 | 696.74 |

-continued

| Example | R⁴ᵃ | R⁴ᵇ | R⁵ | R¹ | R¹² | Calculated MW | Parent Ion m/z (M + H) ESI-MS |
|---|---|---|---|---|---|---|---|
| 32 | Cl | CH₃ | tert-butyl-2-methyl-1,3,4-oxadiazole | tetrahydropyran-4-yl-NH | H | $C_{37}H_{45}ClF_2N_4O_2$ 666 | 667.74 |
| 33 | Cl | CH₃ | tert-butyl-1-methyl-1,2,4-triazole | tetrahydropyran-4-yl-NH | H | $C_{37}H_{46}ClF_2N_5O_2$ 665 | 666.78 |
| 34 | Cl | CH₃ | tert-butyl-1-methyl-1,2,4-triazole | tetrahydropyran-4-yl-N(CH₃) | H | $C_{38}H_{48}ClF_2N_5O_2$ 679 | 680.44 |
| 35 | Cl | CH₃ | tert-butyl-1-ethyl-1,2,4-triazole | tetrahydropyran-4-yl-N(CH₃) | H | $C_{39}H_{50}ClF_2N_5O_2$ 693 | 694.41 |
| 36 | Cl | CH₃ | C(CH₃)₂C(O)NHEt | tetrahydropyran-4-yl-N(CH₃) | H | $C_{38}H_{50}ClF_2N_3O_3$ 669 | 670.69 |
| 37 | Cl | CH₃ | C(CH₃)₂C(O)NH₂ | tetrahydropyran-4-yl-N(CH₃) | H | $C_{36}H_{46}ClF_2N_3O_3$ 641 | 642.66 |
| 38 | Cl | CH₃ | C(CH₃)₂NHC(O)CH₃ | tetrahydropyran-4-yl-N(CH₃) | H | $C_{37}H_{48}ClF_2N_3O_3$ 655 | 656.43 |

-continued

| Example | R⁴ᵃ | R⁴ᵇ | R⁵ | R¹ | R¹² | Calculated MW | Parent Ion m/z (M + H) ESI-MS |
|---|---|---|---|---|---|---|---|
| 39 | Cl | CH₃ | pyrrolidine with pivaloyl and OH | tetrahydropyran-4-yl N-methyl | H | C₄₀H₅₂ClF₂N₃O₄ 711 | 712.70 |
| 40 | Cl | CH₃ | t-butyl-NH-acetyl | tetrahydropyran-4-yl N-methyl | H | C₃₇H₄₈ClF₂N₃O₃ 655 | 656.43 |
| 41 | Cl | CH₃ | morpholine with pivaloyl | tetrahydropyran-4-yl N-methyl | H | C₄₀H₅₂ClF₂N₃O₄ 711 | 712.70 |
| 42 | Cl | CH₃ | t-butyl-oxadiazole-methyl | tetrahydropyran-4-yl NH-methyl | CH₃ | C₃₈H₄₇ClF₂N₄O₃ 680 | 681.39 |
| 43 | Cl | CH₃ | t-butyl-oxadiazole-NH₂ | tetrahydropyran-4-yl N-methyl | H | C₃₇H₄₆ClF₂N₅O₃ 681 | 682.71 |
| 44 | Cl | CH₃ | t-butyl-oxadiazole-methyl | tetrahydropyran-4-yl N-dimethyl | CH₃ | C₃₉H₄₉ClF₂N₄O₃ 694 | 695.44 |

| Example | R⁴ᵃ | R⁴ᵇ | R⁵ | R¹ | R¹² | Calculated MW | Parent Ion m/z (M + H) ESI-MS |
|---|---|---|---|---|---|---|---|
| 45 | Cl | CH₃ | (t-Bu-oxadiazole-CH₃) | (oxabicyclic amine) | H | $C_{37}H_{43}ClF_2N_4O_3$ 664 | 665.64 |
| 46 | Cl | CH₃ | (t-Bu-oxadiazole-NH₂) | (oxabicyclic amine) | H | $C_{36}H_{42}ClF_2N_5O_3$ 665 | 666.63 |
*mixture means a mixture of stereoisomers at the carbon of attachment
EXAMPLE 47
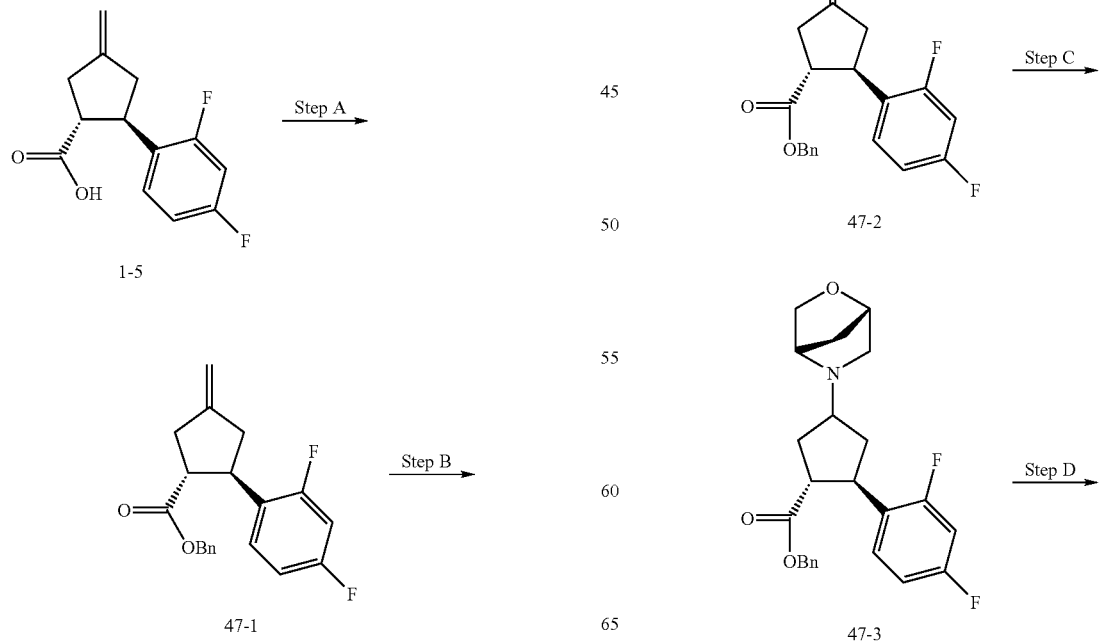

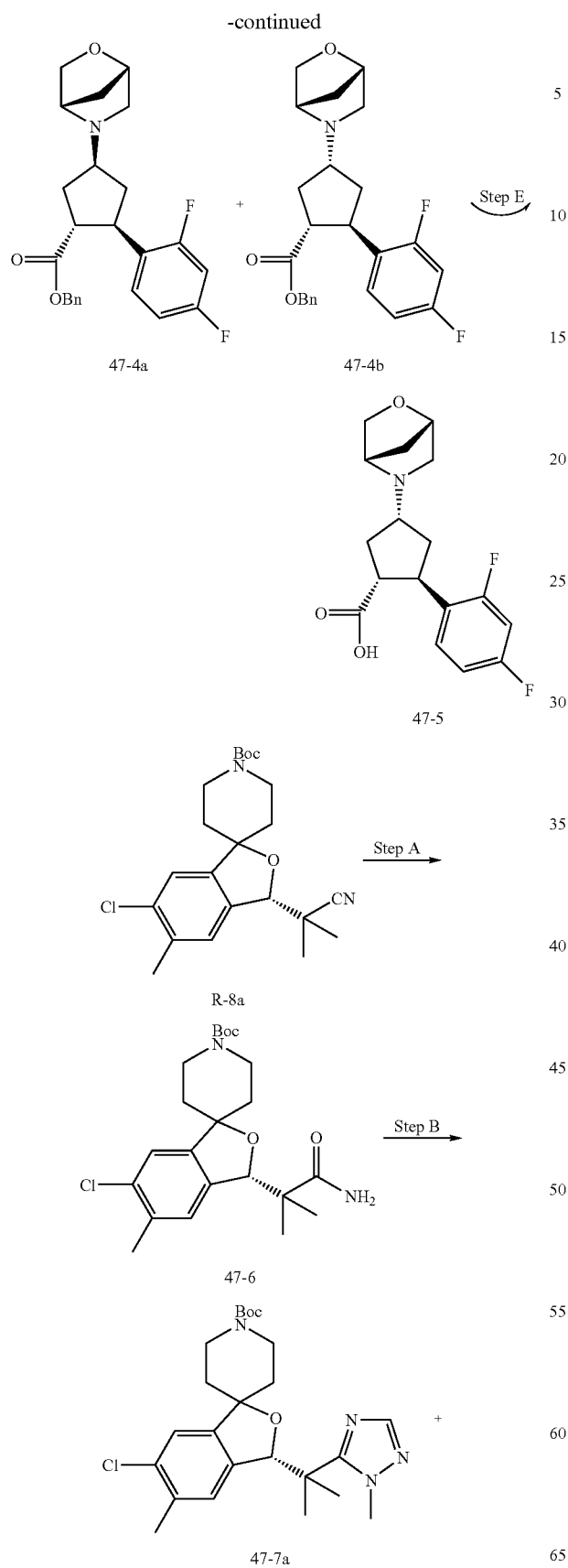

Step A: To the stirred solution of compound 1-5 (2.4 g) in DMF (10 mL) was added Et₃N (1.4 mL), NaHCO₃ (2.57 g) and benzyl bromide (1.8 mL). The mixture was stirred at room temperature overnight, followed by partitioning between EtOAc and 1N HCl solution. The layers were separated and the aqueous layer was extracted with EtOAc three times. The organic phases were combined, dried over anhydrous MgSO₄, and purified by a flash column chromatography on silica gel (gradient elution: 0-20% EtOAc/Hexane as eluent) to give 47-1. ESI-MS calc. for $C_{20}H_{18}F_2O_2$: 328; Found: 329 (M+H).

Step B: To the stirred solution of compound 47-1 (2.97 g) in THF (100 mL) and H₂O (20 mL) was added dropwise a solution of OsO₄ in t-BuOH (11.3 mL, 2.5 wt % in t-BuOH). The mixture was stirred for 20 minutes, then a solution of NaIO₄ (7.73 g) in H₂O (80 mL) was added. The mixture was stirred at room temperature overnight, then quenched with addition of a saturated Na₂S₂O₃ solution (100 mL). EtOAc was added to the mixture to extract the product out three times. The organic phases were combined, dried over anhydrous MgSO$_4$ and concentrated in vacuo to give 47-2 as pale yellow solid, which was used in the next step without further purification. ESI-MS calc. for C$_{19}$H$_{16}$F$_2$O$_3$: 330; Found: 331 (M+H).

Step C: To the stirred solution of 47-2 (1.0 g) in CH$_2$Cl$_2$ (10 mL) was added (1S,4S)-2-oxa-5-azabicyclo[2.2.1]heptane HCl salt (1.23 g), DIPEA (1.58 mL) and molecular sieves (2 g). After stirring for 30 minutes, Na(OAc)$_3$BH (1.92 g) was added. The reaction suspension was stirred at room temperature overnight. After filtration, the filtrate was washed with saturated NaHCO$_3$, brine and concentrated. The resulting residue was purified by a flash column chromatography on silica gel to give a racemic mixture of 47-3. ESI-MS calc. for C$_{24}$H$_{25}$F$_2$NO$_3$: 413; Found: 414 (M+H).

Step D: The racemic mixture of compound 47-3 was resolved on high performance chromatography with Chiral-Pak OD column (Chiral Pak OD 10×250 mm 5 u column, flow rate at 9 mL/min with 8% isopropanol in heptane, and UV detection at 220 nM) to afford two separate enantiomers 47-4a and 47-4b.

Step E: To a solution of compound 47-4a (450 mg) in EtOH (50 mL) was added Pd(OH)$_2$/C (400 mg). The mixture was stirred under a hydrogen atmosphere overnight. The solids were removed by filtration and the filtrate was concentrated in vacuo to give 47-5. ESI-MS calc. for C$_{17}$H$_{19}$F$_2$NO$_3$: 323; Found: 324 (M+H).

Step F: To a sealed tube was added compound R-8a (0.50 g), IPA (5.6 mL), H$_2$O (0.56 mL) and KOH (0.56 g). The reaction mixture was stirred at 85° C. overnight, then cooled to room temperature followed by addition of 1 mL of H$_2$O. The solids were filtered off, collected and washed with H$_2$O (1 mL) and IPA (1 mL), and then dried in vacuo to give compound 47-6. ESI-MS calc. for C$_{22}$H$_{31}$ClN$_2$O$_4$: 413; Found: 414 (M+H).

Step G: A solution of compound 47-6 (485 mg) in N,N-dimethyl formamide dimethyl acetal (40 mL) was stirred at 120° C. for 2 h in a sealed tube. Then the volatiles were removed by evaporation. The resulting crude product was dissolved in acetic acid (25 mL) and cooled to 0° C. before the addition of methyl hydrazine (0.22 mL). The reaction mixture was slowly warmed up to 90° C. and stirred at 90° C. for additional 2 h before cooling to room temperature. The solvent was removed in vacuo, and the crude material was purified by a flash column chromatography on silica gel (gradient elution: 0-50% EtOAc/Hexane as eluent) to give two separate regioisomers 47-7a and 47-7b as white solids. ESI-MS calc. for C$_{24}$H$_{33}$ClN$_4$O$_3$: 460; Found: 461 (M+H).

Step H: A solution of compound 47-7a (525 mg) in 4N HCl in dioxane (20 mL) was stirred at room temperature for 60 minutes and then evaporated to dryness to give 47-8 as white solid. ESI-MS calc. for C$_{19}$H$_{25}$ClN$_4$O: 360; Found: 361 (M+H).

Step I: To the stirred solution of 47-8 (127 mg) in dichloromethane was added DIPEA (0.22 mL), acid 47-5 (100 mg), HOAt (51 mg) and HATU (176 mg) in sequence. The mixture was stirred at room temperature overnight, and then purified by prep. TLC using 10% MeOH in dichloromethane as the eluting solvent to give 47-9 as white solid after acidification using 1N HCl in ether (~0.5 mL). ESI-MS calc. for C$_{36}$H$_{42}$ClF$_2$N$_5$O$_3$: 665; Found: 666 (M+H). $^1$H NMR (as HCl salt in CD$_3$OD, 500 mHz): δ 8.781-8.732 ppm (1H), δ 7.532-6.942 ppm (5H), δ 5.653 (1H), δ 2.403 (s, 3H), δ 4.718 4.440 ppm (3H), δ 4.269 (3H), δ 4.108-2.968 (8H), δ 2.833-2.705 (4H), δ 2.403 (s, 3H), δ 2.324-1.365 (11H).

EXAMPLE 48

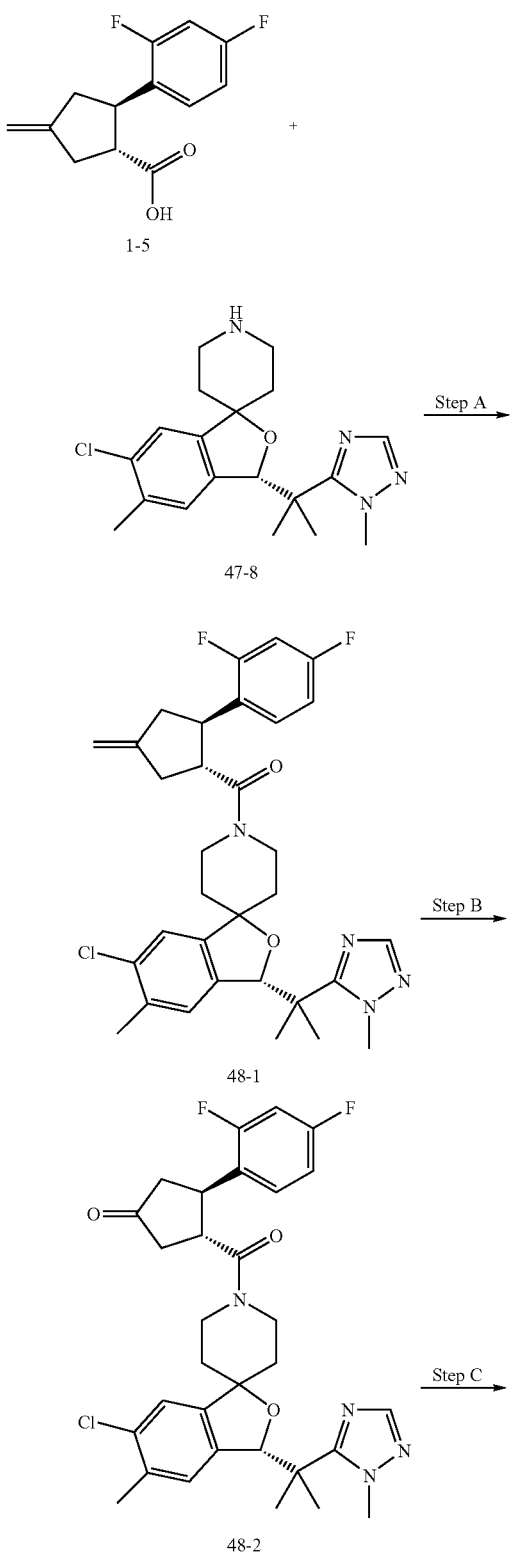

-continued

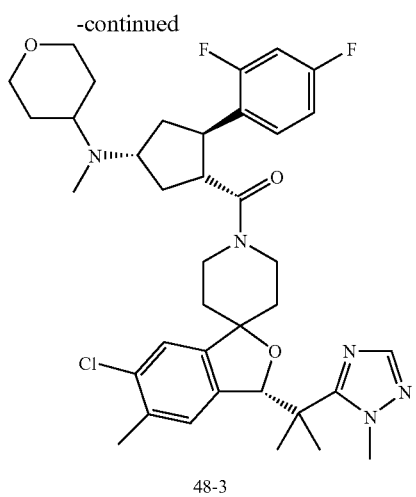

48-3

Step A: To a solution of compound 1-5 (30.3 mg) in dichloromethane (2 mL) was added DIPEA (0.074 mL), HOAt (17.3 mg, 0.127), HATU (80.6 g) and compound 47-8 (42 mg). The reaction mixture was stirred at room temperature overnight, diluted with dichloromethane, and washed with water and brine. The organic layer was dried over anhydrous magnesium sulfate, filtered, and concentrated to give compound 48-1. ESI-MS calc. for $C_{32}H_{35}ClF_2N_4O_2$: 580; Found: 581 (N+H).

Step B: To a solution of compound 48-1 (40 mg) in THF (2 mL) and water (0.5 mL) at room temperature was added $OsO_4$ (2.5 weight % solution in t-BuOH, 87 μl). After stirring the reaction mixture at r.t. for 10 minutes, sodium periodate (59 mg in 1.5 mL $H_2O$) was added slowly over 15 minutes, and the mixture was stirred for 4 hours. Then a saturated solution of sodium thiosulfate pentahydrate was added, and the reaction mixture was stirred for an additional 15 minutes. The layers were separated, and the aqueous layer was extracted with EtOAc, dried over $MgSO_4$, filtered and concentrated to give compound 48-2. ESI-MS calc. for $C_{31}H_{33}ClF_2N_4O_3$: 582; Found: 583 (M+H).

Step C: To a solution of N-methyltetrahydro-2H-pyran-4-ammonium chloride (37 mg) in dichloromethane (2 mL) was added DIPEA (43 μl), compound 48-2 (29 mg) and molecular sieves (200 mg). The reaction mixture was stirred at room temperature for 10 minutes, followed by the addition of sodium triacetoxyborohydride (52 mg). After stirring 18 hours, the reaction mixture was diluted with $CH_2Cl_2$, washed with saturated $NaHCO_3$ and brine, dried over anhydrous sodium sulfate, filtered and concentrated to give a residue. The residue was purified by prep TLC on silica gel (dichloromethane/methanol/15N $NH_4OH$ aqueous solution=90:9:1) to give compound 48-3. ESI-MS calc. for $C_{37}H_{46}ClF_2N_5O_3$: 681; Found: 682 (M+H).

The following compounds were prepared using the appropriate reagents following procedures similar to that described above for Example 1:

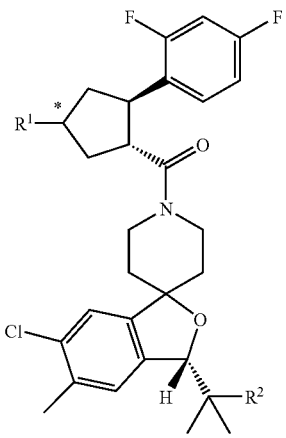

| Example | R¹ | R² | *D1 or D2 | Parent Ion m/z (M + H) |
|---|---|---|---|---|
| 49 | morpholino-N- | CN | D1 | 598 |
| 50 | morpholino-N- | CN | D2 | 598 |

-continued
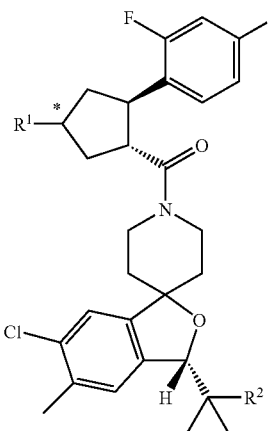
| Example | R¹ | R² | *D1 or D2 | Parent Ion m/z (M + H) |
|---|---|---|---|---|
| 51 | tetrahydropyran-4-yl-N(Me)- | CN | D1 | 626 |
| 52 | tetrahydropyran-4-yl-N(Me)- | CN | D2 | 626 |
| 53 | (3-methoxy)pyrrolidinyl- | CN | D1 | 612 |
| 54 | (3-methoxy)pyrrolidinyl- | CN | D1 | 612 |
| 55 | (3-fluoro)pyrrolidinyl- | CN | D1 | 600 |
| 56 | (3-fluoro)pyrrolidinyl- | CN | D2 | 600 |
| 57 | (3-fluoro)pyrrolidinyl- | CN | D1 | 600 |
| 58 | (3-fluoro)pyrrolidinyl- | CN | D2 | 600 |

-continued
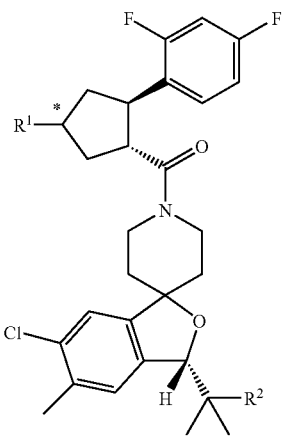
| Example | R¹ | R² | *D1 or D2 | Parent Ion m/z (M + H) |
|---|---|---|---|---|
| 59 | (oxabicyclic-N) | CN | D1 | 600 |
| 60 | (oxabicyclic-N) | CN | D2 | 610 |
| 61 | (oxabicyclic-N) | C(CH₃)₂C(O)-morpholine | D2 | 698 |
| 62 | (3-F-pyrrolidinyl) | C(CH₃)₂C(O)-morpholine | D2 | 688 |
| 63 | (oxabicyclic-N) | C(CH₃)₂C(O)NHCH₃ | D2 | 642 |
| 64 | (tetrahydropyran-4-yl)(N-CH₃) | C(CH₃)₂C(O)NHCH₃ | D2 | 658 |
| 65 | (3-F-pyrrolidinyl) | C(CH₃)₂C(O)-(3-hydroxypyrrolidinyl) | D2 | 688 |

-continued
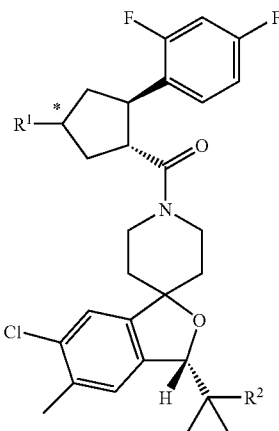
| Example | R¹ | R² | *D1 or D2 | Parent Ion m/z (M + H) |
|---|---|---|---|---|
| 66 | (S)-3-fluoropyrrolidin-1-yl | 1-methyl-1H-1,2,4-triazol-5-yl | D2 | 656 |
| 67 | 2-oxa-5-azabicyclo[2.2.1]heptan-5-yl | 1-methyl-1H-1,2,4-triazol-5-yl | D2 | 666 |
| 68 | 2-oxa-5-azabicyclo[2.2.1]heptan-5-yl | NHC(O)CH₃ | D2 | 642 |
| 69 | N-methyl-(tetrahydro-2H-pyran-4-yl)amino | NHC(O)CH₃ | D2 | 658 |
| 70 | N-methyl-(tetrahydro-2H-pyran-4-yl)amino | C(O)NHEt | D2 | 672 |
| 71 | N-ethyl-(tetrahydro-2H-pyran-4-yl)amino | C(O)NHEt | D2 | 686 |
| 72 | (tetrahydro-2H-pyran-4-yl)amino | C(O)NHEt | D2 | 658 |

-continued

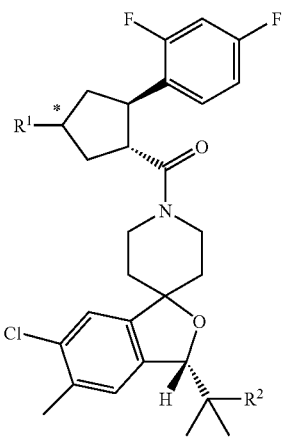

| Example | R¹ | R² | *D1 or D2 | Parent Ion m/z (M + H) |
|---|---|---|---|---|
| 73 | tetrahydropyran-4-yl-N(CH₃)- | -C(CH₃)₂C(O)NH₂ | D2 | 616 |
| 74 | tetrahydropyran-4-yl-N(CH₂CH₃)- | -C(CH₃)₂C(O)NH₂ | D2 | 630 |
| 75 | tetrahydropyran-4-yl-N(CH₂CH₃)- | -C(CH₃)₂C(O)NHCH₃ | D2 | 672 |
| 76 | tetrahydropyran-4-yl-N(CH₃)- | -C(CH₃)₂-(5-methyl-1,3,4-oxadiazol-2-yl) | D2 | 683 |
| 77 | 8-oxa-3-azabicyclo[3.2.1]oct-3-yl | -C(CH₃)₂-(1-methyl-1,2,4-triazol-3-yl) | D2 | 666 |

*D1 and D2 are diastereomers at the carbon of R¹ attachment. D1 is the diastereomer with the larger Rf value on a silica gel TLC plate (dichloromethane:methanol:15N NH₄OH aqueous solution = 90:9:1) and D2 is the diastereomer with the smaller Rf value.

EXAMPLE 78

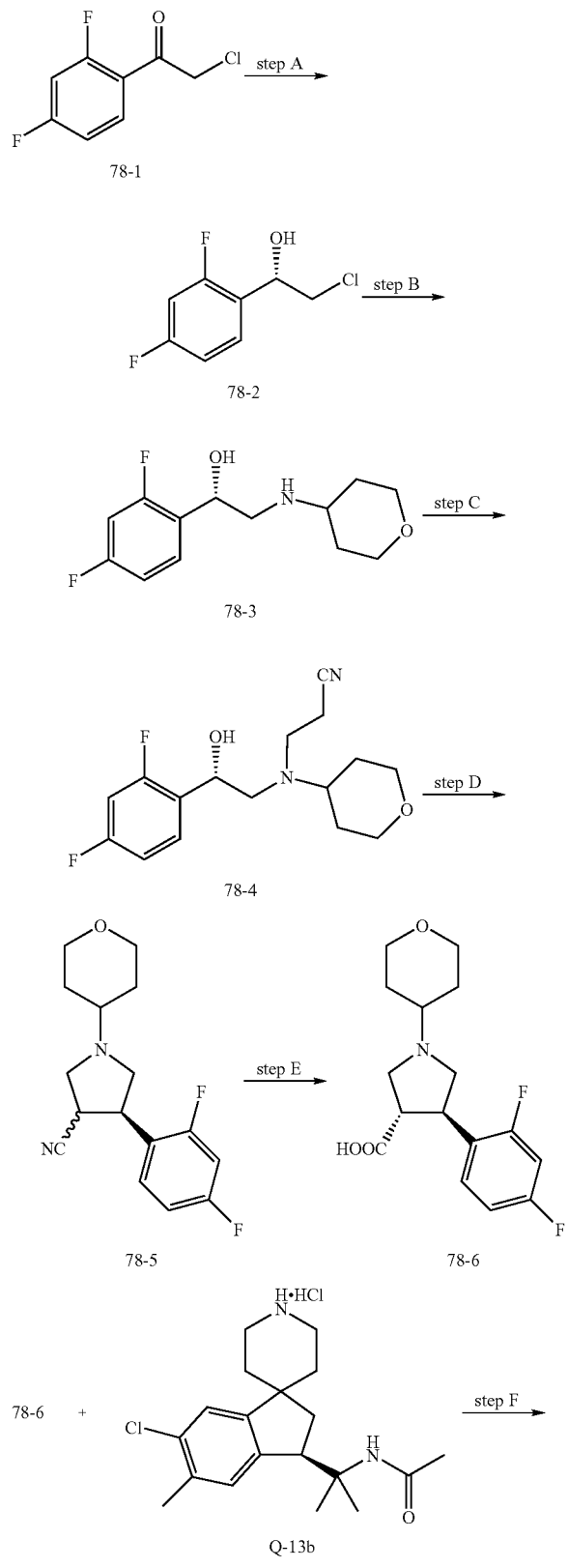

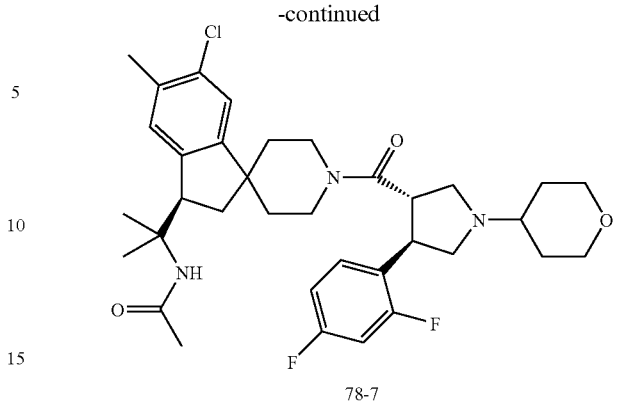

Step A: A solution of (S)-2-methyl-CBS-oxazaborolidine (0.26 mL, IM in toluene), borane-N,N-diethylaniline (9.3 mL) in MTBE (20 mL) was heated to 40° C., then a solution of 2-chloro-2',4'-di-fluoro-acetophenone 78-1 (10 g) in MTBE (32 mL) was added over one hour. The homogeneous solution was stirred at 40° C. for one hour, then allowed to cool to room temperature and stirred overnight. The reaction mixture was then cooled to 0° C. and methanol (4.6 mL) was added slowly. The resulting mixture was stirred at room temperature for 30 minutes, then 2 N aqueous HCl (52.4 mL) was added slowly at 0° C. After stirring 1 hour, the phases were separated; the organic phase was washed with saturated aqueous NaCl and concentrated to obtain compound 78-2.

Step B: A mixture of compound 78-2 (1.0 g) and 4-amino tetrahydropyran (1.58 g) was heated at 180° C. under nitrogen for 45 minutes, then cooled to room temperature and concentrated. The resulting residue was diluted with methylene chloride, and sodium hydroxide (1N, 2 mL) was added. The resulting layers were separated and the aqueous layer was extracted with methylene chloride. The combined organic layers were washed with brine, dried over sodium sulfate and concentrated. The resulting residue was purified by crystallization from heptane/ethyl acetate (3:1) to give compound 78-3. ESI-MS calc. for $C_{13}H_{17}F_2NO_2$: 257; Found: 258 (M+H).

Step C: A mixture of compound 78-3 (1.5 g) and acrylonitrile (9.6 mL) was heated at 80° C. under nitrogen. After heating 20 hours, ethanol (0.34 mL) and formamide (0.23 mL) were added and heating was continued for another 16 hours. The resulting reaction mixture was concentrated to give a residue; the residue was diluted with ethyl acetate, washed with brine, dried over sodium sulfate and concentrated. The resulting residue was purified by flash column chromatography on silica gel (12-50% ethyl acetate in hexane) to give colorless oil of compound 78-4. ESI-MS calc. for $C_{16}H_{20}F_2N_2O_2$: 310; Found: 311 (M+H).

Step D: To a solution of compound 78-4 (1.3 g) in dry THF (6.5 mL) at −20° C. was added diethyl chlorophosphate (0.64 mL). LiHMDS (1.0 M in THF solution; 8.8 mL) was slowly added over 40 minutes and stirred at −15° C. for 2 hrs. The reaction mixture was quenched with water (10.3 mL), extracted with n-heptane, washed with brine, dried over sodium sulfate and concentrated to give a colorless oil of compound 78-5. ESI-MS calc. for $C_{16}H_{18}F_2N_2O$: 292; Found: 293 (M+H).

Step E: To a solution of compound 78-5 (1.2 g) in ethanol (6 mL) was added 50% NaOH (0.65 mL). The solution was heated to reflux (90° C.) under nitrogen for 18 hours, then diluted with ethanol (4 mL) and methanol (10 mL), and cooled to 0° C. The pH of the solution was adjusted to pH 6-7 with $H_2SO_4$ and $Na_2SO_4$ was added. The mixture was stirred for 10 minutes, filtered, rinsed with methanol/ethanol (1:1), and the filtrate was concentrated to give solid 78-6. ESI-MS calc. for $C_{16}H_{19}F_2NO_3$: 311; Found: 312 (M+H).

Step F: To a suspension of acid 78-6 (41.6 mg) in dichloromethane (5 ml) was added NMM (0.067 ml), HOBt (32.9 mg), EDC (46.6 mg) and amine Q-13b (45 mg). After stirring at room temperature overnight, the reaction mixture was concentrated, and the resulting residue was purified by preparative TLC(CHCl$_3$: 2N NH$_3$ in CH$_3$OH=10:1) to give compound 78-7 as a yellow solid. ESI-MS calc. for $C_{35}H_{44}ClF_2N_3O_3$: 627; Found: 628 (M+H). $^1$H NMR (500 HMz, CD$_3$OD): 7.6-7.4 (m, 1H), 7.3-7.2 (m, 1H), 7.0-6.9 (m, 2H), 6.9 (s, 1H), 4.6-4.4 (m, 1H), 4.3-4.2 (m, 1H), 4.0-3.9 (m, 3H), 3.9-3.7 (m, 1H), 3.7-3.5 (m, 1H), 3.5-3.4 (m, 2H), 3.3-3.1 (m, 3H), 3.0-2.9 (m, 2H), 2.9-2.8 (m, 2H), 2.8-2.7 (m, 1H), 2.6-2.4 (m, 1H), 2.4-2.3 (m, 1H), 2.3 (s, 3H), 2.0 (s, 3H), 2.0-1.7 (m, 3H), 1.7-1.4 (m, 4H), 1.4 (s, 3H), 1.3-1.2 (m, 1H), 1.2-1.1 (s, 3H)

EXAMPLE 79

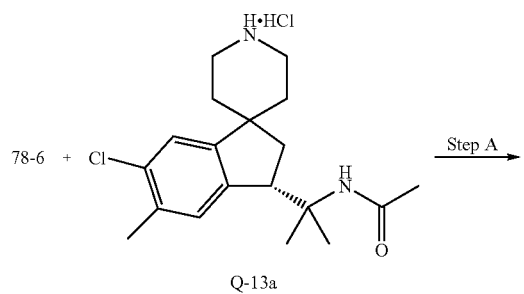

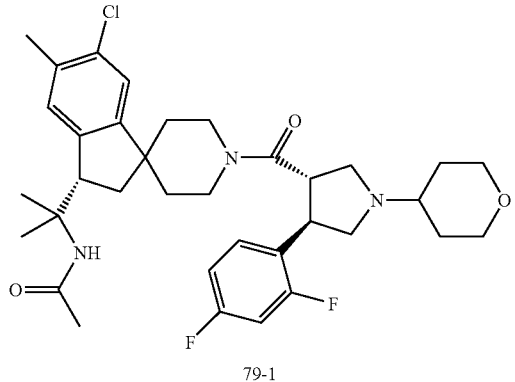

Step A: To a suspension of acid 78-6 (86.7 mg) in dichloromethane (10 mL) was added NMM (1.38 mL), HOBt (68.4 mg), EDC (97.0 mg) and amine Q-13a (100 mg). The reaction mixture was stirred at room temperature overnight, diluted with dichloromethane, washed with sodium bicarbonate (saturated) and brine, dried over anhydrous sodium sulfate, filtered, and concentrated. The resulting residue was purified by prep HPLC (20-80% Acetonitrile in water) to give white solid of compound 79-1. ESI-MS calc. for $C_{35}H_{44}ClF_2N_3O_3$: 627; Found: 628 (M+H). $^1$H NMR (500 HMz, CD$_3$OD): 7.6-7.4 (m, 1H), 7.3-7.2 (m, 1H), 7.1-6.91 (m, 2H), 6.90 (s, 1H), 4.6-4.4 (m, 1H), 4.3-4.2 (m, 1H), 4.0-3.9 (m, 3H), 3.9-3.75 (m, 1H), 3.7-3.5 (m, 1H), 3.45-3.4 (m, 2H), 3.2-3.1 (m, 4H), 3.0-2.8 (m, 4H), 2.5-2.4 (m, 2H), 2.4-2.3 (m, 1H), 2.3 (s, 3H), 2.0 (s, 3H), 1.9-1.8 (m, 2H), 1.6-1.4 (m, 4H), 1.4 (s, 3H), 1.3-1.2 (m, 1H), 1.2-1.1 (d, 3H).

The following compounds were prepared using the appropriate reagents following procedures similar to that described above for Example 78:

| Example | R | R$^1$ | Calculated MW | Parent Ion m/z (M + H) ESI-MS |
|---|---|---|---|---|
| 80 | 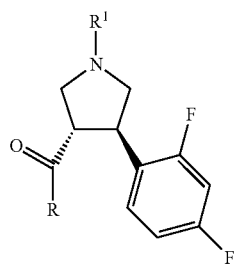 | tetrahydropyran-4-yl | $C_{33}H_{41}F_2N_3O_3$ 565 | 566 |

-continued
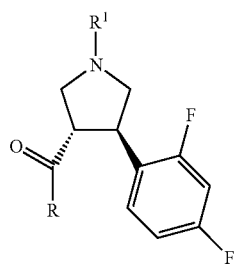
| Example | R | R¹ | Calculated MW | Parent Ion m/z (M + H) ESI-MS |
|---|---|---|---|---|
| 81 | (6-chloro-5-methyl-1-(2-(1-methyl-1H-1,2,4-triazol-5-yl)propan-2-yl)-2,3-dihydrospiro[indene-1,4'-piperidin]-1'-yl with N-methyl) | tetrahydropyran-4-yl | $C_{36}H_{44}ClF_2N_5O_2$ 651 | 652.42 |
| 82 | (6-fluoro-5-methyl-, d1 isomer) | tetrahydropyran-4-yl | $C_{36}H_{44}F_3N_5O_2$ 635 | 636.21 |
| 83 | (6-fluoro-5-methyl-, d2 isomer) | tetrahydropyran-4-yl | $C_{36}H_{44}F_3N_5O_2$ 635 | 636.23 |
| 84 | (6-chloro-5-methyl-, 5-methyl-1,3,4-oxadiazol-2-yl) | tetrahydropyran-4-yl | $C_{36}H_{43}ClF_2N_4O_3$ 652 | 653.37 |

-continued

| Example | R | R¹ | Calculated MW | Parent Ion m/z (M + H) ESI-MS |
|---|---|---|---|---|
| 85 | [6-chloro-1'-methyl-5-methylspiro[indane-1,4'-piperidin]-3-yl with C(CH₃)₂-1,3,4-oxadiazol-2-amine] | tetrahydropyran-4-yl | C₃₅H₄₂ClF₂N₅O₃ 653 | 654.46 |
| 86 | [6-chloro-1'-methyl-5-methylspiro[indane-1,4'-piperidin]-3-yl with C(CH₃)₂-1,3,4-oxadiazol-2(3H)-one] | tetrahydropyran-4-yl | C₃₅H₄₁ClF₂N₄O₄ 654 | 655.70 |
| 87 | [6-chloro-1'-methyl-5-methylspiro[indane-1,4'-piperidin]-3-yl with C(CH₃)₂-tetrazol-5-yl] | tetrahydropyran-4-yl | C₃₅H₄₂ClF₂N₅O₂ 637 | 638.63 |
| 88 | [6-chloro-1'-methyl-5-methylspiro[indane-1,4'-piperidin]-3-yl with C(CH₃)₂-1,2,3-triazol-4-yl] | tetrahydropyran-4-yl | C₃₅H₄₂ClF₂N₅O₂ 637 | 638.63 |

-continued

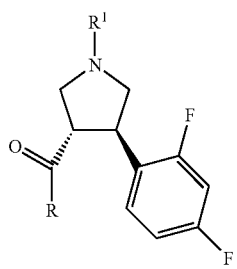

| Example | R | R¹ | Calculated MW | Parent Ion m/z (M + H) ESI-MS |
|---|---|---|---|---|
| 89 | 6-chloro-7-methyl-1'-methylspiro[indane-1,4'-piperidine] with 2-methyl-2-(N-methylcarbamoyl)ethyl | tetrahydropyran-4-yl | C₃₅H₄₄ClF₂N₃O₃ 627 | 628.22 |
| 90 | 6-chloro-7-methyl-1'-methylspiro[indane-1,4'-piperidine] with 2-(acetamido)propan-2-yl | tetrahydropyran-4-yl | C₃₆H₄₆ClF₂N₃O₃ 641 | 642 |
| 91 | 6-chloro-7-methyl-1'-methylspiro[indane-1,4'-piperidine] with 2-(acetamido)propan-2-yl | 3-methoxytetrahydropyran-4-yl | C₃₇H₄₈ClF₂N₃O₄ | 672 |
| 92 | 6-chloro-7-methyl-1'-methylspiro[indane-1,4'-piperidine] with 2-(acetamido)propan-2-yl | tetrahydropyran-4-yl | C₃₇H₄₆F₂N₄O₃ | 633 |

EXAMPLE 93

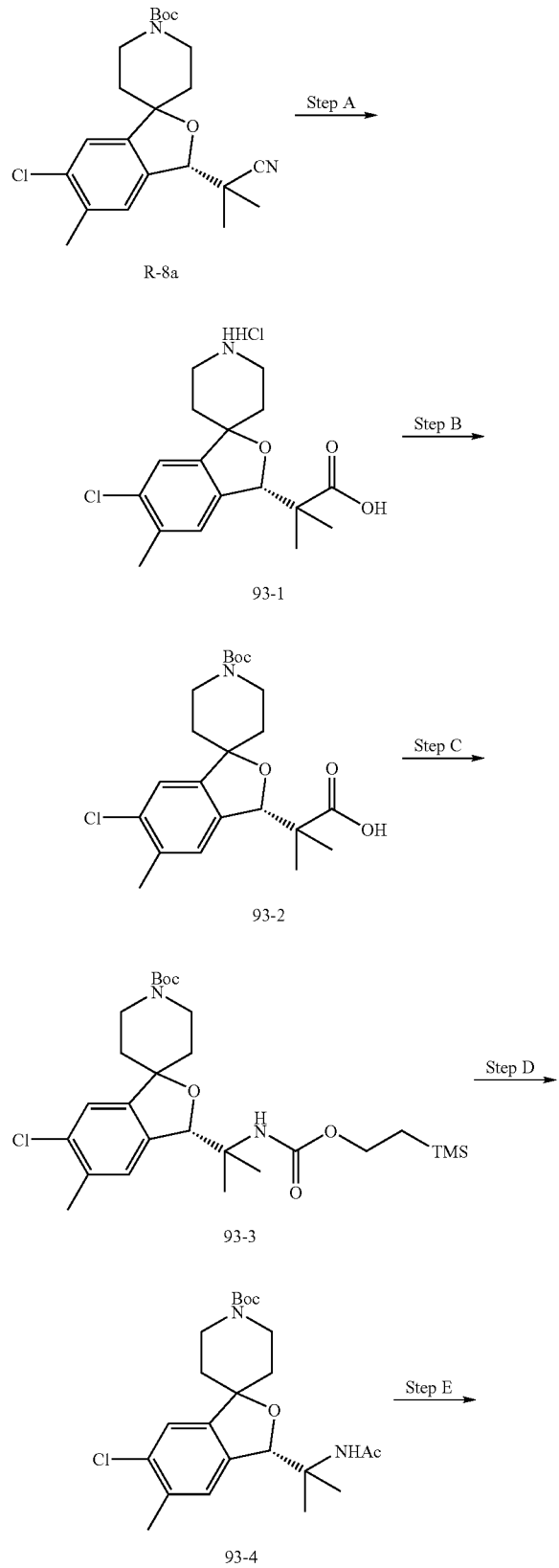

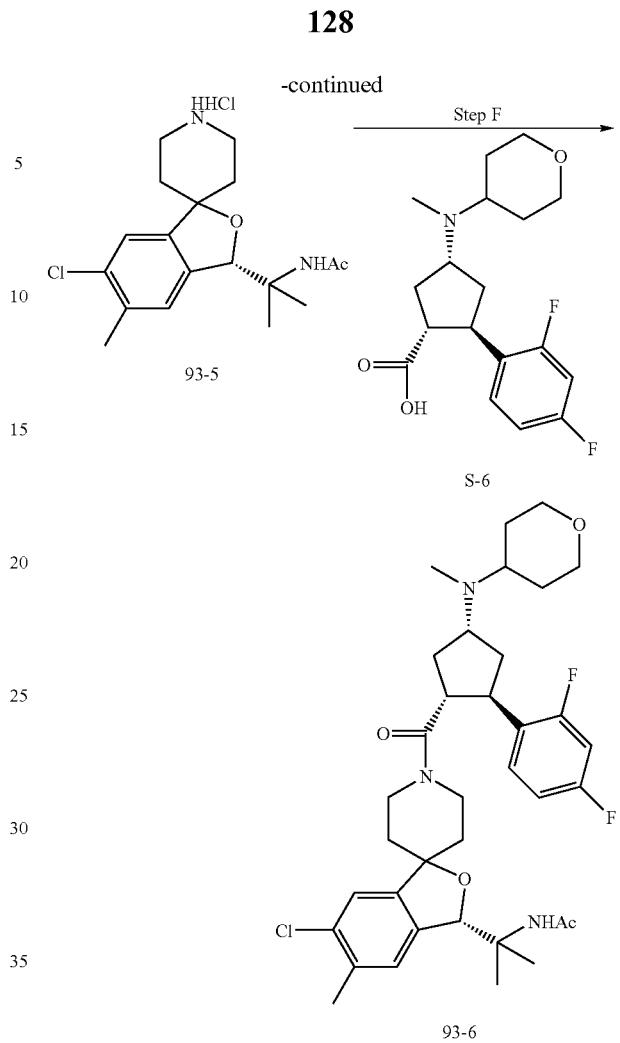

Step A: Compound R-8a (1 g) was dissolved in 4N HCl/dioxane (30 mL) and stirred at room temperature for 60 minutes, followed by evaporation to dryness. The resulting residue was dissolved in concentrated HCl (40 mL) and brought to reflux overnight. After cooling to RT, the mixture was concentrated under vacuum to give compound 93-1 as an off-white solid. ESI-MS calc. for $C_{17}H_{22}ClNO_3$: 323; Found: 324 (M+H).

Step B: To a stirred solution of compound 93-1 (1.0 g) in dioxane (30 mL) was added 1N NaOH solution (5.6 mL), $H_2O$ (10 mL), DIPEA (0.48 mL), and di-tert-butyl dicarbonate (909.9 mg). After stirring at room temperature for about 2 h, the mixture was partitioned between EtOAc and 1N HCl. The aqueous phase was extracted with EtOAc three times. The organic phases were combined and dried over $MgSO_4$, filtrated, and evaporated to give compound 93-2 as an off-white solid. ESI-MS calc. for $C_{22}H_{30}ClNO_5$: 423; Found: 424 (M+H).

Step C: To the stirred solution of compound 93-2 (1.64 g) in toluene (30 mL) was added $Et_3N$ (2.2 mL) and diphenylphosphorylazide (1.2 mL) at room temperature. The mixture was brought to reflux for 6 h followed by the addition of 2-(trimethylsilyl)ethanol and continued refluxing overnight. The mixture was cooled down to room temperature and the volatiles were evaporated to give crude material. The crude material was purified by a flash column chromatography on silica gel (gradient elution; 0%-12% ethyl acetate/hexanes as eluent) to yield compound 93-3 as a white solid. ESI-MS calc. for $C_{27}H_{43}ClN_2O_5Si$: 538; Found: 561 (M+Na).

Step D: To a 1 M solution of tetrabutylammonium fluoride in THF (50 mL) was added compound 93-3 (2.08 g) and the mixture was stirred at 50° C. for 2 h. After cooling down to room temperature, the mixture was partitioned between EtOAc and saturated NaHCO$_3$. The phases were separated and the aqueous phase was extracted with EtOAc three times. The organic phases were combined, dried over Na$_2$SO$_4$ and concentrated in vacuo to give a residue. The residue was dissolved in dichloromethane (30 mL) followed by addition of pyridine (3.6 mL) and acetic anhydride (3.6 mL). After stirring at room temperature overnight, the mixture was the diluted with dichloromethane, washed with 1N HCl solution, dried, and concentrated to give crude material. The crude material was purified by a flash column chromatography on silica gel (gradient elution; 0%-50% ethyl acetate/hexanes as eluent) to give compound 93-4 as white solid. ESI-MS calc. for C$_{23}$H$_{33}$ClN$_2$O$_4$: 436; Found: 437 (M+H).

Step E: A mixture of compound 93-4 (1.1 g) and 4N HCl solution (30 mL) was stirred at room temperature for 60 minutes followed by evaporation to dryness to give compound 93-5 as a white solid. ESI-MS calc. for C$_{18}$H$_{25}$ClN$_2$O$_2$: 336; Found: 337 (M+H).

Step F: To the stirred solution of compound 93-5 (648 mg) in dichloromethane (10 mL) was added acid S-6 (590 mg), DIPEA (1.2 mL), HOAt (355 mg) and HATU (1.322 g). The mixture was stirred at room temperature for 4 h, and then diluted with dichloromethane and washed with a saturated NaHCO$_3$ solution. The organic phase was separated, dried over Na$_2$SO$_4$, filtered, and concentrated to give a crude material, which was purified by a flash column chromatography on silica gel (90:9:1 ratio of CH$_2$Cl2:MeOH:NH$_4$OH as eluent) to yield compound 93-6. ESI-MS calc. for C$_{36}$H$_{46}$ClF$_2$N$_3$O$_4$: 657; Found: 658 (N+H). $^1$H NMR (as HCl salt in CD$_3$OD, 500 mHz): δ 7.846-6.780 ppm (m, 5H), δ 5.765-5.742 ppm (m, 1H), δ 4.846-1.007 ppm (m, 40H).

The following compounds were prepared using the appropriate starting materials following procedures similar to that described above for Examples 48, 78 and 93:

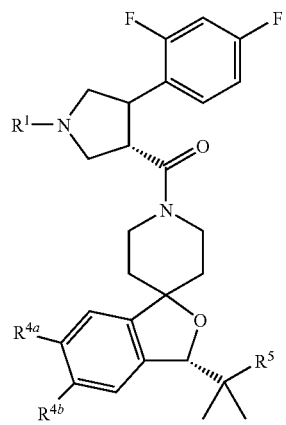

| Example | R$^1$ | R$^{4a}$ | R$^{4b}$ | R$^5$ | Parent Ion m/z (M + H) |
|---|---|---|---|---|---|
| 94 | tetrahydropyranyl | Cl | Me | CN | 598 |
| 95 | tetrahydropyranyl | Cl | Me | NHAc | 630 |
| 96 | tetrahydropyranyl | F | Cl | CN | 602 |
| 97 | tetrahydropyranyl | F | F | CN | 586 |
| 98 | tetrahydropyranyl | F | Me | CN | 582 |

-continued
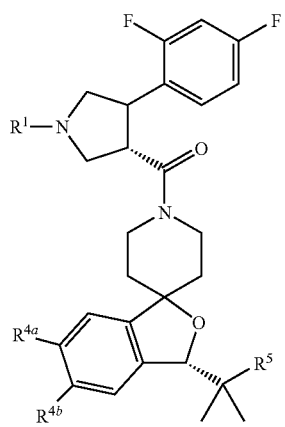
| Example | R¹ | R⁴ᵃ | R⁴ᵇ | R⁵ | Parent Ion m/z (M + H) |
|---|---|---|---|---|---|
| 99 | tetrahydropyran-4-yl | Cl | Me | 5-(1-methyl-1,2,4-triazolyl) | 654 |
| 100 | tetrahydropyran-4-yl | Cl | Me | CONH₂ | 616 |
| 101 | tetrahydropyran-4-yl | Cl | Me | 3-(1-methyl-1,2,4-triazolyl) | 654 |
| 102 | (tetrahydropyran-4-yl)methyl-gem-dimethyl | Cl | Me | CN | 612 |
EXAMPLE 103
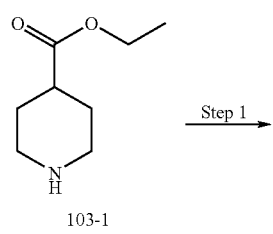
103-1
$\xrightarrow{\text{Step 1}}$
-continued
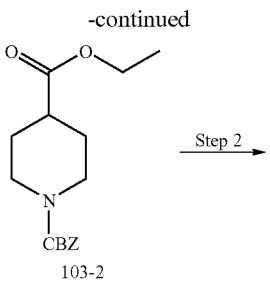
103-2
$\xrightarrow{\text{Step 2}}$

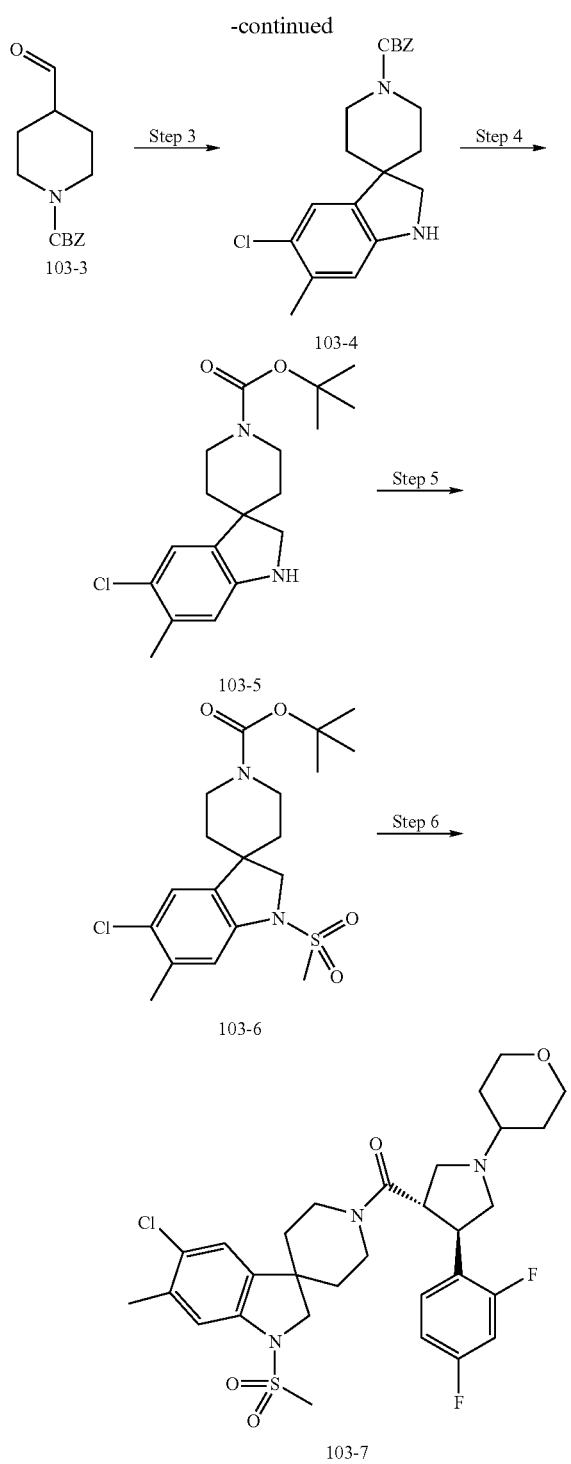

Step A: The commercially available piperidine ester 103-1 (6.2 mL) was dissolved in dichloromethane (60 mL) and water (60 mL) was added. The two phase mixture was stirred vigorously and benzyl chloroformate (6.32 mL) and NaHCO$_3$ (7.43 g) were added in portions over 10 minutes. Stirring was continued for 2 h and then the layers were separated. The organic layer was washed one time each with saturated aqueous NaHCO$_3$ and brine, dried over MgSO$_4$, filtered and evaporated. The resulting residue was dried under vacuum to give the protected amino ester 103-2 as a light orange oil, which was used without further purification. ESI-MS Calculated for C$_{16}$H$_{21}$NO$_4$: 291; Found: [M+H]$^+$=292.

Step B: The amino ester 103-2 (2.91 g) was dissolved in THF (30 mL) and lithium borohydride (0.690 g) was added. The suspension was heated to reflux and methanol (4.4 mL) was added in four equal portions over a period of 45 minutes. The mixture was refluxed for 1.5 h, then cooled to room temperature and quenched with 2N HCl (until acidic) and then basified with 5N NaOH. The aqueous layer was extracted with ethyl acetate (2×) and the combined organic portions were washed once with brine, dried over MgSO$_4$, filtered and evaporated. This resulting oily residue was dissolved in dichloromethane (10 mL) and added over 5 minutes to a solution of oxalyl chloride (5.75 mL) in dichloromethane (10 mL) at −70° C., which had been treated with dimethyl sulfoxide (1.63 mL). The reaction mixture was stirred at −70° C. for 30 min and then TEA (7.3 mL) was added and the suspension was allowed to warm to room temperature. The reaction mixture was diluted with dichloromethane and washed twice with water, dried over MgSO$_4$, filtered and evaporated. The residue was dissolved in ether, and washed with 2N HCl (2×) and brine (1×), dried again over MgSO$_4$, filtered and evaporated to give a crude product. The crude product was purified by flash chromatography on silica gel (hexane-ethyl acetate, 1:1) giving the aldehyde 103-3. ESI-MS Calculated for C$_{14}$H$_{17}$NO$_3$: 247; Found: [M+H]$^+$=248.

Step C: A solution of (4-chloro-3-methylphenyl)hydrazine (1.49 g), made from the HCl salt (toluene-H$_2$O-5N NaOH) and aldehyde 103-3 (2.36 g) in toluene (26.4 mL) and acetonitrile (0.6 mL), was stirred at room temperature for 5 minutes, and then cooled in an ice bath. Trifluoroacetic acid (2.21 mL) was added and the solution was allowed to warm to room temperature overnight. After 22 h at room temperature, the reaction mixture was heated to 35° C. and stirred overnight. The solution was cooled to 0° C. and methanol (2.22 mL) was added followed by the careful addition of NaBH$_4$ (0.542 g). The orange solution was warmed to room temperature after 15 minutes, and stirred for 1.5 h and then the solvents were removed by evaporation, replaced with ethyl acetate and washed with saturated aqueous NaHCO$_3$ (2×) and brine (1×). The organic layer was dried over MgSO$_4$, filtered and evaporated leaving a viscous yellow oil which was a mixture of regioisomers. Purification by flash chromatography on silica gel (hexane-ethyl acetate, 2:1) gave compound 103-4 as an inseparable mixture of regioisomers. ESI-MS Calculated for C$_{21}$H$_{23}$ClN$_2$O$_2$: 370; Found: [M+H]$^+$=371.

Step D: The mixture of the regioisomers of the spiroindole 103-4 (2.8 g) was dissolved in ethanol (28 mL) and 10% Pd/C (0.56 g) was added. Hydrogenolysis of the CBZ protecting group was carried out with H$_2$ at atmospheric pressure (balloon) for 5 h at which time fresh catalyst (10% Pd/C, 0.56 g) was added and the reaction continued for an additional 2.5 h. The reaction mixture was filtered through a bed of Celite® 545 and the filtrate was evaporated to dryness. Toluene was added to the residue and evaporated (2×) followed by drying under vacuum to give the deprotected amine (0.980 g). The crude intermediate was dissolved in dichloromethane (14 mL) and TEA (0.59 mL) and di-t-butyl dicarbonate (0.923 g) were added. The solution was stirred overnight, the solvent evaporated and replaced with ethyl acetate, washed one time with water, dried over MgSO$_4$, filtered and evaporated. Trituration of the residue in a small amount of ethyl acetate gave a precipitate which was primarily the undesired regioisomer while the desired product remained in the mother liquor. Purification by flash chromatography on silica gel(hexane-ethyl acetate, 3:1 followed by hexane-ethyl acetate, 1:1) gave 103-5, which contained 92% of the desired isomer by NMR. ESI-MS Calculated for $C_{18}H_2ClN_2O_2$: 336; Found: [M+H]$^+$=337.

Step E: The spiroindoline 103-5 (0.100 g) was dissolved in THF (5.0 mL) and cooled to −78° C. A solution of lithium diisopropylamide (2M in THF/n-heptane; 0.15 mL) was added from via syringe over approximately 1 minute. Stirring was continued for 15 minutes and then methanesulfonyl chloride (0.025 mL) was added over 1 minute. The reaction mixture was warmed to room temperature and stirred for an additional 40 minutes, then diluted with ethyl acetate, quenched with saturated aqueous NH$_4$Cl and washed one time each with water, saturated aqueous NaHCO$_3$ and brine, dried over MgSO$_4$, filtered and evaporated. The resulting crude product was purified by preparative TLC (silica gel, 20×20 cm plate, 1000μ thickness, hexane-ethyl acetate, 1:1) to give 103-6. ESI-MS Calculated for $C_{19}H_{27}ClN_2O_4S$: 414; Found: [M+Na]$^+$=437.

Step F: 4M HCl in dioxane (3 mL) was added to a solution of BOC protected indole 103-6 (95%, 0.039 g) in dichloromethane (2 mL) and stirred at room temperature for 1 h. The solvents were evaporated and the residue was dried briefly under vacuum and then dissolved in dichloromethane (3 mL) with N,N-diisopropylethylamine (0.039 mL). The resulting solution was added to a stirring solution of (3S,4R)-4-(2,4-difluorophenyl)-1-(tetrahydro-2H-pyran-4-yl)pyrrolidine-3-carboxylic acid (0.033 g), 1-hydroxy-benzotriazole hydrate (0.016 g) and EDC (0.026 g) in dichloromethane (3 mL). The reaction mixture was stirred overnight at room temperature, diluted with dichloromethane and washed one time each with water, saturated aqueous NaHCO$_3$ and brine, dried over MgSO$_4$, filtered and evaporated. The crude product was purified by preparative TLC (silica gel, 20×20 cm plate, 1000, thickness, hexane-ethyl acetate-MeOH, 12:8:2) to give 103-7. ESI-MS Calculated for $C_{30}H_{36}ClF_2N_3O_4S$: 607; Found: [M+H]$^+$=608. $^1$H NMR (500 MHz, CD$_3$OD, as HCl salt) aromatic H (δ 7.7-6.86 ppm, m and s, 5H), CH$_2$'s and CH's of piperidine, pyrrolidine and pyran (δ 4.6-1.5 ppm, complex mixture of multiplets, 23H), CH$_2$ of indoline (δ 3.9 ppm, split s, 2H), SO$_2$CH$_3$ (δ 2.99 ppm, s, 3H) and aromatic CH$_3$ (δ 2.34 ppm, s, 3H).

EXAMPLE 104

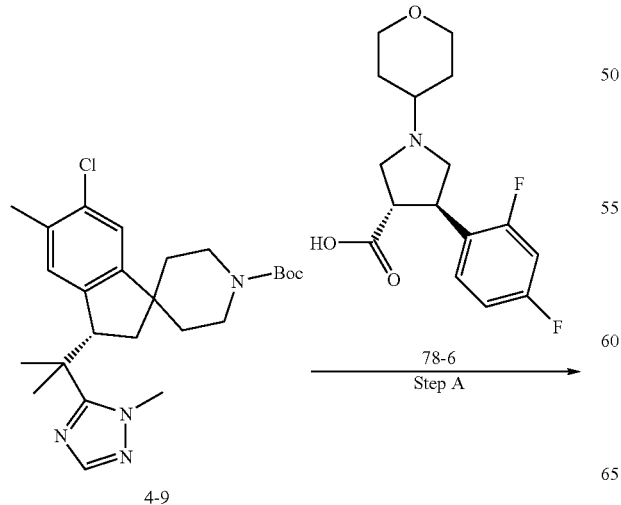

4-9

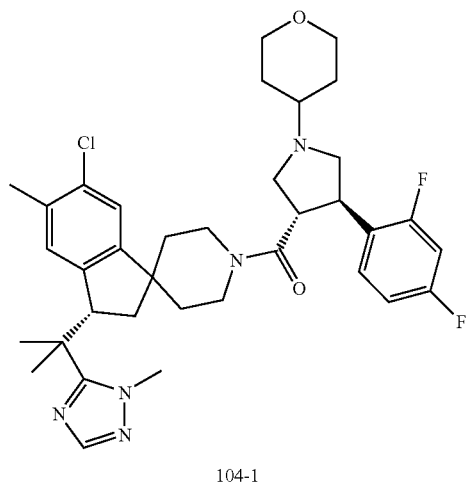

104-1

Step A: A solution of compound 4-9 (100 mg) in CH$_2$Cl$_2$ (2 mL) was treated with HCl (4 M in 1,4-dioxane, 6 mL) at room temperature. The resulting mixture was stirred at room temperature for 20 minutes, and then concentrated in vacuo to give a crude residue. A mixture of this residue, acid 78-6 (91.1 mg), HATU (99.6 mg), HOAT (35.8 mg) and 4-methylmorpholine (0.12 mL) in CH$_2$Cl$_2$ (7 mL) was stirred at room temperature overnight. The volatiles were removed to afford a residue, which was purified with HPLC on a C18 reversed phase column with a gradient 10% to 55% of water (0.1% TFA) and acetonitrile (0.1% TFA) and lypholized to afford compound 104-1. ESI-MS Calculated for $C_{36}H_{44}ClF_2N_5O_2$: 651; Found [M+H]$^+$=652.37.

EXAMPLE 105

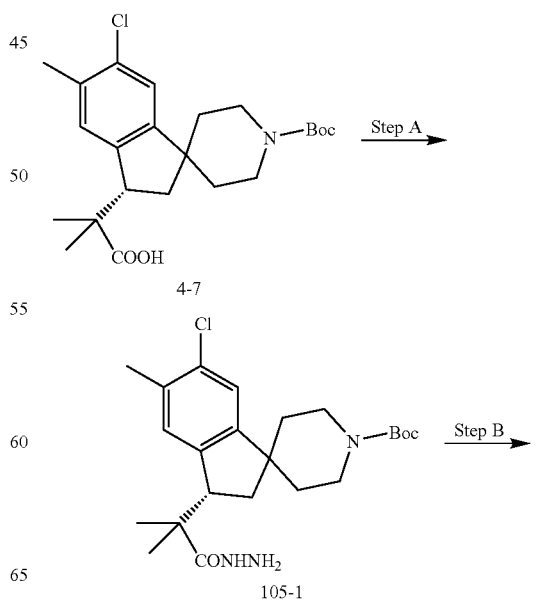

-continued

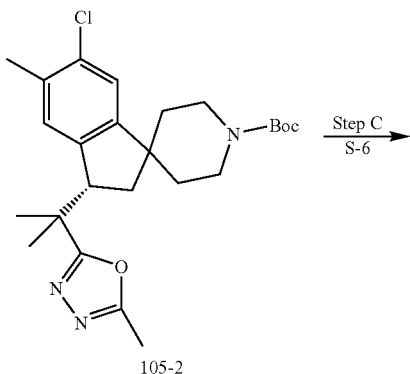

105-2

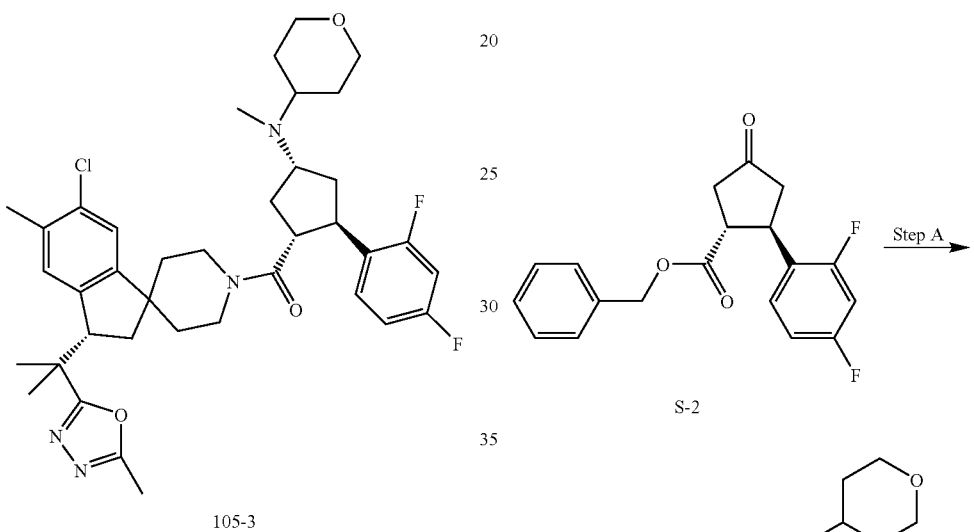

105-3

Step A: To a solution of compound 4-7 (50 mg) in DMF (2 mL) was added 1-hydroxy-7-azabenzotriazole (24.2 mg) and 1-(3-dimethylaminopropyl)-3-ethylcarbodiimide (34.2 mg) at room temperature. The reaction mixture was stirred for 6 hours. To the reaction mixture was added hydrazine monohydrate (0.03 mL). The resulting mixture was stirred at room temperature overnight. The reaction was diluted with water and extracted 3 times with EtOAc and hexanes. The combined organics were washed with water, 1N HCl, 1N NaOH, brine and dried ($Na_2SO_4$). Evaporation of the solvent afforded compound 105-1.

Step B: A suspension of compound 105-1 (52 mg) in triethyl orthoacetate (1.1 mL) was heated in an oil bath (150° C.) overnight. The reaction mixture was diluted with water and extracted 3 times with EtOAc and hexanes. The combined organics were washed with 1N HCl (aq.), 1N NaOH (aq.), brine and dried ($Na_2SO_4$). Evaporation of the solvent followed by silica gel prep TLC purification (30% acetone in hexanes) afforded compound 105-2.

Step C: A solution of compound 105-2 (41 mg) in $CH_2Cl_2$ (1 mL) was treated with HCl (4 M in 1,4-dioxane, 3 mL) at room temperature. The resulting mixture was stirred at room temperature for 20 minutes. The mixture was concentrated in vacuo to give a crude residue. A mixture of this residue, acid S-6 (59 mg), HATU (40.8 mg), HOAT (14.6 mg) and 4-methylmorpholine (0.05 mL) in $CH_2Cl_2$ (4 mL) was stirred at room temperature overnight. The volatiles were removed to afford a residue, which was purified with HPLC on a C18 reversed phase column with a gradient 10% to 65% of water (0.1% TFA) and acetonitrile (0.1% TFA) and lypholized to afford compound 105-3. $^1$H NMR (500 MHz, $CD_3OD$): δ 7.46 (m, 0.64H), 7.31 (m, 0.36H), 7.13 (s, 0.36H), 7.02 (m, 1.28H), 6.90 (t, 0.72H), 6.71 (s, 0.64H), 6.47 (s, 1H), 4.05 (t, 1H), 3.99 (m, 2H), 3.92 (d, 1H), 3.79 (m, 1.28H), 3.71 (m, 0.72H), 3.63 (m, 1.28H), 3.54 (m, 0.72H), 3.41 (t, 2H), 3.15 (t, 0.64H), 3.07 (t, 0.36H), 2.80 (m, 2H), 2.53 (m, 3H), 2.47 (m, 1H), 2.31 (s, 3H), 2.21 (s, 3H), 2.20 (m, 2H), 2.04 (m, 1H), 1.94 (m, 1H), 1.75 (m, 2H), 1.66 (m, 2H), 1.47 (m, 2H), 1.43 (s, 3H), 1.34 (s, 3H), 1.25 (m, 1H), 1.12 (m, 1H), 0.92 (m, 1H)

EXAMPLE 106

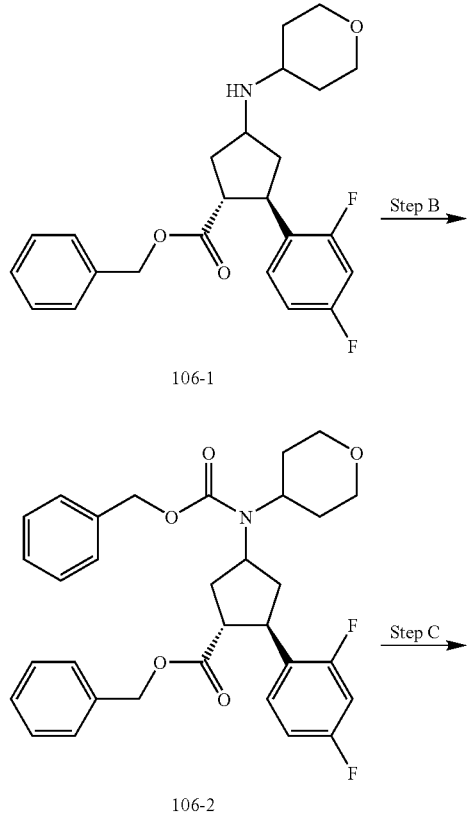

S-2

106-1

106-2

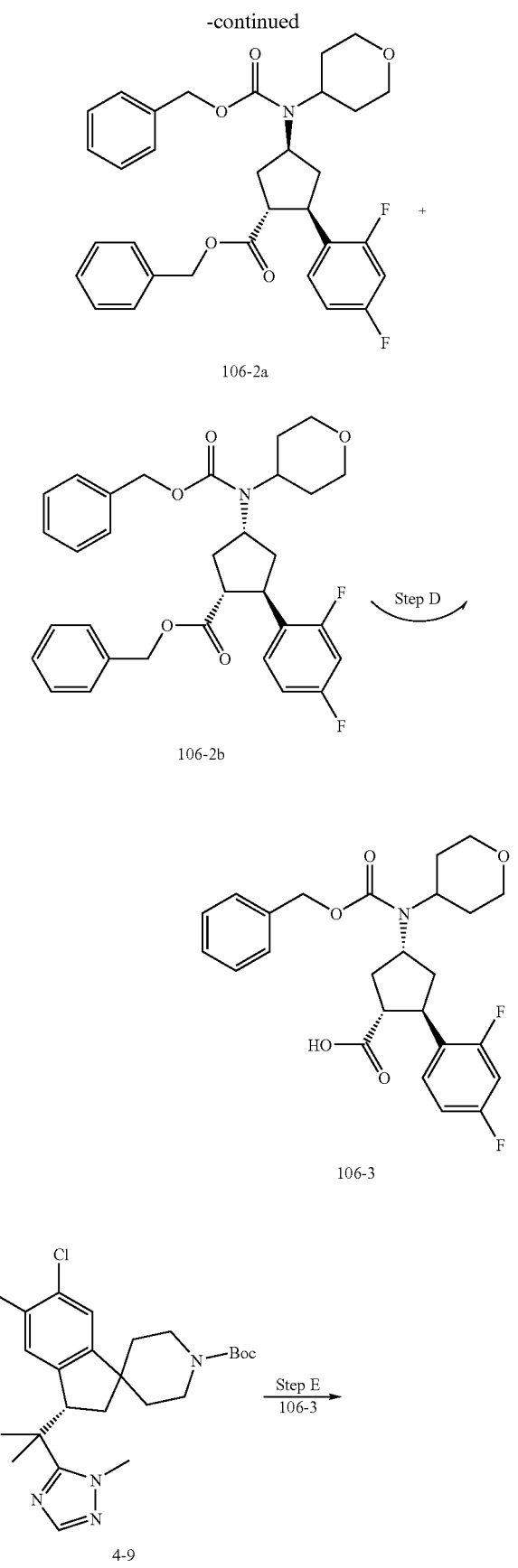
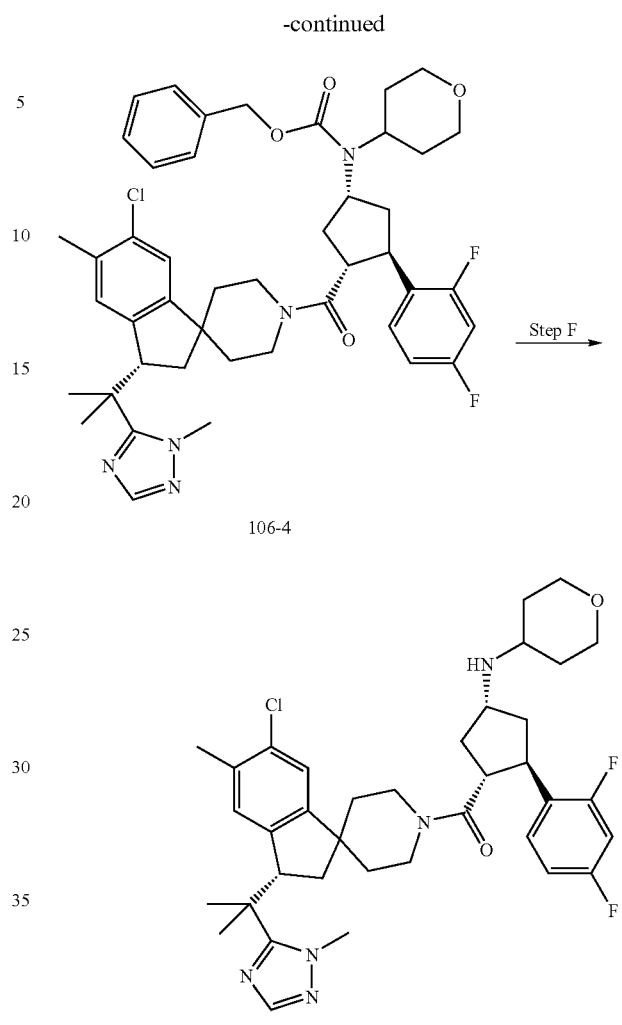

Step A: To a solution of compound S-2 (5.45 g) in CH₂Cl₂ (300 mL) was added 4-aminotetrahydropyran (5.0 g), Et₃N (46 mL), and molecular sieves (100 g, 4 A powder, <5 micron, activated) at room temperature. After stirring for 10 to 15 minutes, NaBH(OAc)₃ (21.0 g) was added. The reaction was stirred for four days at room temperature under N₂. The reaction was then quenched with the slow addition of ice, followed by 50 mL of 2N NaOH aqueous solution, and filtered through a pad of Celite®. The filtrate was extracted 2 times with CH₂Cl₂. The combined organics were dried (Na₂SO₄) and purified over silica gel (gradient elution: 0.5% to 10% CH₃OH in CH₂Cl₂) to afford compound 106-1.

Step B: To a solution of compound 106-1 (1.5 g) in CHCl₃ (18 mL) at room temperature was added benzyl chloroformate (0.62 mL) followed by 8% Na₂CO₃ (18 mL). The mixture was heated to 80° C. for seven hours under N₂. The reaction was cooled to room temperature and diluted with water. The reaction mixture was extracted 3 times with CH₂Cl₂. The combined organics were dried (Na₂SO₄) and purified over silica gel (gradient elution: 5% to 100% EtOAc in Hexanes) to afford compound 106-2 as an epimeric mixture of 106-3a and 106-3b.

141

Step C: Chiral HPLC resolution of 106-2 was carried out with ChiralPak OD column (3.5% ethanol in heptane). With a ChiralPak OD 4.6×250 mm column, flow rate at 0.5 ml/min of 7% ethanol in heptane, and UV detection at 220 nM, the retention times of the fast eluting compound 106-2a (e1) and the slow eluting compound 106-2b (e2) are 17.184 minutes and 19.192 minutes, respectively.

Step D: To a solution of compound 106-2b (50 mg) in THF:CH$_3$OH:H$_2$O (2.5:1:1, 2 mL) at room temperature was added LiOH: H$_2$O (15 mg). After 2 hours of stirring, the reaction was concentrated, acidified with 1 NHC1, and purified with HPLC on a C18 reversed phase column with a gradient of 10% to 100% acetonitrile (0.1% TFA) in water (0.1% TFA) and lypholized to afford compound 106-3.

Step E: A solution of compound 4-9 (25 mg) in CH$_2$Cl$_2$ (1 mL) was treated with HCl (4 M in 1,4-dioxane, 2 mL) at ambient temperature. The resulting mixture was stirred at ambient temperature for 20 minutes. The mixture was concentrated in vacuo to give a crude residue. A mixture of this residue, compound 106-3 (30 mg), HATU (25 mg), HOAT (8.9 mg) and 4-methylmorpholine (0.03 mL) in CH$_2$Cl$_2$ (3 mL) was stirred at ambient temperature overnight. The reaction was diluted with water and extracted 3 times with CH$_2$Cl$_2$ The combined organic layers were washed with 1N HCl, 1N NaOH, and brine. The organics were dried (Na$_2$SO$_4$) and concentrated to afford crude material which was and purified with HPLC on a C18 reversed phase column with a gradient of 10% to 100% acetonitrile (0.1% TFA) in water (0.1% TFA) and lypholized to afford compound 106-4.

Step F: Compound 106-4 (23 mg) was azeotroped twice with isopropyl alcohol before being re-dissolved in 2 ml of isopropyl alcohol. To this solution was added 1 N HCl (0.043 mL) and Pd/C (10%, 3 mg). The mixture was purged with N$_2$ followed by H$_2$. The reaction was stirred under an atmosphere of H$_2$ for four hours. The reaction was filtered, concentrated, and purified with HPLC on a C18 reversed phase column with a gradient of 10% to 100% acetonitrile (0.1% TFA) in water (0.1% TFA) and lypholized to afford compound 106-5. ESI-MS calculated for C$_{37}$H$_{46}$ClF$_2$N$_5$O$_2$: 665; Found [M+H]$^+$=666.79

EXAMPLE 107

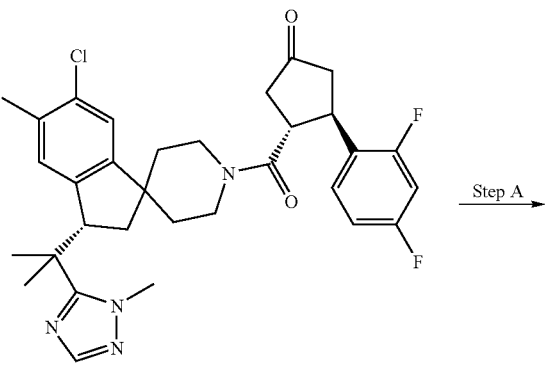

106-2

142

-continued

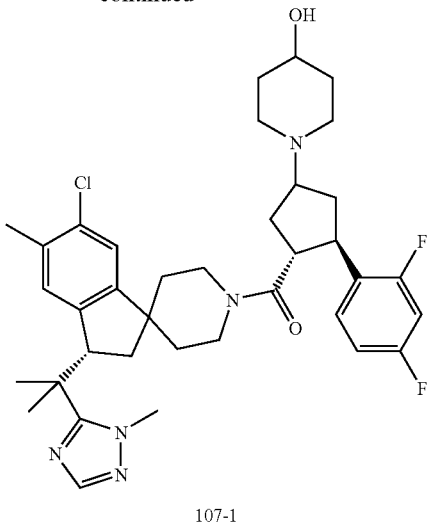

107-1

Step A: To 1.5 mL (0.056 mmol) of a stock solution of crude compound 106-2 (0.50 mmol in 13.5 mL of CH$_2$Cl$_2$) was added Et$_3$N (0.16 mL), 4-hydroxypiperidine (61.4 mg), and activated molecular sieves (4A, powder, <5 micron, 100 mg) at room temperature. The resulting mixture was stirred at room temperature for 90 minutes. To this mixture was added NaBH(OAc)$_3$ (118 mg). The reaction was stirred overnight at room temperature. The mixture was diluted with CH$_2$Cl$_2$ and H$_2$O, filtered, and concentrated to afford a residue, which was purified with HPLC on a C18 reversed phase column with a gradient of water (0.1% TFA) and acetonitrile (0.1% TFA) and lypholized to afford compound 107-1. ESI-MS Calculated for C$_{37}$H$_{46}$ClF$_2$N$_5$O$_2$: 665; Found [M+H]$^+$=666.24.

BIOLOGICAL ASSAYS

A. Binding Assay

The membrane binding assay was used to identify competitive inhibitors of $^{125}$I-NDP-alpha-MSH binding to cloned human MCRs expressed in mouse L- or Chinese hamster ovary (CHO)-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BR1); 100 mL 10% heat-inactivated fetal bovine serum (Sigma); 10 mL 10,000 unit/mL penicillin & 10,000 µg/nL streptomycin (Gibco/BR1); 10 mL 200 mM L-glutamine (Gibco/BR1); 1 mg/mL geneticin (G418) (Gibco/BR1). The cells were grown at 37° C. with CO$_2$ and humidity control until the desired cell density and cell number was obtained.

The medium was poured off and 10 mL/monolayer of enzyme-free dissociation media (Specialty Media Inc.) was added. The cells were incubated at 37° C. for 10 min or until cells sloughed off when flask was banged against hand.

The cells were harvested into 200 mL centrifuge tubes and spun at 1000 rpm, 4° C., for 10 min. The supernatant was discarded and the cells were resuspended in 5 mL/monolayer membrane preparation buffer having the composition: 10 mM Tris pH 7.2-7.4; 4 µg/mL Leupeptin (Sigma); 10 µM Phosphoramidon (Boehringer Mannheim); 40 µg/mL Bacitracin (Sigma); 5 μg/nL Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 min.

The pellets were resuspended in 0.2 mL/monolayer membrane prep buffer and aliquots were placed in tubes (500-1000 μL/tube) and quick frozen in liquid nitrogen and then stored at −80° C.

Test compounds or unlabelled NDP-α-MSH was added to 100 μL of membrane binding buffer to a final concentration of 1 μM. The membrane binding buffer had the composition: 50 mM Tris pH 7.2; 2 mM $CaCl_2$; 1 mM $MgCl_2$; 5 mM KCl; 0.2% BSA; 4 μg/mL Leupeptin (SIGMA); 10 μM Phosphoramidon (Boehringer Mannheim); 40 μg/mL Bacitracin (SIGMA); 5 μg/mL Aprotinin (SIGMA); and 10 mM Pefabloc (Boehringer Mannheim). One hundred μL of membrane binding buffer containing 10-40 μg membrane protein was added, followed by 100 μM 125I-NDP-α-MSH to final concentration of 100 μM. The resulting mixture was vortexed briefly and incubated for 90-120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 mL per well) with room temperature of filter wash having the composition: 50 mM Tris-HCl pH 7.2 and 20 mM NaCl. The filter was dried, and the bottom sealed and 50 μL of Packard Microscint-20 was added to each well. The top was sealed and the radioactivity quantitated in a Packard Topcount Microplate Scintillation counter.

B. Functional Assay

Functional cell based assays were developed to determine the efficacy of agonists and to discriminate melanocortin receptor agonists from antagonists.

Cells (for example, CHO— or L-cells or other eukaryotic cells) expressing a human melanocortin receptor (see e.g. Yang-Y K; Ollmann-M M; Wilson-B D; Dickinson-C; Yamada-T; Barsh-G S; Gantz-1;

Mol-Endocrinol. 1997 March; 11(3): 274-80) were dissociated from tissue culture flasks by rinsing with Ca and Mg free phosphate buffered saline (14190-136, Life Technologies, Gaithersburg, Md.) and detached following 5 min incubation at 37° C. with enzyme free dissociation buffer (S-014-B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/mL bovine serum albumin. Cells were counted and diluted to 1 to $5 \times 10^6$/mL. The phosphodiesterase inhibitor 3-isobutyl-1-methylxanthine was added to cells to 0.6 mM.

1. Agonist Assay Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min, cells were lysed by incubation at 100° C. for 5 min to release accumulated cAMP. cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a full agonist with an efficacy of 100%. The $EC_{50}$ is defined as the compound concentration which results in half maximal stimulation, when compared to its own maximal level of stimulation. Compounds that produce near 0% response are expected to be antagonist which will be further confirmed in the antagonist mode of the functional assay.

2. Antagonist Assay: Antagonist activity was defined as the ability of a compound to block cAMP production in response to alpha-MSH or any agonist. A solution of the test compound and suspension of receptor containing cells were prepared and mixed as described above; the mixture was incubated for 15 min, and an $EC_{50}$ dose of alpha-MSH (approximately 10 nM alpha-MSH) was added to the cells. The assay was terminated at 45 minutes and cAMP quantitated as above. Percent inhibition was determined by comparing the amount of cAMP produced in the presence to that produced in the absence of test compound. Antagonist is defined as a compound that by itself does not produce agonist-like response, and in combination with an agonist the compound should inhibit the agonist-induced response.

C. In Vivo Food Intake and Body Weight Models

1) Food intake and body weight in rats. Sprague Dawley rats are administered test compound one hour prior to onset of dark cycle (12 hours). Food intake is determined either by measurement of the remaining amount of preweighed food the morning following the dosing or by using a computerized system in which each rat's food is placed on a computer monitored balance. Cumulative food intake for 16 h post compound administration is measured. In some cases, food intake measurements are followed as long as 2 weeks. Body weight is measured daily; in some cases, adiposity is measured by DEXAscan analysis, tissue weights and plasma drug levels are measured. Animals can be dosed by a number of routes of administration. The routes of administration include intravenous, intraperitoneal, subcutaneous and intracerebral ventricular.

Compounds useful in the present invention decrease food intake acutely by at least 20% and/or decrease body weight in a 2 week period by at least 4% relative to placebo.

2) Food intake in diet induced obese mice. Male C57/B16J mice maintained on a high fat diet (30-60% fat calories) are dosed with test compound for 1 to 30 days. Food intake and body weight are measured overnight and sometimes daily as long as 30 days. Biochemical parameters relating to obesity, including leptin, insulin, triglyceride, free fatty acid, cholesterol and serum glucose levels and pharmacokinetic parameters may be determined. Animals can be dosed by a number of routes of administration. The routes of administration include intravenous, intraperitoneal, subcutaneous and intracerebral ventricular. Biochemical parameters relating to obesity, including leptin, insulin, triglyceride, free fatty acid, cholesterol and serum glucose levels are determined.

Compounds useful in the present invention decrease body weight by at least 4% relative to placebo.

D. Male Sexual Dysfunction

Mouse Electrically Stimulated Cavernosal Nerve (ESCN) Assay

Male C57BL6 mice are anesthetized, the carotid artery is exposed and cannulated for measurement of arterial pressure (MAP). A 30G needle attached to PE10 tubing, filled with heparinized saline, was inserted into the artery and glued in place. This tubing was connected to a pressure transducer and amplifier to measure direct MAP on a Gould 8 channel oscilloscope connected to a computer using the Po-ne-mah software to collect the data at one minute intervals. Another PE10 line attached to a 30G needle was inserted into the jugular vein for compound or vehicle administration. The cavernous nerve and penile body were exposed through a midline incision. Surrounding muscles were cauterized and removed for visualization of the cavernous nerve, which arises from the ipsilateral pelvic ganglion and is situated dorsal to the prostate. Another 30G needle attached to PEI 0 tubing, filled with heparinized saline, was inserted into the base of the corpus cavernosum near the crura and connected to the Gould system. A slight increase in intercavernous pressure (ICP) of approximately 5 to 10 mmHg is observed once this cannula is inserted into the corpus cavernosum. Heparinized saline (200 units/nL) was flushed through the cannula to assure proper placement of the cannula, inducing tumescence. The cavernous nerve was then isolated using curved #5 Dumont forceps and placed on a modified fixed position bipolar silver electrode (Harvard Apparatus). The electrodes are encased in plastic to allow stimulation of the nerve without additional stimulation of surrounding tissues. The electrode was advanced and held by a micromanipulator and was attached to a square wave stimulator to deliver electrical impulses at stimulation parameters ranging between 0.5 to 6.0v, 2 to 16 Hz, 1 ms, for 30 seconds. Electrical stimulations were administered to individual animals with 5 minute intervals between stimulations. Responses reported at each time point represent the mean of the two stimulations. ICP, MAP and ICP/MAP responses were continuously recorded at one second intervals for the duration of the experiment.

Measurements of ICP, MAP and ICP/MAP ratio are analyzed and responses compared to nerve stimulation in the presence and absence of compound or vehicle. For each parameter monitored, responses evoked by duplicate electrical stimulations were averaged, and the mean values were used for comparison. Response segments of 10 s of baseline+30 s stimulation+150 s post-stimulation were used to evaluate changes in ICP in response to electrical stimulation of the cavernous nerve. To assess direct effects of compound administration on ICP, a 300 s pre-compound response segment was compared to a comparable segment immediately after compound administration.

Compounds useful in the present invention increase intracavernous pressure by at least 25% for a time period of at least 15 minutes relative to placebo.

E. Models of Female Sexual Dysfunction

Rodent assays relevant to female sexual receptivity include the behavioral model of lordosis and direct observations of copulatory activity. There is also an urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*, Am. J. Physiol. (Regulatory Integrative Comp. Physiol 30): R1276-R1285, 1991; McKenna K E et al, *Modulation By Peripheral Serotonin of The Threshold For Sexual Reflexes In Female Rats*, Pharm. Bioch. Behav., 40:151-156, 1991; and Takahashi L K et al, *Dual Estradiol Action In The Diencephalon And The Regulation Of Sociosexual Behavior In Female Golden Hamsters*, Brain Res., 359:194-207, 1985.

F. Model of Cachexia

Rodent assays relevant to cachexia include the tumor cachexia model, in which cells derived from a tumor were injected into mice. Over a period of 1-3 weeks, a tumor will form and grow in the implanted mice. Tumor-bearing mice will exhibit reduced food intake and reduced body weight. By treating the tumor-bearing mice with an effective MC4R antagonist, food intake will be increased and body weight will be increased. This animal model of cachexia is described in Cone, R. D. et al, *Role of the Central Melanocortin System in Cachexia*, Cancer Research 61, 1432-38, Feb. 15, 2001.

Representative compounds of the present invention were tested and found to bind to the melanocortin-4 receptor. These compounds were generally found to have $IC_{50}$ values less than 10 μM. Representative agonist compounds of the present invention were also tested in the functional assay and found generally to activate the melanocortin-4 receptor with EC50 values less than 5 μM.

Representative antagonist compounds of the present invention were tested in the functional assay and found generally not to activate the melanocortin-4 receptor with an efficacy <5%, and generally have an $IC_{50}$ from the antagonist assay of less than 10 uM.

Examples of Pharmaceutical Compositions

As a specific embodiment of an oral composition of a composition of the present invention, 5 mg of Example 1 is formulated with sufficient finely divided lactose to provide a total amount of 580 to 590 mg to fill a size 0 hard gelatin capsule.

As another specific embodiment of an oral composition of a compound of the present invention, 2.5 mg of Example 1 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula I

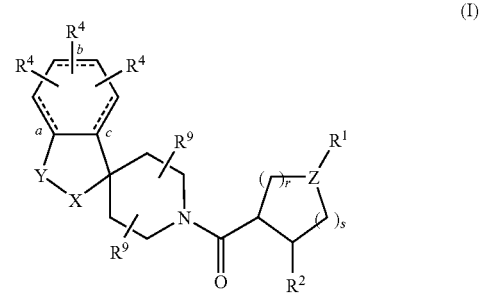

or a pharmaceutically acceptable salt thereof; wherein:
a, b and c are all single bonds or all double bonds;

Y is selected from the group consisting of:
(1) —C(R$^7$)(R$^6$),
(2) —N(R$^6$),
(3) C(O),
(4) oxygen,
(5) sulfur,
(6) S(O), and
(7) S(O)$_2$;

X is selected from the group consisting of:
(1) CH$_2$,
(2) —C(R$^7$)(R$^6$),
(3) C(O),
(4) oxygen,
(5) N(R$^6$),
(6) sulfur,
(7) S(O), and
(8) S(O)$_2$;

Z is selected from the group consisting of:
(1) CH, and
(2) N;

R$^1$ is selected from the group consisting of:
(1) —(CH$_2$)$_n$C$_{2-7}$heterocycloalkyl, and
(2) —N(R$^7$)C$_{2-7}$heterocycloalkyl,
wherein heterocycloalkyl, and (CH$_2$)$_n$ are unsubstituted or substituted with one to three groups independently selected from R$^3$ and oxo;

R$^2$ is selected from the group consisting of:
(1) phenyl,
(2) naphthyl, and
(3) heteroaryl,
wherein phenyl, naphthyl, and heteroaryl are unsubstituted or substituted with one to three groups independently selected from R$^8$;

R$^3$ and R$^4$ are independently selected from the group consisting of:
(1) hydrogen,
(2) C$_{1-8}$ alkyl,
(3) —(CH$_2$)$_n$-phenyl,
(4) —(CH$_2$)$_n$-naphthyl,
(5) —(CH$_2$)$_n$-heteroaryl,
(6) —(CH$_2$)$_n$C$_{2-7}$ heterocycloalkyl,
(7) —(CH$_2$)$_n$C$_{3-7}$ cycloalkyl,
(8) halogen,
(9) —OR$^5$,
(10) —(CH$_2$)$_n$N(R$^5$)$_2$,
(11) —(CH$_2$)$_n$C≡N,
(12) —(CH$_2$)$_n$C(O)OR$^5$,
(13) —(CH$_2$)$_n$OC(O)R$^5$,
(14) —NO$_2$,
(15) —(CH$_2$)$_n$NR$^5$S(O)$_p$R$^5$,
(16) —(CH$_2$)$_n$N(S(O)$_p$R$^5$)$_2$,
(17) —(CH$_2$)$_n$S(O)$_p$N(R$^5$)$_2$,
(18) —(CH$_2$)$_n$S(O)$_p$R$^5$,
(19) —(CH$_2$)$_n$NR$^5$C(O)N(R$^5$)$_2$,
(20) —(CH$_2$)$_n$C(O)N(R$^5$)$_2$,
(21) —(CH$_2$)$_n$NR$^5$C(O)R$^5$,
(22) —(CH$_2$)$_n$NR$^5$CO$_2$R$^5$,
(23) —(CH$_2$)$_n$NR$^5$C(O)-heteroaryl,
(24) —(CH$_2$)$_n$C(O)NR$^5$N(R$^5$)$_2$,
(25) —(CH$_2$)$_n$C(O)NR$^5$NR$^5$C(O)R$^5$,
(26) —O(CH$_2$)$_n$C(O)N(R$^5$)$_2$,
(27) —CF$_3$,
(28) —CH$_2$CF$_3$,
(29) —OCF$_3$, and
(30) —OCH$_2$CF$_3$,
wherein phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;

each R$^5$ is independently selected from the group consisting of:
(1) hydrogen,
(2) C$_{1-8}$ alkyl,
(3) —(CH$_2$)$_n$C$_{3-7}$ cycloalkyl,
(4) —(CH$_2$)$_n$C$_{2-7}$heterocycloalkyl,
(5) —(CH$_2$)$_n$phenyl,
(6) —(CH$_2$)$_n$naphthyl,
(7) —(CH$_2$)$_n$heteroaryl, and
(8) —(CH$_2$)$_n$C$_{3-7}$ bicycloalkyl,
wherein alkyl, phenyl, heteroaryl, heterocycloalkyl, naphthyl, cycloalkyl, bicycloalkyl and (CH$_2$) are unsubstituted or substituted with one to three groups independently selected from halogen, C$_{1-4}$ alkyl, hydroxy, and C$_{1-4}$ alkoxy, or wherein two R$^5$ groups together with the atom to which they are attached form a 4- to 8-membered mono- or bicyclic ring system optionally containing an additional heteroatom selected from O, S, and —NC$_{1-4}$ alkyl;

each R$^6$ is independently selected from the group consisting of:
(1) —(CH$_2$)$_n$C$_{2-7}$ heterocycloalkyl,
(2) C$_{1-6}$ alkyl,
(3) —(CH$_2$)$_n$C$_{3-7}$ cycloalkyl,
(4) —(CH$_2$)$_n$C$_{2-7}$ heterocycloalkyl,
(5) —(CH$_2$)$_n$-phenyl,
(6) —(CH$_2$)$_n$-heteroaryl,
(7) —(CH$_2$)$_n$C(O)R$^5$,
(8) —(CH$_2$)$_n$C(O)OR$^5$,
(9) —(CH$_2$)$_n$C(OH)R$^5$,
(10) —(CH$_2$)$_n$C(O)(CH$_2$)$_n$N(R$^5$)$_2$,
(11) —(CH$_2$)$_n$C(O)(CH$_2$)$_n$NR$^7$R$^8$,
(12) —(CH$_2$)$_n$—OR$^5$,
(13) —(CH$_2$)$_n$—OC(O)R$^5$,
(14) —(CH$_2$)$_n$—O—(CH$_2$)$_n$—N(R$^5$)$_2$,
(15) —(CH$_2$)$_n$CN,
(16) —(CH$_2$)$_n$N(R$^5$)$_2$,
(17) —(CH$_2$)$_n$N(R$^5$)C(O)R$^5$,
(18) —(CH$_2$)$_n$N(R$^5$)C(O)OR$^5$,
(19) —(CH$_2$)$_n$N(R$^5$)C(O)(CH$_2$)$_n$N(R$^5$)$_2$,
(20) —(CH$_2$)$_n$N(R$^5$)—S(O)—C$_{1-8}$ alkyl,
(21) —(CH$_2$)$_n$N(R$^5$)—S(O)$_2$—C$_{1-8}$ alkyl,
(22) —(CH$_2$)$_n$—S—R$^5$,
(23) —(CH$_2$)$_n$—S(O)—R$^5$, and
(24) —(CH$_2$)$_n$—S(O)$_2$—R$^5$,
wherein phenyl and heteroaryl are unsubstituted or substituted with one to three groups independently selected from R$^3$, and wherein alkyl, cycloalkyl and heterocycloalkyl are unsubstituted or substituted with one to three groups independently selected from R$^3$ and oxo, and wherein any methylene (CH$_2$) in R$^6$ is unsubstituted or substituted with one to two groups independently selected from halogen, hydroxy, and C$_{1-4}$ alkyl; or wherein two R$^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^7$ is independently selected from the group consisting of:
(1) hydrogen, and
(2) $C_{1-8}$ alkyl,
wherein alkyl is unsubstituted or substituted with one to three groups independently selected from halogen, $C_{1-4}$ alkyl, hydroxy, and $C_{1-4}$ alkoxy;

each $R^8$ is independently selected from the group consisting of:
(1) $C_{1-6}$ alkyl,
(2) —$(CH_2)_n$phenyl,
(3) —$(CH_2)_n$naphthyl,
(4) —$(CH_2)_n$heteroaryl,
(5) —$(CH_2)_n C_{2-7}$heterocycloalkyl,
(6) —$(CH_2)_n C_{3-7}$cycloalkyl,
(7) halogen,
(8) —$OR^5$,
(9) —$(CH_2)_n N(R^5)_2$,
(10) —$(CH_2)_n C \equiv N$,
(11) —$(CH_2)_n CO_2 R^5$,
(12) —$NO_2$,
(13) —$(CH_2)_n NR^5 S(O)_p R^5$,
(14) —$(CH_2)_n S(O)_p N(R^5)_2$,
(15) —$(CH_2)_n S(O)_p R^5$,
(16) —$(CH_2)_n NR^5 C(O)N(R^5)_2$,
(17) —$(CH_2)_n C(O)N(R^5)_2$,
(18) —$(CH_2)_n NR^5 C(O)R^5$,
(19) —$(CH_2)_n NR^5 CO_2 R^5$,
(20) —$(CH_2)_n NR^5 C(O)$-heteroaryl,
(21) —$(CH_2)_n C(O)NR^5 N(R^5)_2$,
(22) —$(CH_2)_n C(O)NR^5 NR^5 C(O)R^5$,
(23) —$O(CH_2)_n C(O)N(R^5)_2$,
(24) —$CF_3$,
(25) —$CH_2 CF_3$,
(26) —$OCF_3$, and
(27) —$OCH_2 CF_3$;
wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and $(CH_2)$ are unsubstituted or substituted with one to three substituents independently selected from halogen, hydroxy, oxo, $C_{1-4}$ alkyl, trifluoromethyl, and $C_{1-4}$ alkoxy;

each $R^9$ is independently selected from the group consisting of:
(1) hydrogen,
(2) —OH,
(3) $C_{1-8}$alkyl,
(4) —$OC_{1-8}$alkyl,
(5) halogen;
(6) —$NR^5$,
(7) —$SR^5$, and
(8) —$CF_3$,
wherein two $C_{1-8}$alkyl substituents along with the atoms to which they are attached can form a 4- to 8-membered ring;
r is 1 or 2;
s is 1 or 2;
n is 0, 1, 2, or 3; and
p is 0, 1, or 2.

2. The compound of claim 1 wherein a, b and c are double bonds,
and pharmaceutically acceptable salts thereof.

3. The compound of claim 2 wherein $R^9$ is hydrogen, and pharmaceutically acceptable salts thereof.

4. The compound of claim 3 wherein Y is selected from the group consisting of:
—$C(R^7)(R^6)$ and —$N(R^6)$, and pharmaceutically acceptable salts thereof.

5. The compound of claim 3 wherein X is selected from the group consisting of: $CH_2$, C(O), and oxygen, and pharmaceutically acceptable salts thereof.

6. The compound of claim 3 wherein $R^2$ is phenyl unsubstituted or substituted with one to three groups independently selected from $R^8$, and pharmaceutically acceptable salts thereof.

7. The compound of claim 2 wherein $R^4$ is selected from the group consisting of: hydrogen, $C_{1-8}$ alkyl, and halogen, and pharmaceutically acceptable salts thereof.

8. The compound of claim 2 wherein Z is CH.
9. The compound of claim 6 wherein Z is N.
10. The compound of claim 2 wherein r is 1 or 2, and s is 1.
11. The compound of claim 1 of structural formula IIa or IIb of the indicated trans relative stereochemical configuration:

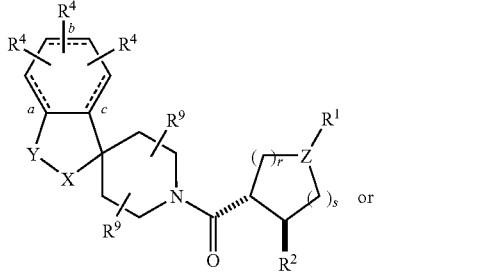

(IIa)

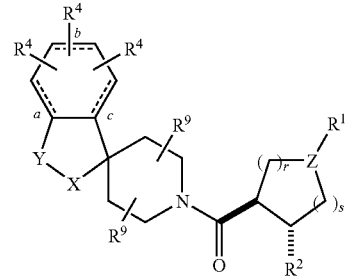

(IIb)

or a pharmaceutically acceptable salt thereof; wherein
a, b and c are all single bonds or all double bonds;
Y is selected from the group consisting of:
(1) —$C(R^7)(R^6)$,
(2) —$N(R^6)$,
(3) C(O),
(4) oxygen,
(5) sulfur,
(6) S(O), and
(7) $S(O)_2$;
X is selected from the group consisting of:
(1) $CH_2$,
(2) —$C(R^7)(R^6)$,
(3) C(O),
(4) oxygen,
(5) $N(R^6)$,
(6) sulfur,
(7) S(O), and
(8) $S(O)_2$;

Z is selected from the group consisting of:
(1) CH, and
(2) N;

$R^1$ is selected from the group consisting of:
(1) —$(CH_2)_n C_{2-7}$heterocycloalkyl, and
(2) —$N(R^7)C_{2-7}$heterocycloalkyl,
wherein heterocycloalkyl, and $(CH_2)_n$ are unsubstituted or substituted with one to three groups independently selected from $R^3$ and oxo;

$R^2$ is selected from the group consisting of:
(1) phenyl,
(2) naphthyl, and
(3) heteroaryl,
wherein phenyl, naphthyl, and heteroaryl are unsubstituted or substituted with one to three groups independently selected from $R^8$;

$R^3$ and $R^4$ are independently selected from the group consisting of:
(1) hydrogen,
(2) $C_{1-8}$alkyl,
(3) —$(CH_2)_n$phenyl,
(4) —$(CH_2)_n$naphthyl,
(5) —$(CH_2)_n$heteroaryl,
(6) —$(CH_2)_n C_{2-7}$heterocycloalkyl,
(7) —$(CH_2)_n C_{3-7}$cycloalkyl,
(8) halogen,
(9) —$OR^5$,
(10) —$(CH_2)_n N(R^5)_2$,
(11) —$(CH_2)_n C\equiv N$,
(12) —$(CH_2)_n C(O)OR^5$,
(13) —$(CH_2)_n OC(O)R^5$,
(14) —$NO_2$,
(15) —$(CH_2)_n NR^5 S(O)_p R^5$,
(16) —$(CH_2)_n N(S(O)_p R^5)_2$,
(17) —$(CH_2)_n S(O)_p N(R^5)_2$,
(18) —$(CH_2)_n S(O)_p R^5$,
(19) —$(CH_2)_n NR^5 C(O)N(R^5)_2$,
(20) —$(CH_2)_n C(O)N(R^5)_2$,
(21) —$(CH_2)_n NR^5 C(O)R^5$,
(22) —$(CH_2)_n NR^5 CO_2 R^5$,
(23) —$(CH_2)_n NR^5 C(O)$-heteroaryl,
(24) —$(CH_2)_n C(O)NR^5 N(R^5)_2$,
(25) —$(CH_2)_n C(O)NR^5 NR^5 C(O)R^5$,
(26) —$O(CH_2)_n C(O)N(R^5)_2$,
(27) —$CF_3$,
(28) —$CH_2 CF_3$,
(29) —$OCF_3$, and
(30) —$OCH_2 CF_3$,
wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and $(CH_2)$ are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene $(CH_2)$ group are taken together with the carbon atom to which they are attached to form a cyclopropyl group;

each $R^5$ is independently selected from the group consisting of:
(1) hydrogen,
(2) $C_{1-8}$alkyl,
(3) —$(CH_2)_n C_{3-7}$cycloalkyl,
(4) —$(CH_2)_n C_{2-7}$heterocycloalkyl,
(5) —$(CH_2)_n$phenyl,
(6) —$(CH_2)_n$naphthyl,
(7) —$(CH_2)_n$heteroaryl, and
(8) —$(CH_2)_n C_{3-7}$bicycloalkyl,
wherein alkyl, phenyl, heteroaryl, heterocycloalkyl, naphthyl, cycloalkyl, bicycloalkyl and $(CH_2)$ are unsubstituted or substituted with one to three groups independently selected from halogen, $C_{1-4}$ alkyl, hydroxy, and $C_{1-4}$ alkoxy, or wherein two $R^5$ groups together with the atom to which they are attached form a 4- to 8-membered mono- or bicyclic ring system optionally containing an additional heteroatom selected from O, S, and —$NC_{1-4}$ alkyl;

each $R^6$ is independently selected from the group consisting of:
(1) —$(CH_2)_n C_{2-7}$heterocycloalkyl,
(2) $C_{1-6}$alkyl,
(3) —$(CH_2)_n C_{3-7}$cycloalkyl,
(4) —$(CH_2)_n C_{2-7}$heterocycloalkyl,
(5) —$(CH_2)_n$phenyl,
(6) —$(CH_2)_n$heteroaryl,
(7) —$(CH_2)_n C(O)R^5$,
(8) —$(CH_2)_n C(O)OR^5$,
(9) —$(CH_2)_n C(OH)R^5$,
(10) —$(CH_2)_n C(O)(CH_2)_n N(R^5)_2$,
(11) —$(CH_2)_n C(O)(CH_2)_n NR^7 R^8$,
(12) —$(CH_2)_n$—$OR^5$,
(13) —$(CH_2)_n$—$OC(O)R^5$,
(14) —$(CH_2)_n$—$O$—$(CH_2)_n$—$N(R^5)_2$,
(15) —$(CH_2)_n CN$,
(16) —$(CH_2)_n N(R^5)_2$,
(17) —$(CH_2)_n N(R^5)C(O)R^5$,
(18) —$(CH_2)_n N(R^5)C(O)OR^5$,
(19) —$(CH_2)_n N(R^5)C(O)(CH_2)_n N(R^5)_2$,
(20) —$(CH_2)_n N(R^5)$—$S(O)$—$C_{1-8}$ alkyl,
(21) —$(CH_2)_n N(R^5)$—$S(O)_2$—$C_{1-8}$ alkyl,
(22) —$(CH_2)_n$—$S$—$R^5$,
(23) —$(CH_2)_n$—$S(O)$—$R^5$, and
(24) —$(CH_2)_n$—$S(O)_2$—$R^5$,
wherein phenyl and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene $(CH_2)$ in $R^6$ is unsubstituted or substituted with one to two groups independently selected from halogen, hydroxy, and $C_{1-4}$ alkyl; or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^7$ is independently selected from the group consisting of:
(1) hydrogen, and
(2) $C_{1-8}$ alkyl,
wherein alkyl is unsubstituted or substituted with one to three groups independently selected from halogen, $C_{1-4}$ alkyl, hydroxy, and $C_{1-4}$ alkoxy;

each $R^8$ is independently selected from the group consisting of:
(1) $C_{1-6}$alkyl,
(2) —$(CH_2)_n$phenyl,
(3) —$(CH_2)_n$naphthyl,
(4) —$(CH_2)_n$heteroaryl,
(5) —$(CH_2)_n C_{2-7}$heterocycloalkyl,
(6) —$(CH_2)_n C_{3-7}$cycloalkyl,
(7) halogen, (8) —OR$^5$,
(9) —(CH$_2$)$_n$N(R$^5$)$_2$,
(10) —(CH$_2$)$_n$C≡N,
(11) —(CH$_2$)$_n$CO$_2$R$^5$,
(12) —NO$_2$,
(13) —(CH$_2$)$_n$NR$^5$S(O)$_p$R$^5$
(14) —(CH$_2$)$_n$S(O)$_p$N(R$^5$)$_2$,
(15) —(CH$_2$)$_n$S(O)$_p$R$^5$,
(16) —(CH$_2$)$_n$NR$^5$C(O)N(R$^5$)$_2$,
(17) —(CH$_2$)$_n$C(O)N(R$^5$)$_2$,
(18) —(CH$_2$)$_n$NR$^5$C(O)R$^5$,
(19) —(CH$_2$)$_n$NR$^5$CO$_2$R$^5$,
(20) —(CH$_2$)$_n$NR$^5$C(O)-heteroaryl,
(21) —(CH$_2$)$_n$C(O)NR$^5$N(R$^5$)$_2$,
(22) —(CH$_2$)$_n$C(O)NR$^5$NR$^5$C(O)R$^{53}$
(23) —O(CH$_2$)$_n$C(O)N(R$^5$)$_2$,
(24) —CF$_3$,
(25) —CH$_2$CF$_3$,
(26) —OCF$_3$, and
(27) —OCH$_2$CF$_3$,
wherein phenyl, naphthyl, and heteroaryl are unsubstituted or substituted with one to three substituents independently selected from halogen, hydroxy, C$_{1-4}$ alkyl, trifluoromethyl, and
C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy;
each R$^9$ is independently selected from the group consisting of:
(1) hydrogen,
(2) —OH,
(3) C$_{1-8}$alkyl,
(4) —OC$_{1-8}$alkyl,
(5) halogen;
(6) —NR$^5$,
(7) —SR$^5$, and
(8) —CF$_3$,
wherein two C$_{1-8}$alkyl substituents along with the atoms to which they are attached can form a 4- to 8-membered ring;
r is 1 or 2;
s is 1 or 2;
n is 0, 1, 2, or 3; and
p is 0, 1, or 2.
12. The compound of claim 1 of structural formula IIIa or IIIb of the indicated trans relative stereochemical configuration:

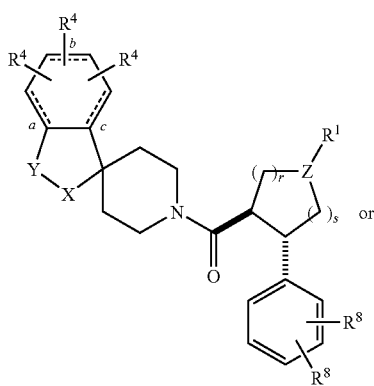

(IIIa)

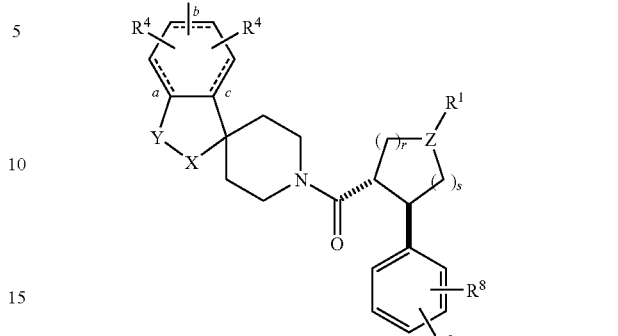

(IIIb)

or a pharmaceutically acceptable salt thereof, wherein a, b and c are all single bonds or all double bonds;
Y is selected from the group consisting of:
(1) —C(R$^7$)(R$^6$), and
(2) —N(R$^6$);
X is selected from the group consisting of:
(1) CH$_2$,
(2) C(O),
(3) oxygen,
(4) sulfur,
(5) S(O), and
(6) S(O)$_2$;
Z is selected from the group consisting of:
(1) CH, and
(2) N;
R$^1$ is selected from the group consisting of:
(1) —(CH$_2$)$_n$C$_{2-7}$heterocycloalkyl, and
(2) —N(R$^7$)C$_{2-7}$heterocycloalkyl,
wherein heterocycloalkyl, and (CH$_2$)$_n$ are unsubstituted or substituted with one to three groups independently selected from R$^3$ and oxo;
each R$^3$ is independently selected from the group consisting of:
(1) C$_{1-8}$ alkyl,
(2) —(CH$_2$)$_n$phenyl,
(3) —(CH$_2$)$_n$naphthyl,
(4) —(CH$_2$)$_n$heteroaryl,
(5) —(CH$_2$)$_n$C$_{2-7}$heterocycloalkyl,
(6) —(CH$_2$)$_n$C$_{3-7}$cycloalkyl,
(7) halogen,
(8) —OR$^5$,
(9) —(CH$_2$)$_n$N(R$^5$)$_2$,
(10) —(CH$_2$)$_n$C≡N,
(11) —(CH$_2$)$_n$C(O)OR$^5$,
(12) —(CH$_2$)$_n$OC(O)R$^5$,
(13) —NO$_2$,
(14) —(CH$_2$)$_n$NR$^5$S(O)$_p$R$^5$,
(15) —(CH$_2$)$_n$N(S(O)$_p$R$^5$)$_2$,
(16) —(CH$_2$)$_n$S(O)$_p$N(R$^5$)$_2$,
(17) —(CH$_2$)$_n$S(O)$_p$R$^5$,
(18) —(CH$_2$)$_n$NR$^5$C(O)N(R$^5$)$_2$,
(19) —(CH$_2$)$_n$C(O)N(R$^5$)$_2$,
(20) —(CH$_2$)$_n$NR$^5$C(O)R$^5$,
(21) —(CH$_2$)$_n$NR$^5$CO$_2$R$^5$,
(22) —(CH$_2$)$_n$NR$^5$C(O)-heteroaryl,
(23) —(CH$_2$)$_n$C(O)NR$^5$N(R$^5$)$_2$,
(24) —(CH$_2$)$_n$C(O)NR$^5$NR$^5$C(O)R$^5$,
(25) —O(CH$_2$)$_n$C(O)N(R$^5$)$_2$,

(26) —CF$_3$,
(27) —CH$_2$CF$_3$,
(28) —OCF$_3$, and
(29) —OCH$_2$CF$_3$,
wherein phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;

each R$^4$ is independently selected from the group consisting of:
(1) hydrogen,
(2) C$_{1-8}$ alkyl,
(3) halogen,
(4) —OR$^5$,
(5) —(CH$_2$)$_n$N(R$^5$)$_2$,
(6) —(CH$_2$)$_n$C≡N,
(7) —NO$_2$, and
(8) —CF$_3$,
wherein alkyl and (CH$_2$) are unsubstituted or substituted with one to three substituents independently selected from halogen, hydroxy, oxo, C$_{1-4}$ alkyl, trifluoromethyl, and C$_{1-4}$ alkoxy;

each R$^5$ is independently selected from the group consisting of:
(1) hydrogen,
(2) C$_{1-8}$alkyl,
(3) —(CH$_2$)$_n$C$_{3-7}$cycloalkyl,
(4) —(CH$_2$)$_n$C$_{2-7}$heterocycloalkyl,
(5) —(CH$_2$)$_n$phenyl,
(6) —(CH$_2$)$_n$naphthyl,
(7) —(CH$_2$)$_n$heteroaryl, and
(8) —(CH$_2$)$_n$C$_{3-7}$ bicycloalkyl,
wherein alkyl, phenyl, heteroaryl, heterocycloalkyl, naphthyl, cycloalkyl, bicycloalkyl and (CH$_2$) are unsubstituted or substituted with one to three groups independently selected from halogen, C$_{1-4}$ alkyl, hydroxy, and C$_{1-4}$ alkoxy, or wherein two R$^5$ groups together with the atom to which they are attached form a 4- to 8-membered mono- or bicyclic ring system optionally containing an additional heteroatom selected from O, S, and —NC$_{1-4}$ alkyl;

each R$^6$ is independently selected from the group consisting of:
(1) C$_{1-6}$ alkyl,
(2) —(CH$_2$)$_n$heteroaryl,
(3) —(CH$_2$)$_n$C(O)(CH$_2$)$_n$N(R$^5$)$_2$,
(4) —(CH$_2$)$_n$C(O)(CH$_2$)$_n$NR$^7$R$^8$,
(5) —(CH$_2$)$_n$CN,
(6) —(CH$_2$)$_n$N(R$^5$)$_2$,
(7) —(CH$_2$)$_n$N(R$^5$)C(O)R$^5$,
(8) —(CH$_2$)$_n$N(R$^5$)C(O)OR$^5$,
(9) —(CH$_2$)$_n$N(R$^5$)—S(O)—C$_{1-8}$ alkyl, and
(10) —(CH$_2$)$_n$N(R$^5$)—S(O)$_2$—C$_{1-8}$ alkyl,
wherein heteroaryl is unsubstituted or substituted with one to three groups independently selected from R$^3$, and wherein alkyl is unsubstituted or substituted with one to three groups independently selected from R$^3$ and oxo, and wherein any methylene (CH$_2$) in R$^6$ is unsubstituted or substituted with one to two groups independently selected from halogen, hydroxy, and C$_{1-4}$ alkyl; or wherein two R$^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from R$^3$ and oxo;

each R$^7$ is independently selected from the group consisting of:
(1) hydrogen, and
(2) C$_{1-8}$ alkyl,
wherein alkyl is unsubstituted or substituted with one to three groups independently selected from halogen, C$_{1-4}$ alkyl, hydroxy, and C$_{1-4}$ alkoxy;

each R$^8$ is independently selected from the group consisting of:
(1) C$_{1-6}$ alkyl,
(2) —(CH$_2$)$_n$-heteroaryl,
(3) halogen,
(4) —OR$^5$,
(5) —NO$_2$,
(6) —SR$^5$, and
(7) CF$_3$,
wherein heteroaryl is unsubstituted or substituted with one to three substituents independently selected from halogen, hydroxy, C$_{1-4}$ alkyl, trifluoromethyl, and C$_{1-4}$ alkoxy, and wherein alkyl and (CH$_2$)$_n$ are unsubstituted or substituted with one to three substituents independently selected from halogen, hydroxy, oxo, C$_{1-4}$ alkyl, trifluoromethyl, and C$_{1-4}$ alkoxy;

r is 1 or 2;
s is 1 or 2;
n is 0, 1, 2, or 3; and
p is 0, 1, or 2.

13. The compound of claim 10 selected from the group consisting of:

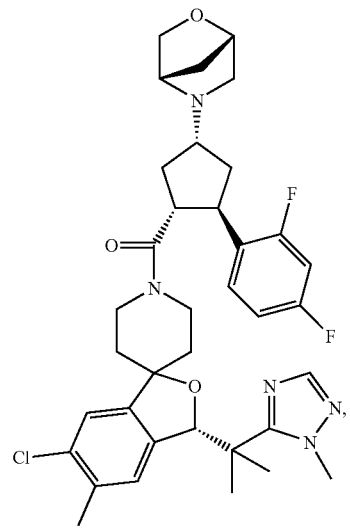

157 158
-continued -continued

-continued
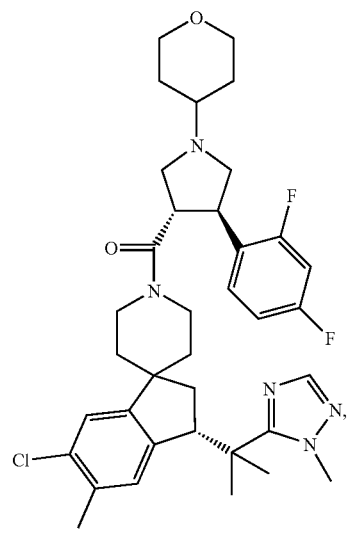
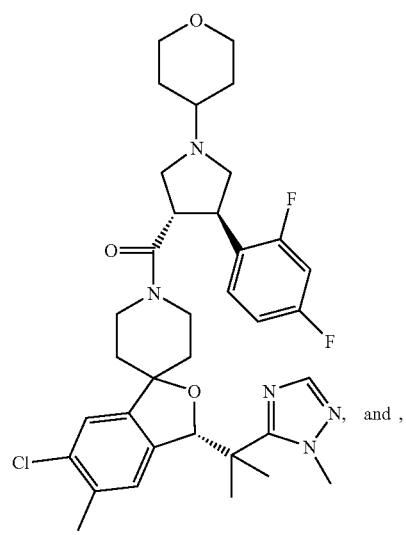
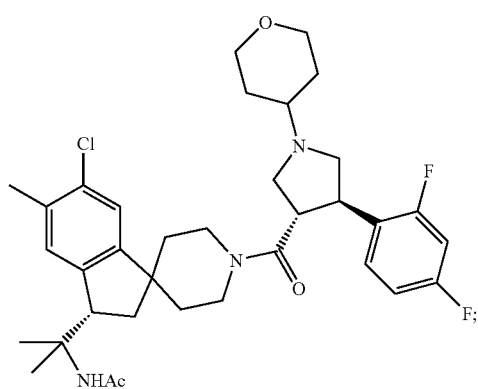
or a pharmaceutically acceptable salt thereof.
14. The compound of claim 13 which is:
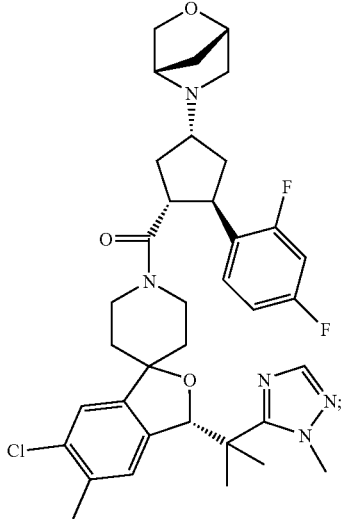
or a pharmaceutically acceptable salt thereof.
15. The compound of claim 13 which is:
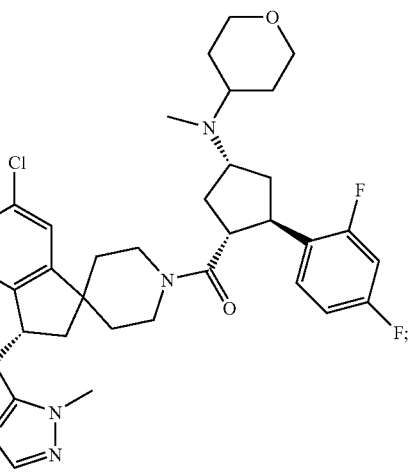
or a pharmaceutically acceptable salt thereof.

16. The compound of claim 13 which is:

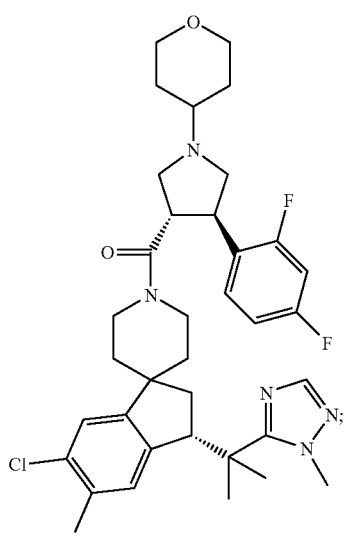

or a pharmaceutically acceptable salt thereof.

17. The compound of claim 13 which is:

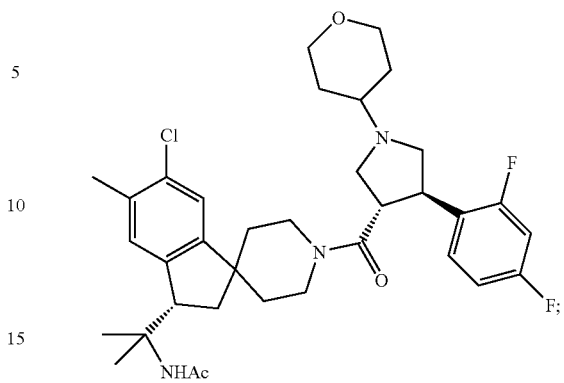

or a pharmaceutically acceptable salt thereof.

18. A pharmaceutical composition which comprises a compound of claim 1, or a pharmaceutically acceptable salt thereof, and a pharmaceutically acceptable carrier.

19. The compound of claim 13 wherein the pharmaceutically acceptable salt thereof is the trifluoroacetic acid salt.

* * * * *